(12) United States Patent
Trempy et al.

(10) Patent No.: US 7,256,029 B2
(45) Date of Patent: Aug. 14, 2007

(54) BIOPOLYMER THICKENER

(75) Inventors: Janine E. Trempy, Corvallis, OR (US); Eric P. Knoshaug, Golden, CO (US); William E. Sandine, Temecula, CA (US); Jeff A. Ahlgren, Santa Barabara, CA (US); Karen P. Dierksen, Lebanon, OR (US)

(73) Assignees: United States of America, as Represented by the Secretary of Agriculture, Washington, DC (US); The State of Oregon by and Through the Oregon State Board of Higher Education on behalf of Oregon State University, Corvallis, OR (US)

( * ) Notice: Subject to any disclaimer, the term of this patent is extended or adjusted under 35 U.S.C. 154(b) by 542 days.

(21) Appl. No.: 10/182,960

(22) PCT Filed: Feb. 2, 2001

(86) PCT No.: PCT/US01/03404

§ 371 (c)(1),
(2), (4) Date: Aug. 2, 2002

(87) PCT Pub. No.: WO01/57234

PCT Pub. Date: Aug. 9, 2001

(65) Prior Publication Data

US 2003/0186392 A1    Oct. 2, 2003

Related U.S. Application Data

(60) Provisional application No. 60/179,888, filed on Feb. 2, 2000, provisional application No. 60/241,098, filed on Oct. 16, 2000.

(51) Int. Cl.
*C12N 9/00* (2006.01)
*C12N 9/10* (2006.01)
*C07H 21/04* (2006.01)

(52) U.S. Cl. .............................. 435/193; 435/4; 435/6; 435/69.1; 435/183; 435/252.3; 435/320.1; 435/97; 435/101; 536/23.2; 536/23.4; 536/23.5; 536/23.6; 536/23.7; 530/350

(58) Field of Classification Search .................... 435/4, 435/6, 69.1, 183 T, 252.3, 320.1; 536/23.2 T; 530/350
See application file for complete search history.

(56) References Cited

U.S. PATENT DOCUMENTS 5,055,455 A    10/1991    Pier (Continued)

FOREIGN PATENT DOCUMENTS

| WO | WO 99/54475 A2 | 10/1999 |
|---|---|---|
| WO | WO99/62316 | 12/1999 |

OTHER PUBLICATIONS

Declaration of Randall Thunell dated Jan. 14, 2005.

(Continued)

*Primary Examiner*—Manjunath Rao
(74) *Attorney, Agent, or Firm*—Klarquist Sparkman, LLP

(57) ABSTRACT

A novel strain of *Lactococcus lactis* subspecies *cremori* ("Ropy 352") has been identified and isolated. Ropy 352 produces a previously unknown exopolysaccharide (EPS 352) that when expressed or added to milk, imparts highly desirable sensory characteristics to the milk, including making the milk very thick, with a very smooth mouth-feel, and slightly sweet with an obvious "chewable-bite".

15 Claims, 15 Drawing Sheets

U.S. PATENT DOCUMENTS 5,786,184 A     7/1998    Mollet et al.
5,854,034 A    12/1998    Pollock et al.
5,955,602 A     9/1999    Favre et al.

OTHER PUBLICATIONS

Cerning, J., et al., "Isolation and Characterization of Exopolysaccharides from Slime-Forming Mesophilic Lactic Acid Bacteria," *J Dairy Sci*, 75:692-699, 1992.

Dierksen, K.P., et al., "Expression of Ropy and Mucoid Phenotypes in *Lactococcus lactis*," *J Dairy Sci*, 80:1528-1536, 1997.

Dierksen, K.P., et al., "Polysaccharide Expression in *Lactococci*," *Dev Biol Stand*, 85:469-480, 1995.

Dierksen, K.P., "Regulation of Exopolysaccharide Synthesis," *Dissertation, Oregon State University*, 1998.

Franklin, M.J. and Ohman, D.E., "Identification of *algI* and *algJ* in the *Pseudomonas aeruginosa* Alginate Biosynthetic Gene Cluster Which Are Required for Alginate O Acetylation," *J. Bacteriology*, 178:2186-2195, 1996.

Katzen, F., et al., "*Xanthomonas campestris* pv. Campestris *gum* Mutants: Effects on Xanthan Biosynthesis and Plant Virulence," *J. Bacteriology*, 180:1607-1617, 1998.

Knoshaug, E.P., "Exopolysaccharide Biosynthesis by a Natural Lactococcal Ropy Isolate," *Dissertation, Oregon State University*, 1999.

Knoshaug, E.P., et al., "Growth Associated Exopolysaccharide Expression in *Lactococcus lactis* subspecies *cremoris* Ropy352," *J Dairy Sci*, 83:633-640, 1999.

Low, D., et al., "Role of *Streptococcus thermophilus* MR-1C Capsular Exopolysaccharide in Cheese Moisture Retention," *Applied and Environmental Microbiology*, 64:2147-2151, 1998.

Martinez-Salazar, J.M., et al., "Characterization of the Genes Coding for the Putative Sigma Factor AlgU and Its Regulators MucA, MucB, MucC, and MucD in *Azotobacter vinelandii* and Evaluation of Their Roles in Alginate Biosynthesis," *J. Bacteriology*, 178:1800-1808, 1996.

Van Kranenburg, R., et al., "Molecular characterization of the plasmid-encoded eps gene cluster essential for exopolysaccharide biosynthesis in *Lactococcus lactis*," *Molecular Microbiology*, 24:387-397, 1997.

Stingele, F., et al., "Identification and Characterization of the *eps* (Exopolysaccharide) Gene Cluster from *Streptococcus thermophilus* Sfi6," *J. Bacteriology*, 178:1680-1690, 1996.

Stingele, F., et al., "Introduction of the exopolysaccharide gene cluster from *Streptococcus thermophilus* Sfi6 into *Lactococcus lactis* MG1363: production and characterization of an altered polysaccharide," *Molecular Microbiology*, 32:1287-1295, 1999.

Nakajima et al., "Structure of the Extracellular Polysaccharide from Slime-Forming *Lactococcus lactis* subsp. *cremoris* SBT 0495," *Carbohydr. Res. 224*:245-253 (1992).

van Kranenburg et al., "Genetics and Engineering of Microbial Exopolysaccharides for Food: Approaches for the Production of Existing and Novel Polysaccharides," *Curr. Opin. Biotechnol. 10*:498-504 (1999).

Welman et al., "Exopolysaccharides from Lactic Acid Bacteria: Perspectives and Challenges," *Trends Biotechnol. 21*:269-274 (2003).

Sequence of Two Genes (EpsM and EpsN) Necessary for EPS352 Expression
(2265 base pairs from the start of EpsM to the end of EpsN)

```
gtctctctttaataatttttccctgaattaattcgaatttaaactcgcttttaaattagtcatatatcatgtcaaatattaagtctt
cagagagaaattatttaaaaaggaactaattaagctaaattgagcgaaaattaatcagtagtaccagttctatcaattcagaa
Q R E N Y L K R E L N - A - N W G S I K L S E N L I S I I V P V Y N S E ttcataaattctgcgcgataagtatcagataattagttgatagtttatataactccataaaactaattactaccagtgactaccgagtgttctgattaatcg
agtatttaagagcggctattcatagtctattataactcaaactatcaaatatgaagtattttgattaattgatgatggtccactgatggtcacaagagctaattagc
K Y L R A A I H S L L N Q T Y Q N I E V I L I N D G S T D G S Q E L I S agtaaagttttttctctatttctaattaatatattgatttttagaccccatagcgtacgtctcttttaataccataatctcgatcaccaagcatataatac
tcattcaaaaaaggataaagaattaatatataaatctgggtgtatcgactagagcctagtgggtcgtgtatatatg
S F Q K R K D K R I R K L Y N T K N L G V S H A R N Y G I D R A S G S Y I M aaaaatctgggtctgtgtgaatactatttcaatgacaaatcttacattactgacactacaacaatactctcattaatgatatactgtttt
ttttagaccgagacgacactttatgataaagtactgtttagaaaatattggtgttgataataagtttaatgctgatgttgttatgagtaattactatatatgcaaa
F L D P P D D T Y D K S Y C L E M I G L I N K F N A D V V M S N Y Y I C K ccgttttttatatataggattacaattactagaagaactttacactcgggatagttccctatttgtacgcaagtatgatagactatgtcaaatttccc
ggcaaaatatatatatcctaatgttaatgatcttttgaatgcctccatcaaggataaacaaatgcgttcaatactatctgatacaggttttaaaggg
G K N I Y P N V N N D L L E C E G L L S R D K T M R S I L S D T G F K G aaacataccctgtcctaaaatctttttacattaattattacaagtactcctgtattcttaatgaatctcctcgtacaataatatataatcatataacatgtattat
ttgtcatggacaagaattttagaaaaaattataattatataatatgtataattactttagaagacataatattttaatatattttaagtattagtatataat
F V W T R I F R K N V I N N V K F N E S I N Y L B D M L F N I S I V B N cgttcttaatatcggatatgttctattttctgtaataaaaataatttctctctaagacgtagtttaaatcgttagaaaaaaattaggaattagaataa
gcaagaattatagcctatacaaatacaaatagacattatttttattcaaagagattctgcatcaaaatcttagcaaatcttttaatctttatt
A R I I A Y T N K R E Y F Y L Q R E D S A S K K F S K S F F R S L N L I tctccctttcaactaggactttaaaataagcgtttaactaagacgtaaataaaaatattaaatcaacctacaattattgactctcttcctctttatcagtttgaa
agagggaaagttgatcctagctattgcgaattctgtttattcgatttgattgttaatactgagaagaagtaggagaaaatagtcaattt
R G K V D P P B F Y S Q I D S V I F Y N L V G W L I T B R K S R B N S Q F tattcctctttataattttatactttaggttttcaatcaatttgcgaatttctcaattttgggttattttaaattataattttaaagttagctagctgtttccctta
ataagagaaaattaaattaaatatgaatcccagtaagtttaaaacgcttaaaatgaaaaccaataaaaaaatttaattataattaagctatgctgtttccctta
I R R N I K N M K S Q V K F R T L K M E N P I K N L I K L S Y A F P L
```

```
tttttgtaacaacaataaggattctaacatatctatatcctttgcgagacccagataatactcattagcgggccttttttaagaaaagcctgctgcggtaaaaacat
aaaacattgttgttgttccctaagattgtatagatagtaatcgctctggtctctatt̀gataatcgcccgaaaaaatctttcggacgacgccatttttgta
K   N   I   V   V   I   S   L   R   L   Y   R   Y   R   K   R   S   G   S   I   M   S   N   R   P   E   K   F   F   S   D   D   A   I   F   V tgt*atactgaataatctaaaaatactagtcatatttaagcccttacatttatcaataactgttgtaatcgaagaaggtctaagcttt
aca*tatgacttattagatttttatgatcagtataaaattcgggagcagtagtggtaaaatagttatgacaacattagctcttttccagattcgaaa
 T   *   Y   D   L   L   D   F   F   Y   D   Q   Y   K   I   R   E   L   G   A   V   V   G   K   I   V   M   T   T   L   A   S   F   P   D   S   K tttaacatattacttagttagttagttctaataaattctaataatttctgtatgattgcctattttacatacaattttacatacaa
aattgtataatgaattaatcaatcagaaaaagtatattattcaatagaaaagatattcaataagacatactaaaacgatatactatgtaaaatgtatgtt
K   L   Y   N   E   L   N   P   I   R   K   K   V   F   K   D   Y   I   S   I   B   K   R   B   T   K   R   I   K   M   Y   K   M   Y   V aaaagaagaataacctatatttgaaatgtctgaccttccattgtgacctgaagtaaaagtaaaacactgataataattttaatcttatttatg           * ISS1 insertion
ttttcttcttatgttggatataaacttttacagactttacagactgaagtgaaaaggtaaaacactgataataattttaatcttatttatg                          site
 F   S   S   Y   V   G   Y   R   L   V   R   R   L   V   Y   R   L   V   R   K   G   K   B   W   K   -   I   -   F   L   I   L   F   M
```

Figure 2C

B. Alignments
1) Alignment of EpsM to EpsN

```
EpsM  LSENLISIIVPVYNSEKYLRAAIHSLLNQTYQNIEVILINDGSTDGSQELISSFQKKDKR---IKLYNTKNLGVSHARNYGIDRA
EpsN  -MNPLISIIVPIYNVEKYIGSLVNSLLKQTNKNFEEVIFIDDGSTDESMQILKEIMAGSEQEFSFKLLQQVNQGLSSARNIGILNA
      : ********:** ***::  ::*****:**  :*:****:*:****** *  ::  ::  :** : * *:* *** ** . *

EpsM  SGSYIMFLDPDDTYDKSYCLEMIGLINKFN-ADVVMSNYYICK---GKNIYPNVNNDLLECEGLLSRDKTMRSILSDTGFKGFVWT
EpsN  TGEYIFFLDSDDEIESNFVETILTSCYKYSQPDTLIFDYSSIDEFGNALDSNYGHGSIYRQKDLCTSEQILTALSKDEIPTTAWS
      :*.**:***.**  .*.    *::  : :.   * *.:: :*    . :    . * .  :*.  :  *. .:: :**  .*:

EpsM  RIFRKNVINNVKFNESIN-YLEDMLFNISIVHNARIIAYTNKRHYFYLQREDSASKKFSKSFFKSLNLIRGKVDPEFYSQIDSVI
EpsN  FVTKRSVIEKHDLLFSVGKKFEDNNFTPKVFYFSKNIVVISLRLYRYKKRSGSIMSNRPEKFFSDDAIFVTYDLLDFYDQYKIRE
       :  :::**:: : *. *   **:  *::*:*::::: ::  *     : ..**   :** *:  :  *:.  **:* : :

EpsM  FYNLVG-WLITERKSRENSQFIRRNIKNMKSQVKFKTLKMENPIKNLILKLSYAFPLVGSCMIHMLSVFMKTKLYSKLMSMLRKG
EpsN  LGAVVGKIVMTTLASFPDSEKLYNELNPIRKKVFKDYISIEKRHTKR-IKMY-------VKMYVFSSYVGYKLYRLVKGKHWK-
      : *  *  ::*   *  :.:: :.  :.::*.* ** : ::*. :*  *::        *  *:** :  ** **:: : .
```

Figure 3A

2) Alingment of EpsM to EpsG (a Lactococcus lactis glycosyltransferase involved in a different EPS operon)
```
EpsM  LSENLISIIVPVYNSEKYLRAAIHSLLNQTYQNIEVILINDGSTDGSQELISSFQKKD-KRIKLYNTKNLGVSHARNYGIDRASG
EpsG  ---MIKLSIIIPIYNVEKYLSKCLNSILEQTYKEIEIILVNDGSTDNSKDIAVSYCERFPNVFKYFEKDNGGLSSARNFGLEKISG
       :***:*:** ****    .::*::****::***:***::*:*:::  *: :: :   :* ::..* *:* ***:*::::: **

EpsM  SYIMFLDPDDTYDKSYCLEMIGLINKFNADVVMSNYYICKGKNIYPNVNNDLLECEGLLSRDKTMRSILSDTGFKGFVWTRIFRK
EpsG  DFVGFLDSDDYIDNDLYEIMINSL---D-----SSIKIVECDFIWEYENGKSVLDK---TSEYNSIKDLMVNG--RVVAWNKIYNV
      .:: ***.** *::  **:: *:. *   :   .     * .:* .*:   *...*     ..:.::*: * .:*.*:::.::.

EpsM  NVIN--NVKFNESINYLEDMLFNISIVHNARIIAYTNKRHYFYLQREDSASKKFSKSFFKSLNLIRGKVDPEFYSQIDSV---IFY
EpsG  EWLEKINIKFKBGLLY-EDLNFFKIVPHLTSISEVSTVKNSFVHYVQHKGTITSDNSLNILDIIKSYEDVFHYYNEKQINDLYF
       * ::  *::*:: :* **:  :* :   :   : ..:.:*:     :*.*.    .::..::*::  :*.:*:   ::.

EpsM  NLVGWLITERKSRENSQFIRRNIKN-MKSQVKFKTLKMENPIKNLILKLSYAFPLVGSCMIHMLSVFMKTKLYSKLMSMLRKG
EpsG  DELEYKFSRNLMG---APLKRAIKIDKRQRKIILDEFWNNVLSYYPNWKKNKYIKKLSKQNILFFINKYTY-KLFYLL---
      :  ::. :.*.: .   : :: **::  :.::  ::  :*   : : ::* . *:        ::    * ::   *: :*

3) Alingment of EpsN to EpsG
EpsN  MNPLISIIVPIYNVEKYIGSLVNSLLKQTNKNFEVIFIDDGSTDESMQILKEIMAGSEQEFSFKLLQQVNQGLSSARNIGILNAT
EpsG  -MIKLSIIIPIYNVEKYLSKCLNSILEQTYKEIEIILVNDGSTDNSKDIAVSYCERFPN---VFKYFEKDNGGLSSARNFGLEKIS
       :*::.*** *********:.. :*.::::* *::*:*:.****:* :*  . :.    *  *  *:*:*.*******:*: :

EpsN  GEYIFFLDSDDEIESNFVETILTSCYKYSQPDTLIFDYSSIDEFGNALDSNYGHGSIYRQKDLCTSEQILTALSKDEIPTTAWSF
EpsG  GDFVGFLDSDDYIDNDLYEIMIN-----SLDSSIKIVECDFIWEYEN--------GKSVLDKTSEYNSIKDLMVNG---RVV----AWNK
      *:: ****** *..::::* :       ::*..: .:*.:*      ::      *: :* *: ..:   :  .     **:.

EpsN  VTKRSVIEKHDLLFSVGKKFEDNNFTPKVFVYFSKNIVVIS---LRLYRYRKRSGSIMS---NRPEKFFSDDAIFVTYD---LLD
EpsG  IYNVEWLEKINIKFKEGLLYEDLNFFKIVPHLTSISEVSTVKNSFVHYVQHKGTITSDNSLNILDIIKSYEDVFHYYNEKQIND
      : :  :::*::::*  *  :**:**:*:.  :*.  *:.     :.* *:.: .*:.:        :: .::.*  :    :

EpsN  FYDQYKIRELGAVVGKIVMTTLASFPDSEKLYNELNPIRKKVFKDYISIEK-RHTKRIKMYVKMYVFSSYVGYKLYRLVKGKHWK
EpsG  LYFDELEYKFSRNLMGAFLKRAIKIKDKRQRKIILDEFWNNVLSYYPNWRKNKYIKKLSKQNILFFINKYTYKLFYLL-------
      :** :   : .: :    :* :       .::: :    :.: . ::: *  ::*:: *  ::. *  . *  :*
```

Figure 3B

Eps352 Operon seqeunce EpsR-EpsK (primer EpsOPF-EpsOPR) corrected as of May8, 2000

```
GTTGAAAAACCCTACCTTTACTTGCACTAATAGTTTTATTTATTGATATATATTGAAAATTAAAAACACCAAAATGGTTAACTTAAG
CAACTTTTGGGATGGAAATGAACGTGATTATCCAAAATAAAATATATTAGTAACTATATATTATAACTTTTAATTTTTGTGGTTTACCAAATTGAATTC

CAAGTTTGATTAATTTTCAGAAAAATTAAGGTTTTTCTTACAGAAGTAATAATAAAAAGGATTATATATTATGAATAATTATTTTACCATCGTCTA
GTTCAAAACTAAATTAAAAGTCTTTTTAATTCCAAAAGAATGTCTTCAATTATTTTTCCCTAATATAAATACTTATAAATAAATGGTAGCAGAT
                                                       M  N  N  L  F  Y  H  R  L

AAGGAACTAGTTGAATCAAGTGGTAAATCTGCAAATCAAATAGAAAGGGAATTGGGTTACCCTAGAAATTCTTGAATAATTATAAGTTGGGAGGAGAAC
TTCCTTGATCAACTTAGTTCACCATTAGACGTTTAGTTATCTTTCCCTTAACCAATGGGATCTTTAAGAACTATTAATAATTCAACCCTCCTCTTG
 K  E  L  V  E  S  S  G  K  S  A  N  Q  I  E  R  E  L  G  Y  P  R  N  S  L  N  N  Y  K  L  G  G  E

CCTCTGGGACAAGATTAATAGGACTATCAGAGTATTTTAAGTGTCTCCAAAATATCTGATGGGTATAATTGATGAGCCTAATGACAGTTCTGCAATTAA
GGAGACCCTGTTCTAATTATCCTGATAGTCTCATAAAATTACACAGAGTTTTATAGACTACCCATATTAACTACTCGGATTACTGTCAAGACGTTAATT
 P  S  G  T  R  L  I  G  L  S  E  Y  F  N  V  S  P  K  Y  L  M  G  I  I  D  E  P  N  D  S  A  I  N

TCTTTTTAAAACTCTAACTCAAGAGAGAAAAAAGAAATGTTTATAATTTGTCAAAAATGGCTTTTTTAGAATATCAAATAGAGTTATAACAATAATAA
AGAAAAATTTGAGATTGAGTTCTCTCTTTTTCTTTACAAATATTAAACAGTTTTACCGAAAAAATCTTATAGTTTATCTCAATATTGTTATTATT
     L  F  K  T  L  T  Q  E  E  K  K  E  M  F  I  I  C  Q  K  W  L  F  L  E  Y  Q  I  E  L

ATTTAGGGAGTTTTTTCGGTAGTGTAAATAAGTTTGTTTTATATGAAGCTCCACTTTTTAATGATAACCAAAAACATTGAAGCAACAGCCTCATGGACTAGTAA
TAAATCCCTCAAAAAGCCATCATCCATTTCAAAACCTTATTCAAACAATATACTTCGAGGTGAAAATTACTATTGGTTTTGTAACTTCGTTGTCGAGTACCTGATCATT
 Q  N  Q  V  L  A  T  N  P  D  V  V  L  Y  E  A  P  L  F  N  D  N  Q  N  I  E  A  T  A  S  W  T  S  N

AAAAATCAAGTATTGGGCACTAACCCTGATGTGTTTTATATGAAGCTCCACTTTTTAATGATAACCAAAAACATTGAAGCAACAGCCTCATGGACTAGTAA
TTTTAGTTCATAACCGCTGATTGGGACTACAACAAAATATACTTCGAGGTGAAAATTACTATTGGTTTTGTAACTTCGTTGTCGGAGTACCTGATCATT
                                                        N  K  F  W  N  N  I  T  Y  N  G  E  T  S  E  Q  L  L  A  E  K  V

TGAGCAACTTATAACAAATTGGCTAGTACAGGAGCAGAGGTGATAGTTCAACCCTCTCCACCGATTTATGGTGGTGTGTGTACCCGTACAAGAAGAA
ACTCGTTGAATATTGTTTAAACCGATCATGTCCTCGTCCATCAAGTGGGAGAGGTGGCTAAATACCACCACAACATGGGCATGTTCTTCTT
 E  Q  L  I  T  N  L  A  S  T  G  A  E  V  I  V  Q  P  S  P  P  I  Y  G  G  V  V  Y  P  V  Q  E  E

CAGTTAAACAATCTTATCTACAAAGTATCCCTATATAGACTACTGGGCTAGTACCCAGACAAAAATTCTGATGAAATGAAGGGCTGGTTTCTGATG
GTCAAATTTGTAGAAATAGATGTTTCATAGGATATATCTGATGACCCCGATCAATGGGTCGTGTTTTACTTTAAGACTACTTTACTTCCCGACCAAAGACTAC
 Q  F  K  Q  S  L  S  T  K  Y  P  Y  I  D  Y  W  A  S  Y  P  D  K  N  S  D  E  M  K  G  L  V  S  D
```

```
TTTCCTCAACGAGCAGATTTAGAACTCTATTATCTCCAGTACCATAGCAGCCAAAAATGATATCAAGCTTCTAGTACTCACAATTGTACAAAGTATTAAC
AAAGGAGTTGCTCGTCTAAATCTTGAGATAATAGAGGTCATGGTCATCGTTACTATAGTTCGAAGATCATGAGTGTTAACATGTTCATAATTG
 F  P  Q  R  A  D  L  E  L  Y  Y  L  Q  Y  H  S  T  K  N  D  I  K  L  L  V  L  T  I  V  Q  S  I  N

GGATCGGACGCCATATTAAAAAATGAAAATAGCATTAGTAGGTTCCAGCCGTTCCAGCCGGTGCCATTTGACACCTGTATTGTTAAAAAAGTTTGGGAAAACGAAG
CCTAGCCCTGCGTATAATTTTTTACTTTTGCTAATCATCGAAGGTCGCCACCGTCATCATCCAAGGTGACATAAACATTTTTCAAAACCCTTTGCTTC
 G  S  D  A  Y     M  K  I  A  L  V  G  S  S  G  G  H  T  H  L  Y  L  L  K  K  F  W  E  N  E

ATAGATTTGGTCACATTTGATAAACAGATGCAAAATCTATATTGAAAGAAGAAGATTTATCCTGTTATTATCCCACAATAGAAATGTAAAAAA
TATCTAAAACCAGTGTAAACTATTTTGTCTACGTTTAGATATAACTTCTTCTTCTTTCTAAATAGGAACAATAATAGGGTGTTATCTTTACATTTTT
 D  R  F  W  V  T  F  D  K  T  D  A  K  S  I  L  K  E  E  R  F  Y  P  C  Y  Y  P  T  N  R  N  V  K  N

CACGATAAAAAATACCATTCTTGCATTTAAATACTTAGAAAGAAAAACCAGATTTGATTATTCGAGTGGTGCTGCGGTAGCCGTTCCTTTTTTTGG
GTGCTATTTTTTATGGTAAGAACGTAAATTTTATGAATCTTTTCTTTTGGTCTAACATAATAAAGCTCACCACGACGCCATCGGCAGCAAGAAAAACC
 T  I  K  N  T  I  L  A  F  K  I  L  R  K  E  K  P  D  L  I  I  S  S  G  A  A  V  A  V  P  F  W

TTAGGTAAACTATTCGGTGCAAAGACAGTCTATATTGAAATATTTGACCGGATCGATAAACCACCTTAACAGGAAAATTAGTTTATCCAGTTACTGATA
AATCCATTGATAAGCCACGTTTCTGTCAGATATAACTTTATAAACTGGCCTAGCTATTTGGTTGAATTGTCCTTTTAATCAAATAGGTCAATGACTAT
 L  G  K  L  F  G  A  K  T  V  Y  I  E  I  F  D  R  I  D  K  P  T  L  T  G  K  L  V  Y  P  V  T  D

AGTTTATAGTTCAATGGAAGAGTTAAAAAAAGTTTACCCTAAAGCCAATTAATTTAGGAGGAATTTCTAATGATTTTGTAACGGTTGAACTCACGAA
TCAAATATCAAGTTACCCTTCTCAATTTTTTCAATGGATTTCGTTAATTAAATCCTCCTTAAAGATTACTAAAACATTGCCAACCTTGAGTGCTT
 K  F  I  V  Q  W  E  E  L  K  K  V  Y  P  K  A  I  N  L  G  G  I  F     M  I  F  V  T  V  G  T  H  E

CAACCATTTAATCGACTCATTCAAAAATTGATGAACTTGTACGCGATGGTGAAATCGAAGACGATGTATTCATGCAAATTGGTACTCAACTTATGAAC
GTTGGTAAATAGCTGAGTAAGTTTTTAACTACTTGAACATGCGCTACCACTTGAACATGCGCTACCATGAAGTACGTTTAACCATGAGTTGAATACTTG
 Q  P  F  N  R  L  I  Q  K  I  D  E  L  V  R  D  G  E  I  E  D  D  V  F  M  Q  I  G  Y  S  T  Y  E

CTAAAATATACTAAATTACAACTAGGTAAAATTCGATAGTTGTTCCACGGCAAATGAAATTTGATGAGCATATAAATGAACTTACTGGCGACCATCTACCTA
GATTTATATGATTTTAATGTTGATCCATTTTAAGCTCATTTAAACAATAACCTATACCTTCTACATACTTCCGCTACCTCCGTATATTACTAGTGGAACGCCGGTAGATGGAT
 P  K  Y  T  K  W  E  K  F  I  G  Y  E  T  M  E  R  C  M  N  E  A  S  T  I  I  T  H  G  G  P  S  T  Y

TATGCAAGTATTACAACTAGGTAAAATTCCGATAGTTGTTCCACGGCAAATGAAATTTGATGAGCATATAAATGATCATCAACTTGGTGAAACCATTCATTTGTC
ATACGTTCATAATGTTGATCCATTTTAAGGCTATCAACAAGGTGCCGTTTACTTTAAACTACTGTATATTTACTAGTAGTTGAACCATTTAAGTCAAGGT
 M  Q  V  L  Q  L  G  K  I  P  I  V  V  P  R  Q  M  K  F  D  E  H  I  N  D  H  Q  L  W  V  S  K  Q

GTTGTGAAAAAGGGATACTCATTGATTTGTGCGAAGATGTTGAAGACATTCTCAAAATATATTATTAGTTCCAAAATTTCAGATACCTTACAAAAAAATG
CAACACTTTTCCCTATGAGTAACTAAAACACGCTTCTACAACTTCGTAAGAGCTTTTAAATAATTTATAATAATCAAGTTTTAAAGTCTATGAATTGTTTTTAC
 V  V  K  K  G  Y  S  L  I  L  C  E  D  V  E  D  I  L  E  N  I  I  S  S  K  I  S ·D  T  L  Q  K  N
```

Figure 5E

```
TAAATCACAACACTGAATTCATAAATTATTCAGTGCTGAAATTACCAGCTATTTATAAAAGTGAGAAGATATGATACCAAAAGTAATACACTATTGC
ATTAGTGTGTGACTTAAGTATTTTAATAAGTCACGACTTTAAATGGTCGATAAATATTTTCACTCTCTATACTATGGTTTCATTATGTGATAACG
 V  N  H  N  T  E  F  F  I  K  L  F  S  A  E  I  Y  Q  L  F  I  K  S  E  K  I  M  I  P  K  V  I  H  Y  C

TGGTTCGAGGGCAACCTTTACCAGAATCTGCGTGGCTAAAATGTATTGAAAGTTGAGAAGTTTGTCCAGATTATGAAATAAAACAATGGTCTGAGAAAA
ACCAAGCCTCCCGTTGGAAATGGTCTTAGACGCGATTTTACATAACCTTTCAAAACAGGTCTAAACTCTAATACTTTATTTGTTACCAGACTCTTTT
 W  F  G  G  Q  P  L  P  E  S  A  L  K  C  I  E  S  W  R  R  F  C  P  D  Y  E  I  K  Q  W  S  E  K  N

ACTATGATGATAAAAATTCAATATATTAAGGAAGCATATCAAGAAAAAAATTGCTTTTGTCACGGATGTGCAAGGCTCGATATAATTTGGAATGA
TGATACTACTATTTTATTTTAAGTTATATAAATCCTTCGTAGTTCTTTTTTTTAACGAAACAGTGCCTACACGTTCCGAGCTATATTAAACCTTACT
 Y  D  V  N  K  I  Q  Y  I  K  E  A  Y  Q  E  K  K  F  A  F  V  T  D  V  A  R  L  D  I  I  W  N  E

AGGCGGTATATCTTGACACGGATGTAGAGCTTATAAATCTCTTGATGAATGCTGTATAATAGTTTATATTTAGGAATGAAAGAGCTGGTAGAGTA
TCCGCCATATAGAACTGTGCCTACATCTCGAATATTTTAGAGAACTACTTAACGACATATTATCAAATATATAAATCCTTACCTTTCTGACCATCTCAT
 G  G  I  Y  L  D  T  D  V  E  L  I  K  S  L  D  E  L  L  Y  N  S  L  Y  L  G  M  E  R  A  G  R  V

AATACGGGGTTTAGGGTTTGAAGCTGAAGTAAATCATCCAATTGTGAGAGCTAATTAGAATTGTATACTAATATTCCTTTTCAGGCAATGATAATATAA
TTATGCCCAAATCGGATATGCTGCTTAGAAACCTCGACTTCATTTAGTAGGTTAACACTCTCGATTAAATCTTAAGTTGTTACTTTGTATATCTATTAAAATGATGACTTAT
 N  T  G  L  G  F  G  A  E  V  N  H  P  I  V  R  A  N  L  E  L  Y  T  N  I  P  F  S  G  N  D  N  I  T

CTTGTGTGACCTATACGACGAATCTTTTGAAAATAAACAAATATGGTCTAAAAAACAACAATGAAATTCAACATATAGATAACGCAATAATTTACCTACTGAATA
GAACACACTGGATATGCTGCTTAGAAAACTTTCAAAACTTGTTTAGCCTTTAGTTTATGCCTTTATGAATGAGGTAGGTAGTGATACTATACTTCAACCTTCTATTCTCTATTT
 C  V  T  Y  T  T  N  L  L  K  K  Y  G  L  K  N  N  E  I  Q  H  I  D  N  A  I  L  P  T  E  Y

TTTATGTCCCTCTAAGTTTTGAAACAAATCGATTAAAATAACGGAAAATACTTACTCCATCCATGATATGAGTTGGAAAGATAAGAGAGATAAA
AAATACAGGAGATTCAAAACTTTGTTTAGCTAGCTAATTTATTGCCTTTATGATGAGGTAGCTATACTCAACCTTTCAACCTTATTCTCTATTT
 L  C  P  L  S  F  E  T  N  R  L  K  I  T  E  N  T  Y  S  I  H  H  Y  D  M  S  W  K  D  R  D  K

TTTTTAAGACTTAAAATACAACTTAGAAAAATGGGTAGGTGATGATTTTTATGAAAAGTTATTAAAGAATTGGAAAATAATTATCATGAATAAAATAAC
AAAAATTCTGAATTTATGTTGAATCTTTAAAAAATACTTTTAACCTTTTATTAATAATTCTTAACCTTTTATATATAGTACTTATTTATTG
 F  L  R  L  K  I  Q  L  R  K  W  V  G  D  D  F  Y  E  K  V  I  K  R  I  G  K       M  N  K  I  T

CATGACAAGAGAGATGAGAGTTATTGCCTTATGTGTCGTAATTTTGTCGTAATTTTAGAATATTTAAATAATACAGGATTAATTGCGTCTCTTCAGCATG
GTACTGTTCCTCTACTCTCAATAACGGAATACACCGAATTACATAAAATCTTATAAATTTATTATGTCCTAATTAACCAGAAGTCGTATGAGAAATCGTAC
 M  T  R  E  M  R  V  I  A  L  C  V  V  I  L  E  Y  L  N  T  G  L  I  A  S  A  Y  S  F  S  M

GCGAGTACAATCCTCTTAGGAGAGTTATTCTCTATATCTTATTCTGTAAAAAAAGAAAAGGATTTTCTTTAAAGGAGATTATTGTACTAGTAAATCGTAG
CGCTCATGTTAGGAGAATAGGATATAAGACATTTTTTCTTTCCTAAAGAAATTCCTAATAACATGATTAAGGATTAAGGTAAATAAAACATC
 A  S  T  I  L  L  S  Y  I  L  F  C  K  K  R  R  K  G  F  S  L  K  E  I  V  L  L  I  P  F  I  E  V
```

Figure 5F

```
TTTTAAATCGTGATCCTAGTAATTTCAGTTAGGTTAATGTGGATACTCCTATTTTATGTTAAGTAAGTCGGAAATAGATTAAAAAAAGTGATGAAAAC
AAAATTTAGCACTAGGATCATTAAAGTCAATTCCAATTACACCTATGATAAAATACAATTCATTCAGCCTTTATCTAAATTTTTTCACTACTTTTG
VLNRDPSNFSLGLMWILYFMLSKSEIDLKKVMKT
ATTTTTGTTACCTCTAGTGTTTGTTTTATTTGACAATAGTACTACTTTATTAATAATGTCTCTTAATAAAAGCTCTGATGATAATGTGGCGTGAGAT
TAAAAAACAATGGAGATCACAAACTGTTATCAGAAATAAAACTGTTAGAGAATTATTTCGAGACTATACTATTACACCGCACCTCTA
FFVTSSVCFILTIVLYLIIMSLNKSSDMIMWRGD
GCTTTTATAAATCGTATGAGTTAGGATTTATCCAACCGAATTTGCAATGATGAGCTTTTAGGTATAGCCTATCGGAATAATATAAACTCATGACTTT
CGAAAATATTAGCATACTCAAATCCTAAATAGTTGGATTCAAACGTACTACTCGAAAAATCCATATCGCTATCGGAATAATATAAACTCATGACTTT
AFINRMSLGFIQPNFAMMSFLGIAIALLYLSTE
GACAAAGAATAACTATAATTTTATTGCCATTGTAACTTTTATTATATATTTACTTTACTCAATCAAGAACTTCAGGATATATCTTATTTTTATTTGAG
CTGTTTCTTATTGATATTAAAAATAACGTTAACATTGAAAATAAATGAAATGAGTTCTTGAAGTCTATATAGAATAAAAATAAAACTC
RQRITIIFIAIVTEIIFYEFTQSRTSGYILFFILS
TATTTTATTGTTAGTAGTAAAAAACTAAAAGCAAGTTTCAAATTTGAAAAAAGGAGCATTACAGTTTTACCACTACTTCTTTTAATCATCTCTAT
ATAAAATAAACAATCATCATTTTTCGATTTTGTTCAAAGTTTAAAGTTTCGTTGATGTCAAAATGGTGATGAAGAAAATTAGTAGAGAATA
ILFVSSKKTKKQVSNFEKRSITVLPLLLIHSY
TCGTTGTTAAAGTTACCTATTAATCAATACATCAATAGCTTCGTTCTGGTCGTCTGGCGCTTTATCAAGAGATTTATTCTACATTTGTATACATTGA
AGCAACAATTCAATGGATAATTAGTTATGTAGTTATCGAACGAAAGACCAGACAGATCGTTCTAAATAGTTCTAAATGATGTAAACCATATGTAAACT
SLKLPINQYINSLLSGRLALYQEIYSTFGIHL
TAGGGAATAATGATGTTAAAAATACAAGTTAGATACAAGTTAGATACAGCATATCTCAAAGTTTGCTAGCAAAAGGAATTTGTTTTACATTGTTTTATTGTAACTTT
ATCCCTATTACTACAATTTTATGTTACAATCTATGTTAGAATGTCAAAGCGATCGTTCCTAAAACAATTGTAACAAAAACAATTGAAA
IGNNDVKNTMLDTAYLQSLLAKGILFTLFTFF
CTTTTTCATATTTTTTCTTAAGAGAAAAAAACACAAACTAGGTTGCAAAGTTTAGTAATTATGATGTATTTTAATTGCATTTACAGAAACATCATTTTT
GAAAAAGTATAAAAAGAATTCTCTTTTGTCTTTGATCCAACGTTCAAATCATTAATACATTAATAAAATTAACGTAAAATGTCTTTGTAGTAAAAA
FFIFFLKRKTQTRLQSLVIMMYFLIAFTETSFF
AGGTTTGTAATTTATTTCCAGTATGATGGTAATAATGGATCAGAAAGAGGCTAATAAAGTAATAGAAAAAGGTGGCATAGTAAGAAAAACAGA
TCCAAACATTAAATAAAGGTCATAACTACCATTATTACCTCCGATTATTCTTCCGGATTATTCATTATCTTCCACCGTATCATCACTCATTATTTGTCT
REVILFPVLMVIMDQKEANKVIEKVA
GATTGAGGAATACAAAGTATCCGTTATAGTTCCTGTTTACAATGTAGAGG
CTAACTCCCTTCGTTTCATAGGCAATATCAAGGACAAATGTTACATCCC
```

Figure 5G

Seqeunce of EpsU (start and stop codons are underlined) 1612bp total
here but 1412 from start codon to stop codon

```
GGTGGACAGGAGGACACAATTTTTAATCCTTCCTGTTATATAGTTTTTGTTTAATATTTTTCGGGAGGGTT
ATTAATGCAAATCGCAAAAAATTATCTTTATAATGCAATATATCAGGTCTTTATAATAATTGTGCCATTAC
TTACCATTCCTTATTTGTCAAGAATTTTGGGCCCTTCAGGTATTGGAATTAACTCATATACCAATTCTATT
GTTCAGTATTTTGTTTTATTTGGTAGTATAGGAGTCGGTTTGTATGGGAATCGTCAGATTGCCTTTGTTAG
GGATAATCAGGTCAAAATGTCTAAAGTCTTTTATGAAATATTTATTTTAAGACTATTTACAATATGTTTAG
CATATTTTTTGTTCGTTGCTTTTTTAATCATTAATGGTCAGTATCATGCATACTATTTGTCTCAATCCATT
GCTATAGTTGCAGCTGCATTTGATATCTCTTGGTTTTTTATGGGAATTGAAAATTTTAAAGTAACTGTATT
AAGAAATTTTATAGTTAAGTTACTTGCTCTATTCAGTATTTTCCTATTTGTCAAATCTTACAATGATTTGA
ATATATATATATTGATAACAGTTTTATCTACATTAATTGGTAATTTAACTTTTTTCCCAAGTTTACACAGA
TATCTCGTAAAGGTTAACTATCGTGAATTAAGGCCAATAAAGCATTTAAAGCAATCTTTAGTCATGTTTAT
CCCACAAATTGCTGTCCAAATTTATTGGGTTTTGAATAAAACGATGTTAGGTTCATTGGATTCTGTCACGA
GCTCCGGCTTTTTTGATCAGTCTGATAAAATAGTTAAACTGGTTTTGGCTATTGCTACTGCAACAGGTACT
GTCATGTTGCCACGTGTTGCAAATGCCTTTGCACATAGAGAGTATAGTAAAATTAAGGAATACATGTACGC
AGGTTTTTCTTTTGTGTCGGCAATTTCGATTCCTATGATGTTTGGTCTGATAGCTATTACTCCTAAATTCG
TGCCACTTTTTTTTACATCTCAATTTAGTGATGTTATTCCTGTGTTAATGATCGAGTCAATCGCAATTATT
TTTATAGCTTGGAGCAACGCAATAGGTACTCAATATCTTTTACCAACTAATCAAAATAAGTCATATACAGT
GTCGGTGATCATTGGAGCGATAGTCAATTTAATGTTAAATATTCCACTGATTATATATCTAGGTACTGTTG
GTGCATCAATTGCAACTGTAATTTCTGAAATGTCTGTAACTGTGTATCAACTTTTTATAATTCATAAACAG
CTTAATTTGCATACACTGTTTGCGGATTTATCTAAGTATTTAATTGCAGGATTAGTGATGTTTCTAATTGT
CTTTAAAATTAGTTTGTTAACACCGACATCTTGGATATTCATTCTGTTGGAAATTACTGTGGGCATAATTA
TTTATGTTGTTTTATTAATATTTTTAAAGGCAGAAATAATTAATAAGCTAAAGTTTATTATGCATAAATAG
AGGTATGGATTTAGGTACCTGCCTTATTGAAAATAACGGTGAGTCAATGGTATTGGGCATATTTGACGCTC
ACCTTCAATTTGTTTTGGTCGACTTGATTGTAGCACAGGACAATATGTCT
```

BIOPOLYMER THICKENER

This is the U.S. National Stage of International Application No. PCT/US01/03404, filed Feb. 2, 2001 which was published in English under PCT Article 21 (2), which in turn claims the benefit of U.S. Provisional Application Nos. 60/179,888 filed Feb. 2, 2000 and 60/241,098 filed Oct. 16, 2000.

ACKNOWLEDGMENT OF GOVERNMENT SUPPORT

This invention was made in part with government support under The National Dairy Promotion and Research Board (i.e. Dairy Management Inc., DMI) and USDA/CSREES Special Research Grant. Accordingly the government has certain rights in this invention.

FIELD OF INVENTION

The field of the invention relates to biopolymers, enzymes that are contained within biopolymer synthesis pathways, nucleic acid sequences encoding such enzymes, and to organisms that make such biopolymers, wherein such biopolymers may be used to thicken liquids including liquid foods, as well as an additive to pharmaceuticals, beauty products, and coating agents.

BACKGROUND

Microbial polysaccharides are used for a broad variety of industrial applications including food production, chemical production (e.g., detergents, cosmetics, paints, pesticides, fertilizers, flocculants, film formers, lubricants and explosives), pharmaceutical production and waste treatment. In food production, microbial polysaccharides are commonly used as thickening, gelling and homogenizing agents. When added to a liquid, microbial biopolymers contribute to viscosity, emulsion stabilization, surface tension and adhesiveness. Thickening applications are particularly important in the production of solid and semi-solid food products including dairy and non-dairy foods such as yogurt, buttermilk, salad dressings, cheese, and ice-cream. Thickening of liquid foods is desirable because of consumer preference for such thickened foods, which have a characteristic texture and "mouth feel." Thickening of liquid drinks is also desirable for use with elderly people who frequently have problems swallowing low-viscosity liquids (e.g., milk and fruit juices) due to an impaired swallowing reflex. The addition of thickener to such drinks facilitates swallowing and reduces aspiration of liquid into the trachea.

Currently the only microbial polysaccharides used to any appreciable extent in industry are dextran, produced by *Leuconostoc mesenteroides*, xanthan gum, produced by *Xanthomonas campestris*, and gellan gum, produced by *Aureomonas elodea* ATCC31461 (Crescenzi, *Biotech. Prog.* 11:251-259, 1995). Xanthan gum was approved by the U.S. Food and Drug Administration (FDA) for use in foods in 1969. Today it is used in many foods such as bakery fillings, canned foods, frozen foods, pourable dressings, sauces, gravies, processed cheeses, and juice drinks. Xanthan gum is also used in oil recovery, pharmaceuticals, beauty products, and coating agents.

Unfortunately, *Xanthomonas campestris* is a less than ideal source of polysaccharides for use in food production, since it is known to be pathogenic, and the biopolymer it produces has long been suspected of being pyrogenic (fever-inducing). Although xanthan gum is classified as "Generally Regarded as Safe" (GRAS) by the Food and Drug Administration (FDA), *Xanthomonas campestris* is not.

Lactic acid bacteria (LAB) are classified GRAS, and have been used for centuries in fermented dairy products such as yogurt, cheese, and sour-cream. A characteristic of some LAB in food production processes is their production of exopolysaccharides (EPS). EPS provide improved viscosity and mouth-feel while also preventing syneresis (separation) in fermented food products. Despite their ability to produce EPS, LAB are not generally used as sources of thickening agents (either within a milk-based culture or as a source of exogenous EPS) because the EPS-positive phenotype is readily lost (Dierkesen et al., *J. Dairy Sci.* 80(8):1528-1536, 1997). The LAB strain described in this disclosure stably produces EPS when cultivated on appropriate media.

SUMMARY OF THE DISCLOSURE

A natural isolate of *Lactococcus lactis*, named "*Lactococcus lactis* subspecies *cremoris* Ropy 352," hereinafter referred to simply as "Ropy 352", has been isolated. This strain contains a plasmid (EPS plasmid) that encodes at least 13 active genes (FIG. 3). The enzymes encoded by these genes allow the bacteria to produce a previously unknown exopolysaccharide ("EPS 352"). Hence, in addition to providing EPS 352, the present invention also provides the nucleic acid sequences and the corresponding amino acid sequences of 13 of the open reading frames (ORFs; SEQ ID NO: 10) found on the EPS 352 plasmid.

EPS 352, when expressed in or added to milk or other liquids, imparts desirable sensory characteristics to the milk, including making the milk very thick, with a very smooth mouth-feel, and slightly sweet with an obvious "chewable-bite." Ropy 352 producing EPS, or EPS 352 alone may be added to any milk-based or non milk-based product, including any liquid food product, to produce these sensory characteristics. In the Ropy 352 strain, the biosynthesis of EPS 352 is controlled by genes carried outside the chromosome on a plasmid of about 32 kb ("EPS 352 plasmid"). Precedent predicts that the EPS 352 genes are linked in an operon like fashion. The EPS 352 plasmid has been isolated from the Ropy 352 organism, and the plasmid has been transformed into a plasmid free nonropy laboratory strain of *Lactococcus*, MG1363. (Gasson, *J. Bacteriol.* 154:1-9, 1983.) The plasmid encoded EPS 352 genes are expressed in the transformed strain, producing a ropy EPS, which imparts desirable sensory characteristics (as detailed below) to milk-based media.

One aspect of the invention provides the isolated *Lactococcus lactis* subspecies *cremoris* Ropy 352 organism (Ropy 352) as deposited under the rules of the Budapest Treaty, USDA-ARS-NCAUR-NRRL deposit number NRRL B-30229. Ropy 352 can be added to liquids (e.g., solids, semi-solids and gels) to cause thickening. Such thickening is desirable for use in creating products such as food products, beauty care products, and pharmaceuticals. Additionally, the Ropy 352 organism can be used to produce food products by fermentation of a food substrate with a culture of the Ropy 352 organism. Accordingly, the invention also provides the products made through the addition of the Ropy 352 culture.

Another aspect of the invention provides the purified exopolysaccharide EPS 352. EPS 352 can be added to liquids to produce food products as well as other products such as pharmaceuticals. Examples of such liquids include, liquid food substrates, such as milk-based liquids, soy-based liquids, fruit juice, and whey-based liquids. Accordingly the invention also provides the products made through the addition of EPS 352.

Yet another aspect of the invention provides the plasmid (contained in the deposited bacterial strain NRRL B-30229) that contains the open reading frames that encode the enzymes necessary for the production of EPS 352. This plasmid is approximately 32 kb in size. The identification of the plasmid allows for the production of EPS 352 by transgenic organisms that have been transformed with the EPS 352 plasmid. Furthermore, these transgenic organisms can be added to liquids to generate food products.

Another aspect of the invention provides methods of using the individual enzymes encoded by the EPS 352 plasmid for the production of modified exopolysaccharides. Used in these methods the enzymes derived from the nucleic acid sequence of the EPS 352 plasmid can be combined with other genes that code for exopolysaccharide biosynthetic pathways enzymes such that the exopolysaccharide produced is distinct from that of the disclosed EPS 352. Furthermore, these methods can be practiced in vitro or in vivo. (Stingele et al., *Mol. Microbiol.* 32(6):1287-1295, 1999; Kranenburg et al., *J. Bacteriol.* 181(11):6347-6453, 1999; Stingele et al., *J. Bacteriol.* 181(20):6354-6360, 1999; and Klerrebezem et al., *Antonie van Leewenhoek* 76:357-365, 1999).

Another aspect of the invention provides methods of using EPS 352 in various pharmaceutical formulations. Used in this context EPS 352 can be incorporated dry into pill formulations or into liquids to increase the viscosity of the formulation and facilitate delivery of the active ingredients.

Another aspect of the invention provides methods of using EPS 352 in various beauty products, such as hair shampoos, hair bleaching compositions, hair conditioners, hair gels and mousse, skin creams, nail varnishes, facial foundation, skin tanning gels, hair removers, shaving creams and in pill coatings, children's products (i.e., crayons, non-toxic glues), in addition to various industrial processes. (Hilger et al., *J. Environ. Eng.* 125(12):1113, 1999 and Shah et al., *Appl. Biochem. Biotech.* 82(2):81, 1999.)

SEQUENCE LISTING

The nucleic and amino acid sequences listed in the accompanying sequence listing are shown using standard letter abbreviations for nucleotide bases, and three-letter code for amino acids. Only one strand of each nucleic acid sequence is shown, but the complementary strand is understood to be included by any reference to the displayed strand.

SEQ ID NO: 1 shows the nucleic acid sequence of a portion of the EPS 352 plasmid.

SEQ ID NO: 2 shows the amino acid sequence of the enzyme designated "R" in FIG. 4, which is encoded by the nucleic acid sequence shown in SEQ ID NO: 1.

SEQ ID NO: 3 shows the amino acid sequence of the enzyme designated "X" in FIG. 4, which is encoded by the nucleic acid sequence shown in SEQ ID NO: 1.

SEQ ID NO: 4 shows the amino acid sequence of the enzyme designated "A" in FIG. 4, which is encoded by the nucleic acid sequence shown in SEQ ID NO: 1.

SEQ ID NO: 5 shows the amino acid sequence of the enzyme designated "B" in FIG. 4, which is encoded by the nucleic acid sequence shown in SEQ ID NO: 1.

SEQ ID NO: 6 shows the amino acid sequence of the enzyme designated "C" in FIG. 4, which is encoded by the nucleic acid sequence shown in SEQ ID NO: 1.

SEQ ID NO: 7 shows the amino acid sequence of the enzyme designated "D" in FIG. 4, which is encoded by the nucleic acid sequence shown in SEQ ID NO: 1.

SEQ ID NO: 8 shows the amino acid sequence of the enzyme designated "E" in FIG. 4, which is encoded by the nucleic acid sequence shown in SEQ ID NO: 1.

SEQ ID NO: 9 shows the amino acid sequence of the enzyme designated "O" in FIG. 4, which is encoded by the nucleic acid sequence shown in SEQ ID NO: 1.

SEQ ID NO: 10 shows the amino acid sequence of the enzyme designated "P" in FIG. 4, which is encoded by the nucleic acid sequence shown in SEQ ID NO: 1.

SEQ ID NO: 11 shows the amino acid sequence of the enzyme designated "F" in FIG. 4, which is encoded by the nucleic acid sequence shown in SEQ ID NO: 1.

SEQ ID NO: 12 shows the nucleic acid sequence encoding Eps "M" and Eps "N."

SEQ ID NO: 13 shows the amino acid sequence of the enzyme designated "M" in FIG. 4, which is encoded by the nucleic acid sequence shown in SEQ ID NO: 12.

SEQ ID NO: 14 shows the amino acid sequence of the enzyme designated "N" in FIG. 4, which is encoded by the nucleic acid sequence shown in SEQ ID NO: 12.

SEQ ID NO: 15 shows the nucleic acid sequence encoding the enzyme designated "U."

SEQ ID NO: 16 shows the amino acid sequence of Eps "U," which is encoded by SEQ ID NO: 15.

SEQ ID NO: 17 shows the amino acid sequence of EpsG that is involved in eps biosynthesis in *Lactococcus lactis* NIZOB40.

BRIEF DESCRIPTION OF THE DRAWINGS

FIGS. 2 A-C shows double stranded sequence data from the EPS 352 plasmid (SEQ ID NO: 12) and the corresponding amino acid sequences named EpsM (SEQ ID NO: 13) and EpsN (SEQ ID NO: 14). The insertion site of the ISS1 element is indicated in EspN and which confers a non-ropy phenotype in Ropy 352, thus linking these two open reading frames to EPS 352 expression.

FIG. 3A shows the alignments of the ORF designated "N" in FIG. 4 (SEQ ID NO: 14) and the ORF designated "M" in FIG. 4 (SEQ ID NO: 13) to each other.

FIG. 3B shows the jalignments of the ORF designated "N" in FIG. 4 (SEQ ID NO: 14) and the ORF designated "M" in FIG. 4 (SEQ. NO: 13) to each other as well as to an enzyme (EpsG; SEQ ID NO: 17) involved in eps biosynthesis in *Lactococcus lactis* NIZO_B40. The overall identity between ORF "M" and EpsG is 24% and between ORF "N" and EpsG is 25%.

Figure 5B:
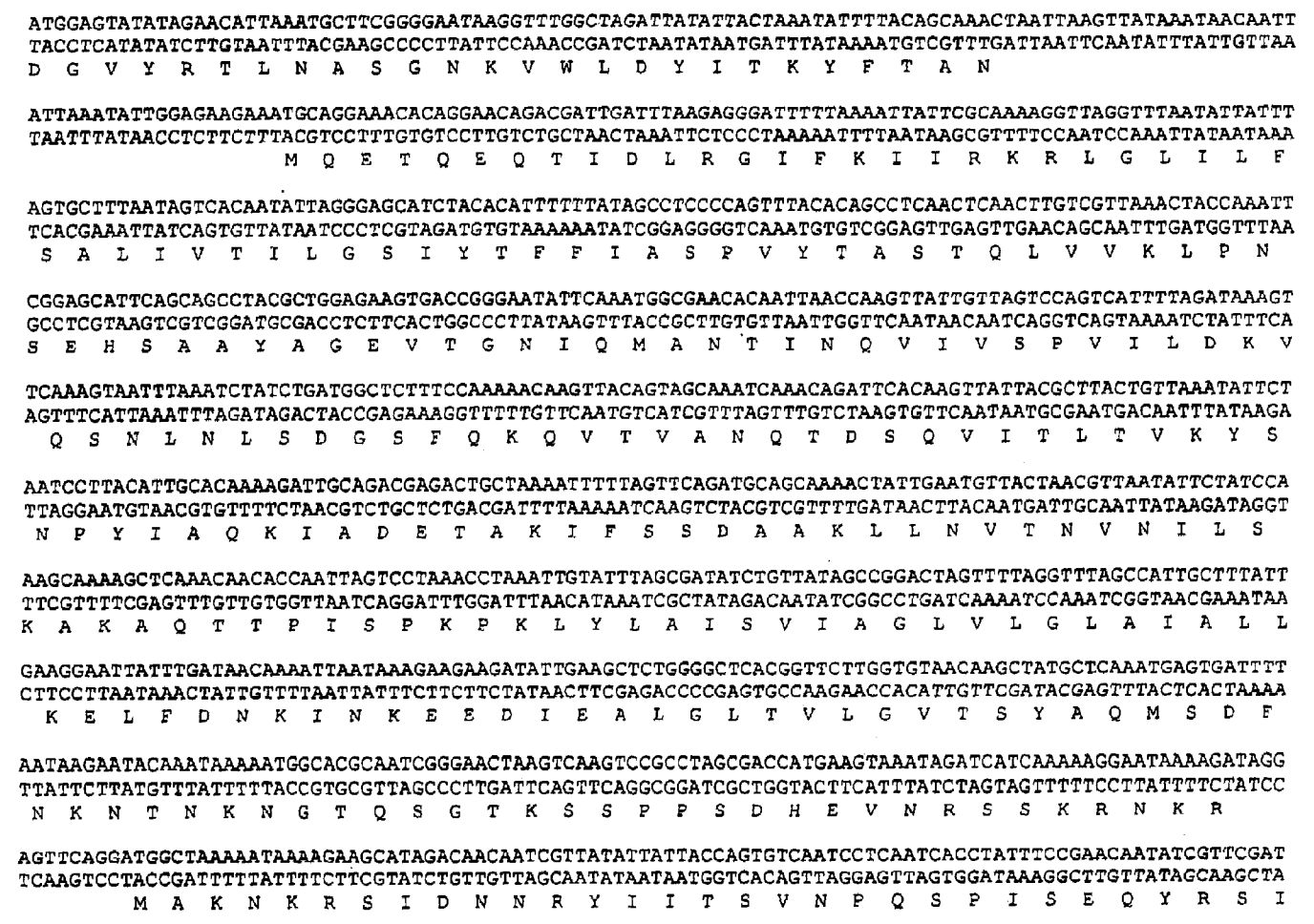
Figure 5C:
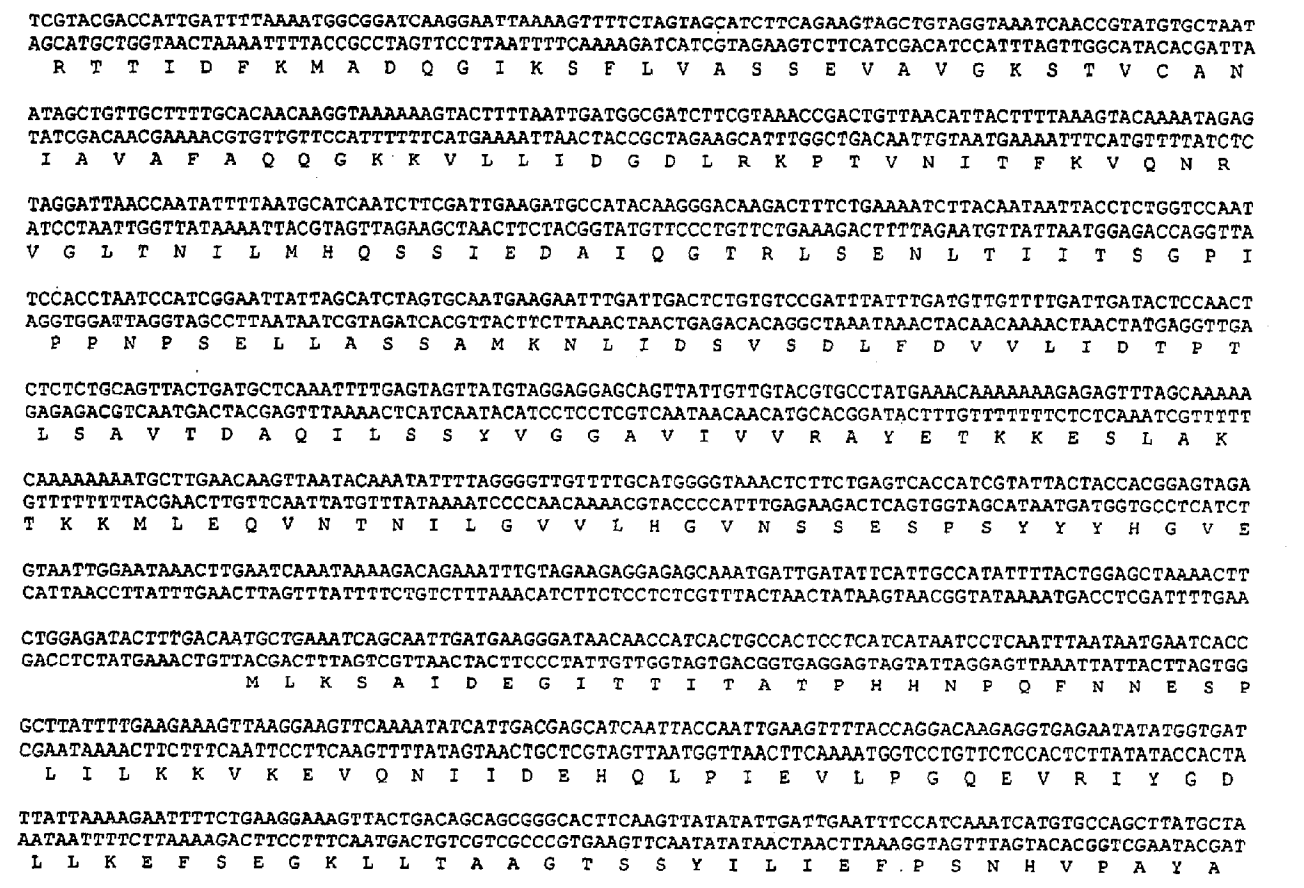
Figure 5D:
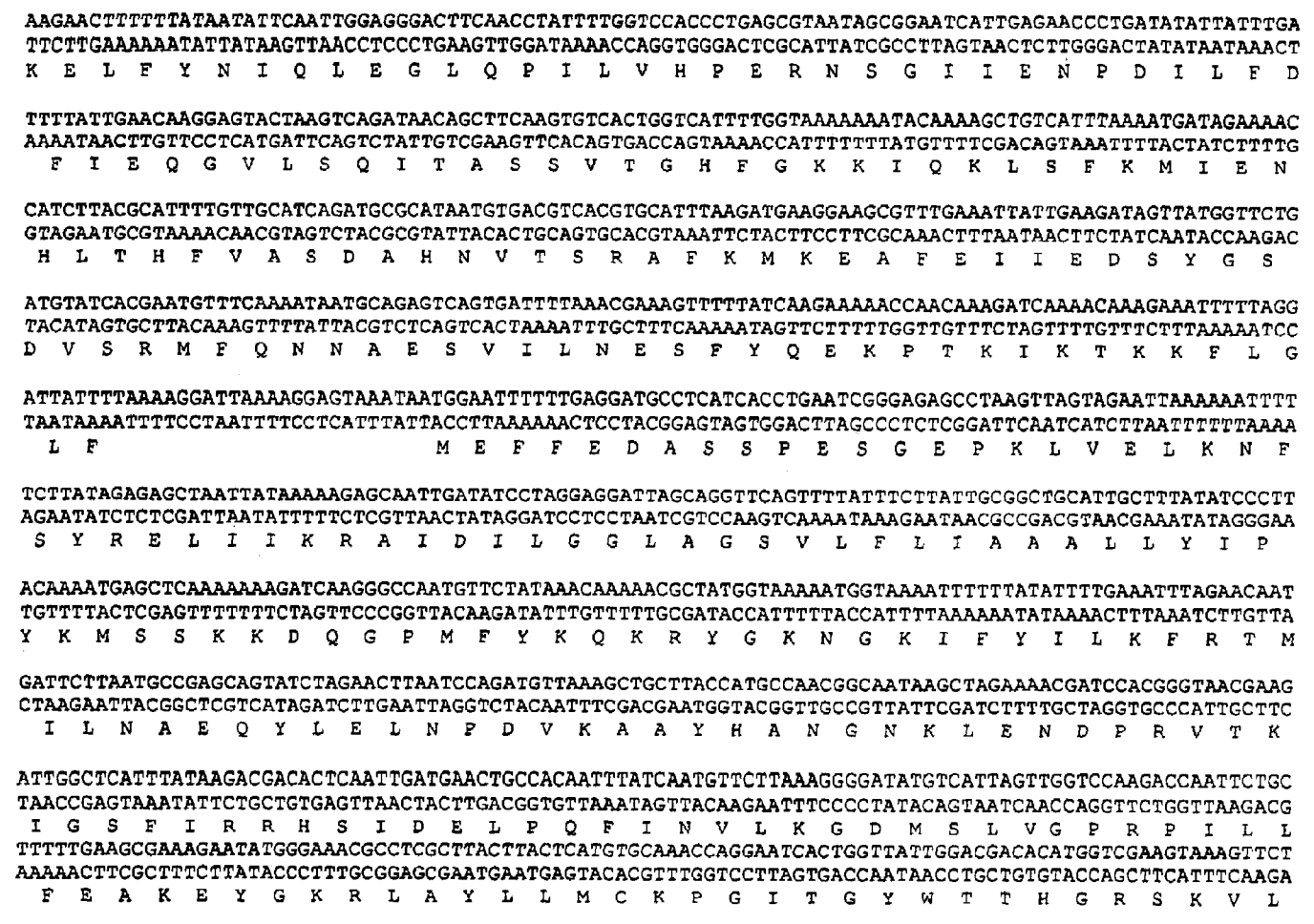

FIGS. 5 A-G shows the DNA and amino acid sequence of the entire EPS operon from upstream of the promoter to downstream of the terminator (SEQ ID NO: 1, and the corresponding complementary strand). This sequence is 6850 bp in length. The starts of the open reading frames are labeled with the gene name (corresponding to FIG. 4) printed in the right margin.

FIG. 6 shows the nucleic acid sequence of Eps U (SEQ ID NO: 15). The start and stop codons are underlined.

DETAILED DESCRIPTION

Definitions and Abbreviations

Figure 1:
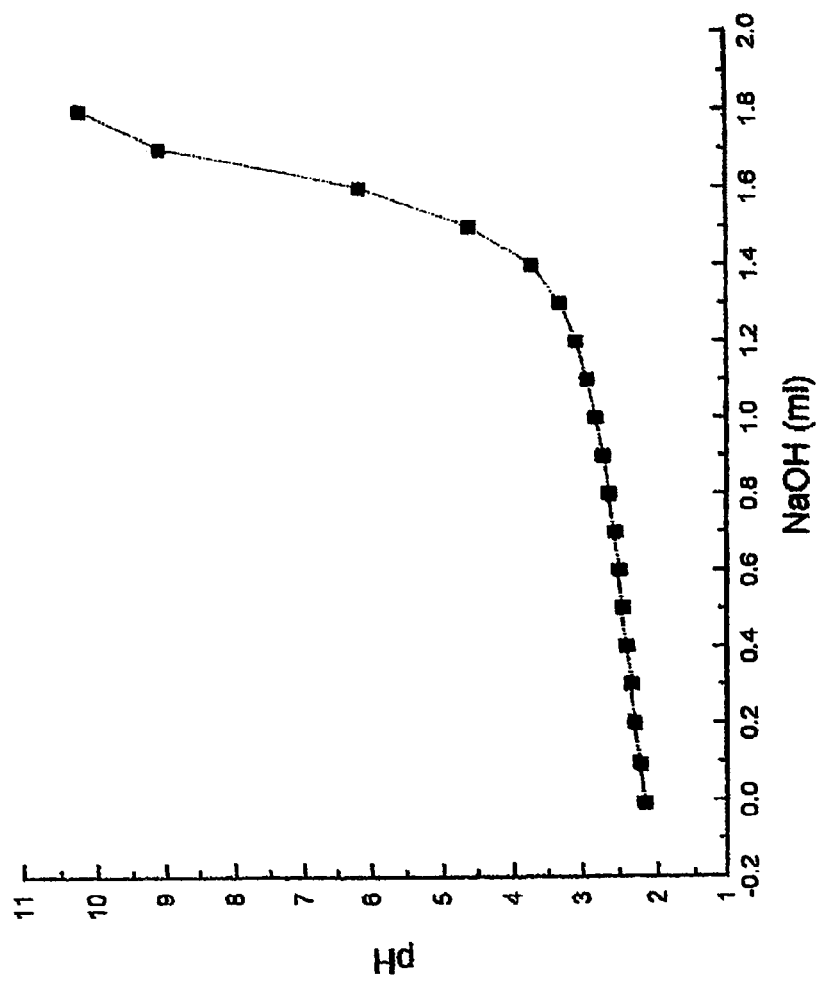
FIG. 1 describes the degree of phosphate protonation. As sodium hydroxide is added to the polysaccharide solution, there is only one inflection in the titration profiles, indicating that the phosphate group in the EPS 352 is in the form of a phosphodiester linkage rather than as the monoester, which would have shown 2 inflection points.

Unless otherwise noted, technical terms are used according to conventional usage. Definitions of common terms in molecular biology may be found in Benjamin Lewin, *Genes VII*, Oxford University Press, 1999 (ISBN 0-19-879276-X); Kendrew et al. (eds.), *The Encyclopedia of Molecular Biology* Blackwell Science Ltd., 1994 (ISBN 0-02192-9); and Robert A. Meyers (ed.), *Molecular Biology and Biotechnology: a Comprehensive Desk Reference*, VCH Publishers, Inc., 1995 (ISBN 1-56081-569-8).

W/V means weight per unit volume.
kDa means kilodaltons.
MWCO means molecular weight cutoff
TCA means trichloroacetic acid.
Mol % means molar percent
mPA-s means millipascals
n.d. means none detected.

*Lactococcus lactis* subspecies *cremoris* Ropy 352 ("Ropy 352") is the organism deposited under the Budapest Treaty as USDA-ARS-NCAUR-NRRL deposit number NRRL B-30229. Ropy 352 has the characteristic property of producing the exopolysaccharide EPS 352 under suitable growth conditions, e.g., streaked onto whey agar or defined lactococcal medium containing glucose agar plates and incubated at 30° C.

EPS 352 is an exopolysaccharide that is produced by Ropy 352 and that has the following characteristics:

| Composition: | |
|---|---|
| Glucose: | range of 54% to 58% |
| Galactose: | range of 42% to 46% |
| Charged: | Yes |
| Molecular weight: | range of 800,000 to 8,000,000 (average of 1,600,000) |
| Phosphorous: | Present in backbone or sidechain |
| Structure: | |
| Endpoints: | galactose; |
| Branchpoints: | glucose |

Several gene products are required for EPS 352 biosynthesis. The EPS biosynthetic genes are located extrachromasomally on the EPS 352 plasmid. Precedent indicates that these genes are organized in an operon like fashion.

EPS 352 plasmid is an extrachromosomal plasmid of approximately 32 kb in size that carries the EPS 352 biosynthetic genes. Current methods used to estimate plasmid size are not exact. For instance, the perceived size of a plasmid may be effected by the degree of relaxation of the plasmid and the degree to which proteins may be associated with the plasmid. Thus, the EPS 352 plasmid is believed to be about 32 kb in size, and may be, for example, from 30 to 38 kb in size. Several research groups have linked EPS biosynthesis with plasmids of various sizes: 6.8 kb, 25.8 kb, 28 kb, 40.2 kb, and 45.5 kb (Vescovo et al., *Biotech. Letters II* 10:709-712, 1989; Neve et al., *Biochimie* 70:437-442, 1988; Vedamuthu et al., *Appl. Environ. Microbiol.* 51:677-682, 1986; Kranenburg et al. *Mol. Microbiol.* 24:387-397, 1997; and Von Wright et al., *Appl. Environ. Microbiol.* 53:1385-1386, 1987).

Food means any eatable or drinkable substance consumed by humans or animals, e.g., milk, cream, dairy products, soy products, fruit juice, vegetable juices, ice cream, soups, etc.

Food Product means any food that is produced by altering its original state, e.g., milk to which has been added EPS 352.

Milk is used broadly herein to include all dairy products regardless of fat content or lactose content. The term as used herein also includes substances commonly used in place of milk, such as soy used as "soy milk". The term also includes milk products from animals other than cows, including goat milk.

Liquid as used herein includes fluids with varying degrees of fluidity including highly fluid liquids such as non-fat milk, thicker liquids such as full fat milk and cream, semi-solid substances, and gels such as yogurt and other fermented milk products. A liquid may be altered from its original state to produce an altered liquid, e.g., an adhesive solution, a paint emulsion, a lubricant, or a fruit juice to which EPS 352 has been added.

A Milk-Based liquid is any liquid wherein milk forms an appreciable percentage of the total volume of the liquid. For example, a liquid having 0.10% or more of milk solids.

A Soy-Based liquid is any liquid wherein soy forms an appreciable percentage of the total volume of the liquid. For example, a liquid having 0.10% or more of soy solids To Thicken means to decrease fluidity and increase viscosity.

Thickener means any substance used to thicken, including, for instance, exopolysaccharides. A thickener may be produced by organisms cultured within a medium or may be added exogenously to a medium.

Mouth-feel is a term of art used in the food industry to describe sensory characteristics of a food. It has the same meaning as the word "texture" which has been previously defined as "the composite of the structural elements of the food and the manner in which it registers with the physiological sense" (Szczesniak, *J. Food Science* 28:385-389, 1963), or "the composite of those properties which arise from the physical structural elements and the manner in which it registers with the physiological senses" (Sherman, *J. Food Science* 27:381-385, 1970).

Pharmaceutical a chemical compound or composition capable of inducing a desired therapeutic or prophylactic effect when properly administered to a subject.

Beauty care product is an externally applied product that is intended to alter the appearance of the subject to which it has been applied.

Coating agent an agent applied to the exterior surface of an object. A coating agent generally forms a thin layer on the surface of the object.

Transformed refers to a cell into which a nucleic acid molecule has been introduced by molecular biology techniques. The term encompasses all techniques by which a nucleic acid molecule might be introduced into such a cell, including transformation with plasmid vectors, transfection with viral vectors, and introduction of naked DNA by electroporation, lipofection, and particle gun acceleration.

Purified does not require absolute purity; rather, it is intended as a relative term. Thus, for example, a purified polysaccharide preparation is one in which the subject polysaccharide is more pure than in its natural environment within a cell or within a cell culture medium. Generally, a polysaccharide preparation is purified such that the polysaccharide represents at least 50% of the total polysaccharide content of the preparation.

Isolated an isolated nucleic acid has been substantially separated or purified away from other nucleic acid sequences in the cell of the organism in which the nucleic acid naturally occurs, i.e., other chromosomal and extrachromosomal DNA and RNA. The term "isolated" thus encompasses nucleic acids purified by standard nucleic acid purification methods. The term also embraces nucleic acids prepared by recombinant expression in a host cell, as well as chemically synthesized nucleic acids.

ORF is an open reading frame. An ORF is a contiguous series of nucleotide triplets coding for amino acids. These sequences are usually translatable into a peptide.

Operably linked means a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

Probe is an isolated nucleic acid attached to a detectable label or reporter molecule. Typical labels include radioactive isotopes, ligands, chemiluminescent agents, and enzymes.

Target Nucleic Acid is a nucleic acid that hybridizes with a probe. The conditions under which hybridization occurs may vary with the size and sequence of the probe and the target sequence.

By way of illustration, only a hybridization experiment may be performed by hybridization of a DNA probe (for example, a probe derived from the EPS 352 plasmid labeled with a chemiluminescent agent) to a target DNA molecule which has been electrophoresed in an agarose gel and transferred to a nitrocellulose membrane by Southern blotting (a technique well known in the art and described in Sambrook et al., *Molecular Cloning: A Laboratory Manual*, 2nd ed., vols. 1-3, Cold Spring Harbor, N.Y., 1989).

Hybridization with a radio-labeled probe is generally carried out in a solution of high ionic strength such as 6×SSC at a temperature that is 20° C.-25° C. below the melting temperature, $T_m$, described below. For such Southern hybridization experiments where the target DNA molecule on the Southern blot contains 10 ng of DNA or more, hybridization is typically carried out for 6-8 hours using 1-2 ng/mL radiolabeled probe. Following hybridization, the nitrocellulose filter is washed to remove background hybridization. The wash conditions should be as stringent as possible to remove background hybridization but to retain a specific hybridization signal. The term $T_m$ represents the temperature above which, under the prevailing ionic conditions, the radiolabeled probe molecule will not hybridize to its target DNA molecule. The $T_m$ of such a hybrid molecule may be estimated from the following equation:

$$T_m = 81.5° C. - 16.6(\log_{10}[Na^+]) + 0.41(\% \ G+C) - 0.63(\% \ \text{formamide}) - (600/1)$$

Where 1=the length of the hybrid in base pairs. This equation is valid for concentrations of $Na^+$ in the range of 0.01M to 0.4M, and it is less accurate for calculations of $T_m$ in solutions of higher $[Na^+]$. The equation is primarily valid for DNAs whose G+C content is in the range of 30% to 75%, and applies to hybrids greater than 100 nucleotides in length (the behavior of oligonucleotide probes is described in detail in Ch. 11 of Sambrook et al., 1989).

Generally hybridization wash conditions are classified into categories, for example very high stringency, high stringency, and low stringency. The conditions corresponding to these categories are provided below.

| Very High Stringency (detects sequences that share 90% sequence identity) | | | | |
|---|---|---|---|---|
| Hybridization in | 5× | SSC at | 65° C. | 16 hours |
| Wash twice in | 2× | SSC at | Room temp. | 15 minutes each |
| Wash twice in | 0.2× | SSC at | 65° C. | 20 minutes each |

| High Stringency (detects sequences that share 80% sequence identity or greater) | | | | |
|---|---|---|---|---|
| Hybridization in | 3× | SSC at | 65° C. | 16 hours |
| Wash twice in | 2× | SSC at | Room temp. | 15 minutes each |
| Wash twice in | 0.5× | SSC at | 55° C. | 20 minutes each |

| Low Stringency (detects sequences that share greater than 50% sequence identity) | | | | |
|---|---|---|---|---|
| Hybridization in | 3× | SSC at | 65° C. | 16 hours |
| Wash twice in | 2× | SSC at | Room temp. | 20 minutes |

The above example is given entirely by way of theoretical illustration. One skilled in the art will appreciate that other hybridization techniques may be utilized and that variations in experimental conditions will necessitate alternative calculations for stringency.

Conservative amino acid substitutions are those substitutions that, when made, least interfere with the properties of the original protein, i.e., the structure and especially the function of the protein is conserved and not significantly changed by such substitutions. The table below shows amino acids that may be substituted for an original amino acid in a protein and that are regarded as conservative substitutions.

TABLE 1

| Original Residue | Conservative Substitutions |
|---|---|
| ala | ser |
| arg | lys |
| asn | gln; his |
| asp | glu |
| cys | ser |
| gln | asn |
| glu | asp |
| gly | pro |
| his | asn; gln |
| ile | leu; val |
| leu | ile; val |
| lys | arg; gln; glu |
| met | leu; ile |
| phe | met; leu; tyr |
| ser | thr |
| thr | ser |
| trp | tyr |
| tyr | trp; phe |
| val | ile; leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative. For instance, changes in which (a) a hydrophilic residue, e.g., seryl or threonyl, is substituted for (or by) a hydrophobic residue, e.g., leucyl, isoleucyl, phenylaianyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine.

Primers are short nucleic acids, preferably DNA oligonucleotides 10 nucleotides or more in length, which are annealed to a complementary target DNA strand by nucleic acid hybridization to form a hybrid between the primer and the target DNA strand, then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Probes and primers as used in the present invention typically comprise at least 15 contiguous nucleotides of a known sequence. In order to enhance specificity, longer probes and primers may also be employed, such as probes and primers that comprise at least 20, 30, 40, 50, 60, 70, 80, 90, 100, or 150 consecutive nucleotides of the disclosed nucleic acid sequences.

Methods for preparing and using probes and primers are described in the references, for example Sambrook et al., *Molecular Cloning: A Laboratory Manual*, $2^{nd}$ ed., vol. 1-3, Cold Spring Harbor, N.Y., 1989; Ausubel et al., *Current Protocols in Molecular Biology*, Greene Publ. Assoc. & Wiley-Intersciences, 1987; Innis et al., *PCR Protocols, A Guide to Methods and Applications*, 1990. PCR primer pairs can be derived from a known sequence, for example, by using computer programs intended for that purpose such as *Primer* (Version 0.5, 1991, Whitehead Institute for Biomedical Research, Cambridge, Mass.).

Recombinant nucleic acid is a sequence that is not naturally occurring or has a sequence that is made by an artificial combination of two otherwise separated segments of sequence. This artificial combination is often accomplished by chemical synthesis or, more conmmonly, by the artificial manipulation of isolated segments of nucleic acids, e.g., by genetic engineering techniques such as those described in Sambrook et al. (1989). The term recombinant includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector, used to transform a cell.

Sequence identity: The similarity between two nucleic acid sequences or between two amino acid sequences is expressed in terms of the level of sequence identity shared between the sequences. Sequence identity is typically expressed in terms of percentage identity; the higher the percentage, the more similar the two sequences.

Methods for aligning sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene* 73:237-244, 1988; Higgins & Sharp, *CABIOS* 5:151-153, 1989; Corpet et al., *Nucleic Acids Research* 16:10881-10890, 1988; Huang, et al., *CABIOS* 8:155-165, 1992; and Pearson et al., *Methods in Molecular Biology* 24:307-331, 1994. Altschul et al., *J. Mol. Biol.* 215:403-410, 1990, presents a detailed consideration of sequence alignment methods and homology calculations.

The NCBI Basic Local Alignment Search Tool (BLAST™) (Altschul et al., *J. Mol. Biol.* 215:403-410, 1990 is available from several sources, including the National Center for Biotechnology Information (NBCI, Bethesda, Md.) and on the Internet, for use in connection with the sequence analysis programs blastp, blastn, blastx, tblastn and tblastx. BLAST™ can be accessed on the interned at NBCI website. A description of how to determine sequence identity using this program is available at the web site. As used herein, sequence identity is commonly determined with the BLAST™ software set to default parameters. For instance, blastn (version 2.0) software may be used to determine sequence identity between two nucleic acid sequences using default parameters (expect=10, matrix=BLOSUM62, filter=DUST (Tatusov and Lipmann, in preparation as of Dec. 1, 1999; and Hancock and Armstrong, *Comput. Appl. Biosci.* 10:67-70, 1994), gap existence cost=11, per residue gap cost=1, and lambda ratio=0.85). For comparison of two polypeptides, blastp (version 2.0) software may be used with default parameters (expect 10, filter=SEG (Wootton and Federhen, *Computers in Chemistry* 17:149-163, 1993), matrix=BLOSUM62, gap existence cost=11, per residue gap cost=1, lambda=0.85).

For comparisons of amino acid sequences of greater than about 30 amino acids, the "Blast 2 sequences" function of the BLAST™ program is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 45%, at least 50%, at least 60%, at least 80%, at least 85%, at least 90%, or at least 95% sequence identity.

Methods

General Methods

The present invention utilizes standard laboratory practices for the cloning, manipulation and sequencing of nucleic acids, purification and analysis of proteins and other molecular biological and biochemical techniques, unless otherwise stipulated. Such techniques are explained in detail in standard laboratory manuals such as Sambrook et al., *Molecular Cloning: A Laboratory Manual*, $2^{nd}$ ed., vol. 1-3, Cold Spring Harbor, N.Y., 1989; and Ausubel et al., Current Protocols in Molecular Biology, Greene Publ. Assoc. & Wiley-Intersciences, 1989. Other techniques specific to Lactococcus are discussed in the inventors' publications including: Dierksen et al., *Genetics of Streptococci, Enterococci and Lactcocci*, (Ferretti et al., eds.), 1995; Basel, *Dev. Biol. Stand* 585:469-480, 1995; Dierksen et al., *J. Dairy Sci.*, 80(8):1528-1536, 1997; and Knoshaug et al., *J. Dairy Sci.* 83:633-640, 2000.

1. Growth and Characterization of the Ropy 352 organism.

The EPS 352 producing organism, *Lactococcus lactis* subspecies *cremoris* Ropy 352, was isolated, classified and deposited under the Budapest Convention as USDA-ARS-NCAUR-NRRL deposit number NRRL B-30229. Ropy 352 may be obtained on demand from the USDA-ARS-NCAUR-NRRL at Agricultural Research Service Culture Collection (NRRL), National Center for Agricultural Utilization Research (NCAUR), Agricultural Research Service (ARS), U.S. Department of Agriculture (USDA), 1815 North University Street, Peoria, Ill. 61604 U.S.A. Ropy 352 was streaked onto whey agar or defined lactococcal media containing glucose (DLMG) agar. Whey agar (Vedarnuthu et al., *Appl. Microbiol.* 51:677-682, 1986) made as previously described with the following modifications: yeast extract (5 g, Difco Laboratories, Detroit, Mich.) and sodium β-glycerophosphate (19 g, Sigma Chemical Co., St. Louis, Mo.) were added to the centrifuged supernatant and the volume brought up to 600 mL. The second part of the media consisted of 15 g of agar and 3 drops of antifoam A (Sigma) in 400 mL of water. Both portions were autoclaved for 12 min, removed promptly, cooled to 50° C., mixed, and poured into sterile petri plates. DLMG agar (Molenaar et al., *J. Bacteriol.* 175:5438-5444, 1993.) was prepared as two parts; part one consisted of the base media which was prepared in 758 mL of water, heated to dissolve the components, mixed with 10 mL of the metals, vitamins, and nucleic acid solutions and 12 mL of 20% glucose or lactose solution, filter sterilized, and heated to 55° C. in a water bath. Part two consisted of 10 g of agar and 2 drops of antifoam A (Sigma) which were mixed into 200 mL of water, autoclaved, and cooled to 55° C. Part one was mixed into part two and poured into sterile petri plates. Ropy 352 was streaked onto plates and incubated at 30° C. to produce macroscopic, individual, EPS 352 producing colonies of Ropy 352 (procedure described in inventors' publications listed above).

The EPS 352 may be recognized by the formation of viscous ropes greater than five mm in length originating from a whey agar or DLMG agar. Whey agar plates were incubated at 30° C. for 48 h. Characteristic ropy phenotype is apparent from viscous rope greater than 5 mm formed when a colony is touched with a sterile toothpick. These ropes became visible when the colony was touched with a sterile toothpick and the toothpick was drawn away from the colony, thus, stretching the EPS 352 out. An additional way to recognize EPS 352 is by the formation of viscous ropes in liquid milk inoculated with Ropy 352 organism. Liquid milk was sterilized by steaming for 30 min and 10 mL of milk were inoculated with 0.5 mL of an overnight Ropy 352 culture. The milk was incubated for 18 hours at 30° C. and visually examined for ropy EPS expression. These viscous ropes were visualized by touching the milk with a toothpick and drawing the toothpick away from the milk.

2. Purification and Characterization of EPS 352.

An individual EPS 352 producing Ropy 352 colony from a whey agar plate was picked and used to inoculate 1 L of polysaccharide production medium in a 2.8 L Fernbach flask. The medium was cultured at 30° C. for 16 to 20 hours without shaking. The polysaccharide production medium consisted of 10% w/v nonfat milk in water, which was prepared by stirring 100 g dry milk powder into 1 L deionized water at room temperature for 1 hour and then sterilizing the mixture in an autoclave for 12 minutes at 120° C.

Ropy 352 culture broths were transferred to 500 mL centrifuge bottles and insoluble fractions were pelleted at 10 K×g for 20 minutes. Clarified supernatants were dialyzed (6-8 kDa MWCO, Spectra/Por 1; Spectrum Laboratories, Inc., Laguna Hills, Calif.) against water containing 0.02% sodium azide for at least 24 hours.

An equal volume of absolute ethanol was added to the contents of the dialysis tubing and stirred in an ice bath. Ropy 352 cultures formed a precipitate of elongated ropes that were collected by centrifugation as described above. This was termed the Ropy fraction and contained EPS 352.

From 1 L of 10% nonfat milk medium, 34 mg of total polysaccharide was recovered from Ropy 352 cultures after centrifugation and dialysis. The polysaccharide responsible for the ropy characteristic (EPS 352) was purified by precipitation with 50% ethanol, followed by trichloroacetic acid (TCA) removal of residual protein. This Ropy fraction contained 10 mg of polysaccharide and was essentially protein free (<20 µg/mg in the final product). The Ropy fraction also contained 2.3 µg phosphorus/mg polysaccharide.

Compositional analysis of EPS 352 revealed a repeating structure composed of approximately 54% to 58% glucose, and 42% to 46% galactose. Compositional data suggests a novel structure for EPS 352 with glucose as the branch residue and galactose located at the end points.

The predominant sugar found in EPS 352, at 36 mol %, is (1,4)-linked glucose. The only sugar found as terminal non-reducing end groups (i.e., had a single linkage position) was galactose at 27 mol %; this quantity is indicative of a highly branched structure. A (1,4,6)-linked glucose reside was found at a concentration of 21 mol %; the three linkage sites indicate that it is a branch point in this structure. The least represented sugar was the (1,4)-linked galactose, which occurred at a concentration of 15 mol %. Results from this analysis are listed in Table 2:

TABLE 2

Identification of permethylated PAAN (Peracetylated aldononitrile) derivatives from Ropy 352 and Ropy polysaccharides

| PAAN methyl sugar | Linkage site | Ropy fraction from Ropy 352 (mol %) |
| --- | --- | --- |
| 2,3,4,6-tetra-O-methyl galactose | 1 | 27 |
| 2,3,6-tri-O-methyl galactose | 1, 4 | 15 |
| 2,4,6-tri-O-methyl galactose | 1, 6 | n.d. (none detected) |
| 2,3,4-tri-O-methyl galactose | 1, 6 | n.d. |
| 2,3,6-tri-O-methyl glucose | 1, 4 | 36 |
| 2,3,4-tri-O-methyl glucose | 1, 6 | n.d. |
| 3,4,6-tri-O-methyl mannose | 1, 2 | n.d. |
| 2,3-di-O-methyl glucose | 1, 4, 6 | 21 |
| 3,4-di-O-methyl glucose | 1, 2, 6 | n.d. |
| 2,4-di-O-methyl mannose | 1, 3, 6 | n.d. |

The degree of phosphate protonation is shown in FIG. 1. As sodium hydroxide was added to the polysaccharide solution, there was only one inflection in the titration profiles, indicating that the phosphate group in the Ropy fraction polysaccharides is in the form of a phosphodiester linkage rather than as the monoester, which would have shown 2 inflection points.

3. Viscosity of Milk Culture During 25 hour Fermentation With Ropy 352.

1 L of milk was inoculated with a single whey agar-grown colony of Ropy 352. Viscosity was measured with a Brookfield model LVTDV-I digital viscometer (Stoughton, Mass.) using a LV1 spindle.

The viscosity of the Ropy 352 culture reached a value of 44000 mPA-s at 24 hours, compared to an initial viscosity of 1 mPa-s (see Table 3). This data verifies the phenotypic observation that Ropy 352 culture thickens a liquid food product (milk).

TABLE 3

Viscosity change (in mPa-s) after 24 h.

| Strain | Sample | 0 h | 24 h |
|---|---|---|---|
| Ropy 352 | Fermented milk | 1.0 | 44000 |
| No cells | Milk | 1.0 | 1.0 |

4. Isolation and Characterization of the Biosynthetic EPS 352 Plasmid.

Figure 2B:
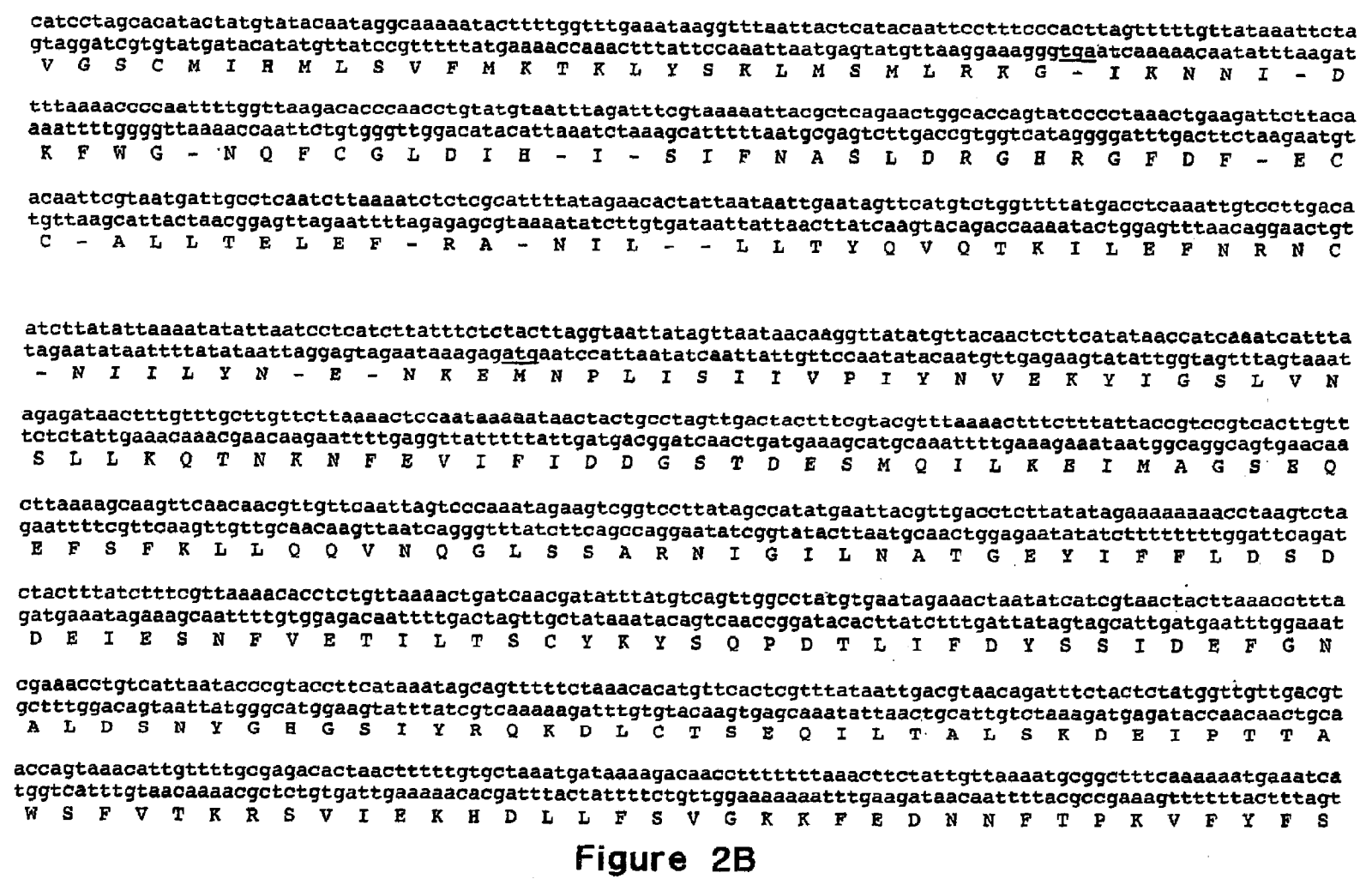
Figure 4:
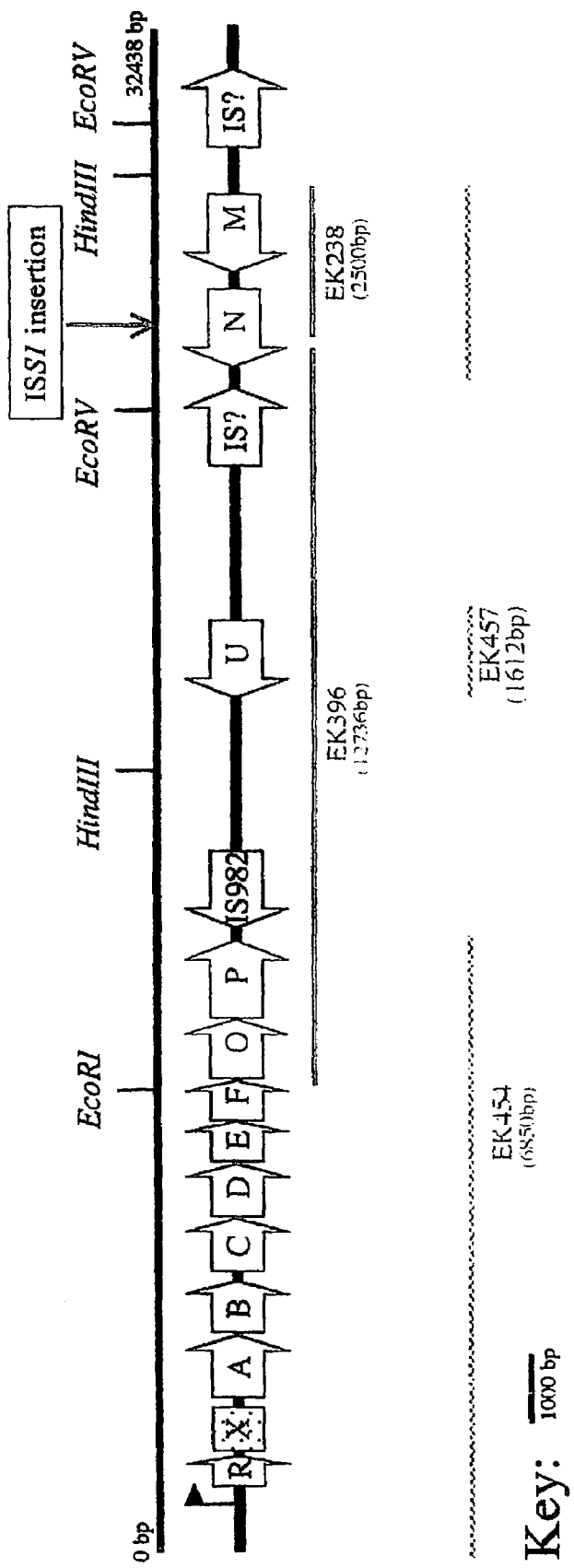
FIG. 4 is a diagram of the organization of the genes on the EPS 352 plasmid. The large arrows with letters inside represent genes and their orientation. The square with the letter X is a non-functional gene as it is missing its beginning (5' prime sequence). Eps ORFs are designated M, N, O, and P. The site of the ISS1 insertion, which disrupted EPS 352 production, is indicated by an downward pointing arrow that points to a position in Eps N.

The EPS 352 plasmid is a plasmid of about 32 kb in size that may be isolated from Ropy 352. A 2.2 KB fragment from the EPS 352 plasmid (FIG. 2) and a 6.85 kb fragment (FIG. 4) have been sequenced. These sequences encodes ORFs M and N which show homology to a class of sugar transfer enzymes (glycosyltransferases) known to be involved in EPS biosynthesis (FIG. 2). Several restriction endonucleases cut this plasmid, including EcoRI, EcoRV, HindIII, SacI, SphI, DraI, HincII, NdeI, Sau3AI, and SpeI.

The EPS 352 plasmid contains all biosynthetic genes coding for the enzymes needed to make EPS 352. This was demonstrated by the following experiment. The EPS 352 plasmid, containing an erythromycin resistant encoded insertion element for selection, was isolated from a culture of Ropy 352 using DNA preparation methods as described in Knoshaug et al., *J. Dairy Science* 83:633-640, 2000. (Ref for plasmid DNA isolation: O'Sullivan et al., *Appl Environ Microbiol.* 59:2730-2733, 1993). This DNA was used to transform a plasmid-free nonropy lactococcal strain, MG1363 by electroporation as described (Dornan et al., *Lett. Appl. Microbiol.* 11:62-64, 1990; Holo et al., *Appl. Environ. Microbiol.* 55:3119-3123, 1989). Cells were grown for 24 hours in M17-glucose media supplemented with 0.3 M sucrose and 2% (MG1363) or 0.5% (Ropy352) glycine. Cells were pelleted, washed in cold 0.3 M sucrose three times, and resuspended in 200 µl of 0.3 cold M sucrose. DNA was added to the cells and the mixture was transferred to a chilled electroporation cuvette (0.2 cm gap). The cells were shocked (2.5 kV, 200 ohms, 25 µF) and resuspended in 8 mL of growth media supplemented with 0.3 M sucrose and 50 ng/mL em. Cells were allowed to recover for 1.5 hours before plating on whey agar containing 2 µg/mL em. Erythromycin resistant transformants were selected, and then screened for the ropy EPS 352 phenotype. MG1363 containing the EPS 352 plasmid was analyzed by Southern blot to verify the presence of the plasmid. The probe used was 1.6 kb long and specific to the Ropy 352 EPS ORF M and ORF N genes. Results demonstrated that the probe reacted with a 32 kb plasmid in Ropy352 (un-nicked and nicked forms) and with a 37 kb plasmid in EK356 (EPS 352 plasmid containing a 5.4 kb erythromycin resistant encoded insertion element for selection; un-nicked and nicked forms).

The southern blot analysis was additionally confirmed by testing the transformed bacteria for the Ropy phenotype. Results showed that the phenotypic carried over to the MG1363 strain.

5. Production of Food Products by Adding EPS 352 to a Food Substrate.

EPS 352 can be added to a liquid food substrate to increase viscosity and thickness of the liquid and to enhance texture and mouth-feel. Liquid food substrates may include, but are not limited to: milk (including low-fat and non-fat milk), milk-based liquids, whey-based liquids, soy-based liquids, fruit-juices, and oil-based liquids and emulsions. EPS 352 can be used to enhance the thickness and texture of, for example, yogurt, milk-shakes, fruit-juices, soy drinks, Scandinavian fermented milk products (e.g., "villi, "langfil," and "filmjolk,"), bakery fillings, dressings, sauces and gravies. EPS 352 can also be added to solid or semi-solid food substrates to enhance the texture of, for instance, frozen foods, canned foods and cheeses. Thickness of the liquid food substrate will increase in proportion to the amount of EPS 352 added. EPS 352 may be added to any liquid food substrate in an amount necessary to produce the desired consistency. Determining an amount necessary to produce a desired consistency is a simple matter of empirical experimentation.

A specific example of a food product made using EPS 352 is a thickened, non-fermented food product that has the qualities of yogurt, but without the need for fermentation. Milk (e.g., non-fat milk) can be used as a liquid food substrate to which an amount of EPS 352 can be added, sufficient to cause thickening to a desired consistency. EPS 352 may be supplied in the form of an essentially pure powder and added directly to the milk. The powder may be mixed into the milk at room temperature using conventional methods and the mixture may then be aliquoted into sealed containers and pasteurized. Such a product would be low in fat, have a yogurt-like consistency, and would not require fermentation, a step which is time-consuming, expensive and prone to microbial contamination.

6. Production of Milk-Derived Fermented Food Products by Adding a Pure Culture of the Ropy 352 Organism to a Food Substrate and Fermenting the Mixture.

Ropy 352 can be used to produce fermented food products such as yogurt (and other products as listed above). Such products are described as probiotic (this refers to organisms who are ingested, such as the LAB, which contribute to the health and balance of the human's intestinal tract thus possibly protecting against disease and improving nutrition). During fermentation, Ropy 352 produces the EPS 352 exopolysaccharide which imparts desirable qualities to certain foods. In particular, EPS 352 gives fermented milk products a very smooth, rich mouth-feel with a slightly sweet flavor.

A specific example of a fermented food product made using Ropy 352 is yogurt. Milk (e.g., either whole, 2% or non-fat milk) can be used as a liquid food substrate to which a pure culture of Ropy 352 can be added. The culture may be fermented, for instance at 30° C. without shaking for 16 to 20 hours. The EPS 352 culture may be supplied in the form as an aliquot of liquid culture or an inoculum from an agar plate (such as milk or whey agar plate). Following fermentation, the fermented product may be aliquoted into sealed containers and pasteurized. A second specific example of a fermented food product made using Ropy 352 is a power shake for the elderly and diet shakes for the obese. Trade names such as Slimfast™ or Ensure™ can be used as a liquid food substrate to which a pure culture of Ropy 352 can be added. Both Slimfast™ and Ensure™ were inoculated with a culture of Ropy352 and incubated at 30° C. for 24 hours, respectively. The results showed that not only did Ropy 352 thicken these products, but it also added active culture (probiotic) status.

The duration and temperature of fermentation may vary. Representative temperatures may range from about 17° C. to 30° C. and duration of fermentation of a batch culture may be from about 10 to 36 hours. Alternatively, fermentation may be done as a continuous culture with portions of the fermented product being periodically removed.

7. The Use of Enzymes Derived from the EPS 352 Plasmid

Enzymes derived from the EPS 352 plasmid can be used either in vitro or in vivo to produce and or modify EPS structure. Furthermore, these enzymes can be modified through the inclusion of one or more conservative amino acid substitutions, however, such conservative amino acid substituted variants will continue to maintain the same activity of the enzyme from which they are derived.

a. in vitro

Enzymes from the EPS 352 plasmid can be combined with other enzymes and substrates in vivo, such that an EPS is produced with the desired characteristics. In vitro production of an EPS involves provide the isolated enzymes that are to be used in the synthesis as well as the various substrates necessary for the production of the EPS. Detailed examples of EPS production in vitro are well known in the art and can be found for example in Bossia et al., *Cell Mol Biol* (*Noisy-le-grand*) 42(5):737-58, 1996 and Semino et al., *J Gen Microbiol* 139 (Pt 11):2745-56, 1993.

b. in vivo

The enzymes produced from the expression of ORFs, such as ORF M (SEQ ID NO: 13), ORF N (SEQ ID NO: 14), ORF O (SEQ ID NO: 9), and ORF P (SEQ ID NO: 10) that are derived from the EPS 352 plasmid can be placed under the control of heterologous control sequences. Such control sequences can be selected from constituative promoters, inducible promoters, enhancers, and various terminators. Together the control sequence(s) operably linked to the ORF is termed the "transgene". The transgene can then be transformed into a host organism that supports the production of an EPS. Upon expression of the protein from the transgene at least a portion of the EPS generated from the transformed host organism will be distinct from the non-transformed host organism.

It is also possible that the control sequences found in the EPS 352 plasmid can be used to express one of more of the ORF from the EPS 352 plasmid. Used in this way the "transgene" generated will be the result of using recombinant DNA technology to manipulate the endogenous EPS 352 plasmid such that the naturally occurring EPS 352 plasmid is not intact. Such transgenes result from the introduction of additional copies of one or more of the ORFs that are in the naturally occurring EPS 352 plasmid. It is also possible that enzymes from other EPS producing organisms will be introduced into the EPS 352 operon such that the host cell expresses an EPS that is distinct from the Ropy 352 disclosed herein.

EXAMPLES

1. Production of a Thickened Milk Product by Adding a Pure Culture of the Ropy 352 Organism to Milk and Fermenting the Mixture.

Ropy EPS 352 was expressed on plates containing whey agar and in liquid milk. The whey agar plates were incubated at 30° C. for 48 hours. Colonies were then touched with a sterile toothpick to test for Ropy EPS 352 expression. Liquid milk was sterilized by steaming for 30 minutes. 10 mL of the sterilized milk were then inoculated with 0.5 mL of an overnight pure culture of the Ropy 352 organism. The milk was incubated for 18 hours at 30° C. and visually examined for coagulation and ropy EPS 352 expression. Ropiness was indicated using a sterile glass rod to pull ropes from the milk.

2. Production of a Thickened Liquid Product by Adding a Pure Culture of the Ropy 352 Organism to Power Drinks Designed for the Elderly and Diet Drinks Designed for the Obese.

Ropy 352 was grown and EPS 352 was expressed in Slim Fast™ (Slim-Fast Foods Co., West Palm Beach, Fla.) chocolate diet drink and Ensure™ (Abbott Laboratories, Abbott Park, Ill.) chocolate fortified drink. Slim Fast™ and Ensure™ drinks were inoculated with Ropy 352 and incubated for 18 hours at 30° C. and visually examined for coagulation and ropy EPS 352 expression. Ropiness was determined using a sterile glass rod to pull ropes from the milk, and by visually examining how the fermented liquid poured from a flask.

3. Use of the EPS 352 Plasmid to Transform Cells and to Produce EPS 352.

The EPS 352 plasmid, containing an erythromycin resistant encoded insertion element for detection, was isolated from a culture of Ropy 352 using DNA preparation methods as described in Knoshaug et al., *J. Dairy Sci.* 83:633-640, 2000 (and as referred to in the methods section of this document). This DNA was used to transform a plasmid-free nonropy lactococcal strain, MG1363. Erythromycin resistant transformants were selected, and then screened for the ropy EPS 352 phenotype. Those displaying the ropy EPS 352 phenotype were Gram stained to verify that Gram positive cocci were present. MG1363 containing the EPS 352 plasmid was analyzed by Southern blot to verify the presence of EPS 352 plasmid. Presence of the EPS 352 plasmid in MG1363 correlated to the acquisition of the ropy EPS 352 phenotype.

4. Use of EPS 352 as a Substitute for Xanthan Gum

Xanthan gum is a high molecular weight polysaccharide derived from *Xanthomonas Campestris*. It contains D-glucose, D-mannose, and D-glucuronic acid as the dominant hexose units. For a more detailed discussion of the composition, physical and chemical properties, preparation, etc. of xanthan gum, see the following publications: Federal Register, Vol. 34, No. 53, Mar. 19, 1969, Subchapter B, Part 121, Subpart D; Keltrol, Technical Bulletin DB No. 18, Kelco Company, Clark, N.J.

Xanthan gum is currently used in a variety of compounds, as is evidenced by the fact that a search of the United States Patent and Trademark Office website on the Internet for "xanthan gum" in the claims of U.S. patents that have issued since 1976 identified 1,276 patents. These patents show xanthan gum being used in sprayable cleaning compositions (U.S. Pat. No. 5,948,743), hair conditioning shampoo (U.S. Pat. No. 5,948,739), ballpoint pen ink (U.S. Pat. No. 5,925,175), time-specific controlled release dosage formulations (U.S. Pat. No. 5,891,474), to improve gloss retention of surfactants (U.S. Pat. No. 5,877,142), as wells as for many other purposes.

5. Enzymatic Activity of the Enzymes Produced by the EPS 352 Plasmid

The EPS plasmid contains at least 5 previously unidentified open reading frames encoding 5 previously unidentified enzymes (O, P, M, N, and U, which are provided in SEQ ID NOS: 9, 10, 13, 14, and 16, respectively). Sequence analysis using Blast™ searching indicates that the "M" enzyme (SEQ ID NO: 13) is a glycosyltransferase enzyme. Methods of testing glycosyltransferase activity are well known in the art and described in: van Kranenburg et al., *J.*

*Bacteriol.* 181(1):338-340, 1999; Kranenburg et al., *J. Bacteriol.* 181(11):6347-6353, 1999; Stingele et al., *J. Bacteriol.* 181(20):6354-6360, 1999; Kolkman et al., *J. Bacteriol.* 178(13): 3736-3741 1996; Kolkman et al., *J. Biol. Chem.* 272(31):19502-19508; Breton, et al., *Curr. Opin. Struct. Biol.* 9:563-571, 1999; and Griffiths et al., *J. Biol. Chem.* 273(19): 11752-11757, 1998, which are herein incorporated by reference.

Similarly, sequence analysis using Blast™ searching indicates that the "P" enzyme (SEQ ID NO: 10) is a polysaccharide polymerase. Methods of testing polysaccharide polymerase activity are well known in the art and described in: Gonzalez et al., *Proc. Natl. Acad. Sci.* 95:13477-13482, 1998; Stevenson et al., *J. Bacteriol.* 178(16):4885-4893, 1996; and Glucksmann et al., *J. Bacteriol.* 175(21):7045-7055, 1993, which are herein incorporated by reference.

Sequence analysis using Blast™ searching indicates that the "N" enzyme (SEQ. ID. NO: 12 and 14) is a galactosyltransferase enzyme. Methods of testing jgalactosyltransferase activity are well known in the art and described in: van Kranenburg et al., *J. Bacteriol.* 181(1):338-340,1999; Kranenburg et al., *J. Bacteriol.* 181(11):6347-6353, 1999; Stingele et al., *J. Bacteriol.* 181(20):6354-6360, 1999; Kolkman et al., *J. Bacteriol.* 178(13):3736-3741, 1996; Kolkman, et al., *J. Biol. Chem.* 272(31):19502-19508, 1997; Breton et al., *Curr. Opin. Struct. Biol.* 9:563-571, 1999; and Griffiths et al., *J.Biol. Chem.* 273(19):11752-11757, 1998, which are herein incorporated by reference.

Sequence analysis using Blast™ searching indicates that the "O" enzyme (SEQ ID NO: 9) is a multi-unit transporting or exporter enzyme. Methods of testing activity are well known in the art and described in: Stevenson et al., *J. Bacteriol.* 178(16): 4885-4893, 1996; Glucksmann et al., *J. Bacteriol.* 175(21): 7045-7055, 1993; and Smith et al., *Mol. Microbiol.* 4(11): 1863-1869, 1990, which are herein incorporated by reference.

Finally, sequence analysis using Blast™ searching indicates that the "U" enzyme (SEQ ID NO: 15) is a glycosyltransferase/exporter enzyme. Methods of testing glycosyltransferase/exporter activity are well known in the art and described in: Stevenson et al., *J. Bacteriol.* 178(16): 4885-4893, 1996; Glucksmann et al., *J. Bacteriol.* 175(21): 7045-7055, 1993; Smith et al., *Mol. Microbiol.* 4(11): 1863-1869, 190; van Kranenburg et al., *J. Bacteriol.* 181(1): 338-340, 1999; Kranenburg et al., *J. Bacteriol.* 181(11): 6347-6353, 1999; Stingele et al., *J. Bacteriol.* 181(20): 6354-6360, 1999.; Kolkman et al., *J. Bacteriol.* 178(13): 3736-3741, 1996; Kolkman et al., *J. Biol. Chem.* 272(31): 19502-19508, 1997; Breton et al., *Struct. Biol.* 9:563-571, 1999; and Griffiths et al., *J. Biol. Chem.* 273(19): 11752-11757, 1998, which are herein incorporated by reference.

Having illustrated and described the principles of the invention in multiple embodiments and examples, it should be apparent to those skilled in the art that the invention can be modified in arrangement and detail without departing from such principles. The invention encompasses all modifications coming within the spirit and scope of the following claims.

What is claimed is:

1. An isolated nucleic acid molecule comprising at least 95% sequence identity to nucleotides 1336-2322 of SEQ ID NO: 12, wherein the nucleic acid molecule encodes a protein having galactosyltransferase activity.

2. The isolated nucleic acid molecule of claim 1, wherein the isolated nucleic acid molecule comprises nucleotides 1336-2322 of SEQ ID NO: 12.

3. The isolated nucleic acid molecule of claim 1, further comprising a detectable label.

4. A method of detecting a nucleic sequence encoding a polypeptide having galactosyltransferase activity, comprising:
   contacting the nucleic acid sequence with the isolated nucleic acid molecule of claim 3 under conditions wherein the isolated nucleic acid molecule hybridizes with the nucleic acid sequence, wherein the conditions comprises hybridizing in 5×SSC at 65° C. for 16 hours, washing twice in 2×SSC at room temperature for 15 minutes each, and washing twice in 0.2×SSC at 65° C. for 20 minutes; and
   detecting said nucleic acid.

5. A recombinant nucleic acid molecule comprising a promoter sequence operably linked to the isolated nucleic acid molecule of claim 1.

6. A cell transformed with the recombinant nucleic acid molecule of claim 5.

7. A transgenic bacteria comprising the recombinant nucleic acid molecule of claim 5.

8. A method of producing a protein, comprising:
   culturing the cell of claim 6, wherein the cell expresses, from the recombinant nucleic acid molecule, a protein having galactosyltransferase activity; and
   isolating the protein.

9. An isolated plasmid of approximately 20 kb wherein the plasmid comprises a nucleic acid molecule comprising at least 95% sequence identity to nucleotides 1336-2322 of SEQ ID NO: 12 isolated from *Lactococcus lactis* subspecies *cremoris* Ropy 352, wherein transformation of *Lactococcus* MG1363 with the plasmid results in production of a ropy polysaccharide, wherein the polysaccharide characteristics comprise:

| Composition: | Glucose: range of 54% to 58% |
| | Galactose: range of 42% to 46% |
| Charged: | Yes |
| Molecular weight: | range of 800,000 to 8,000,000 |
| Phosphorous: | Present in backbone or sidechain |
| Structure: | endpoints: galactose; |
| | branchpoints: glucose. |

10. The isolated plasmid of claim 9, further comprising a detectable label.

11. A method of detecting a nucleic acid encoding a polypeptide having galactosyltransferase activity, comprising:
   contacting the nucleic acid with the isolated plasmid of claim 10 under conditions wherein the isolated plasmid hybridizes with the nucleic acid, wherein the conditions comprise hybridizing in 5×SSC at 65° C. for 16 hours, washing twice in 2×SSC at room temperature for 15 minutes each, and washing twice in 0.2×SSC at 65° C. for 20 minutes; and
   detecting said nucleic acid.

12. An isolated cell transformed with the plasmid of claim 9.

13. The isolated cell of claim 12, wherein the cell is a bacterial cell, a yeast cell, a fungal cell, an animal cell, or a plant cell.

14. A method of producing a protein, comprising:
   culturing the cell of claim 12, wherein the cell expresses a protein having galactosyltransferase activity from the plasmid; and
   isolating the protein.

15. The isolated plasmid of claim 9, wherein the plasmid is isolated from *Lactococcus lactis* subspecies *cremoris* Ropy 352, as deposited with the USDA-ARS-NCAUR-NRRL as deposit accession number NRRL B-30229.

* * * * *

UNITED STATES PATENT AND TRADEMARK OFFICE
CERTIFICATE OF CORRECTION

PATENT NO. : 7,256,029 B2
APPLICATION NO. : 10/182960
DATED : August 14, 2007
INVENTOR(S) : Trempy et al.

It is certified that error appears in the above-identified patent and that said Letters Patent is hereby corrected as shown below:

In the Specification:

Column 1, lines 13-17:

"This invention was made in part with government support under The National Dairy Promotion and Research Board (i.e. Dairy Management Inc., DMI) and USDA/CRSEES Special Research Grant. Accordingly, the government has certain rights in this invention."

should be changed to read:

--This invention was made with government support under grant number 94-34332-1263 awarded by the U.S. Dept. of Agriculture. The government has certain rights in the invention.--.

Column 1, line 2, should insert --CROSS REFERENCE TO RELATED APPLICATIONS--.

Column 2, line 14, "(Dierkesen et al.," should read --(Dierksen et al.,--.

Column 4, line 43, "shows" should read --show--.

Column 4, line 47, "EspN" should read --EpsN--.

Column 4, line 53, "jalignments" should read --alignments--.

Column 4, line 55, "(SEQ. NO: 13)" should read --(SEQ ID NO: 13)--.

Column 4, line 57, "NIZO_B40." should read --NIZOB40.--.

Signed and Sealed this
Seventeenth Day of July, 2012

David J. Kappos
*Director of the United States Patent and Trademark Office*

CERTIFICATE OF CORRECTION (continued)

U.S. Pat. No. 7,256,029 B2

Column 4, line 66, "by an downward" should read --by a downward--.

Column 4, line 67, "Eps N." should read --EpsN.--.

Column 5, line 1, "shows" should read --show--.

Column 5, line 8, "Eps U" should read --EpsU--.

Column 5, lines 19-20, "Biology Blackwell" should read --Biology, Blackwell--.

Column 5, line 20, "(ISBN 0-02192-9);" should read --(ISBN 0-632-02182-9);--.

Column 5, line 26, "cutoff" should read --cutoff.--.

Column 5, line 28, "percent" should read --percent.--.

Column 5, line 29, "millipascals" should read --millipascals.--.

Column 5, line 63, "be effected by" should read --be affected by--.

Column 6, line 33, "solids" should read --solids.--.

Column 6, line 50, "Pharmaceutical a" should read --Pharmaceutical: a--.

Column 6, line 56, "Coating agent an" should read --Coating agent: an--.

Column 7, line 7, "Isolated an isolated" should read --An isolated--.

Column 7, lines 59-60, "$T_m\ ^-81.5°C - 16.6\ (\log_{10} [Na^+]) + 0.41\ (\%G+C) - 0.63\ (\%\ formamide)-(600/1)$" should read --$T_m = 81.5°C - 16.6\ (\log_{10} [Na^+]) + 0.41\ (\%G+C) - 0.63\ (\%\ formamide)-(600/1)$--.

Column 9, lines 10-11, "phenylaianyl," should read --phenylalanyl,--.

Column 9, line 49, "more conmmonly," should read --more commonly,--.

Column 10, line 12, "1990" should read --1990)--.

Column 10, line 17, "the interned at" should read --the internet at--.

Column 10, line 37, "parameters, (gap" should read --parameters (gap--.

Column 10, line 64, "*Lactcocci,*" should read --*Lactococci,*--.

CERTIFICATE OF CORRECTION (continued)
U.S. Pat. No. 7,256,029 B2

Column 10, line 65, "*Stand* 585: 469-480," should read --*Stand* 85: 469-480,--.

Column 11, line 13, "(Vedarnuthu et al.," should read --(Vedamuthu et al.,--.

Column 11, line 24, "1993.)" should read --1993)--.

Column 12, line 14, "(EPS 352 )" should read --(EPS 352)--.

Column 12, line 26, "EPS 352 , at" should read --EPS 352, at--.

Column 12, line 30, "glucose reside" should read --glucose residue--.

Column 13, line 3, "mPa-s" should read --mPA-s--.

Column 13, line 9, "mPa-s" should read --mPA-s--.

Column 13, line 18, "A 2.22 KB fragment" should read --A 2.22 kb fragment--.

Column 13, line 40, "(Ropy352 )" should read --(Ropy 352)--.

Column 13, line 55, "Ropy352" should read --Ropy 352--.

Column 13, line 59, "The southern blot" should read --The Southern blot--.

Column 14, line 7, "(e.g., "villi,"landfill,"" should read --(e.g., "villi", "langfil,"--.

Column 14, line 62, "Ropy352" should read --Ropy 352--.

Column 15, line 8, "produce and or modify" should read --produce and/or modify--.

Column 15, line 18, "EPS involves provide" should read --EPS involves providing--.

Column 15, line 42, "one of more" should read --one or more--.

Column 16, line 1, "ropy EPS" should read --Ropy EPS--.

Column 16, line 13, "ropy EPS" should read --Ropy EPS --.

Column 16, line 28, "ropy EPS" should read --Ropy EPS--.

Column 16, line 33, "the ropy" should read --the Ropy--.

Column 16, line 56, "as wells as" should read --as well as--.

CERTIFICATE OF CORRECTION (continued)
U.S. Pat. No. 7,256,029 B2

Column 17, line 4, "3736-3741 1996;" should read --3736-3741, 1996;--.

Column 17, lines 19-20, "jgalactosyltransferase" should read --galactosyltransferase--.

Column 17, line 27, "*J.Biol. Chem.*" should read --*J. Biol. Chem.*--.

Column 18, line 18, "1999.;" should read --1999;--.

SEQUENCE LISTING

```
<160> NUMBER OF SEQ ID NOS: 16

<210> SEQ ID NO 1
<211> LENGTH: 6850
<212> TYPE: DNA
<213> ORGANISM: Lactococcus lactis
<220> FEATURE:
<221> NAME/KEY: CDS
<222> LOCATION: (174)..(488)
<220> FEATURE:
<221> NAME/KEY: CDS
<222> LOCATION: (528)..(977)
<220> FEATURE:
<221> NAME/KEY: CDS
<222> LOCATION: (1020)..(1796)
<220> FEATURE:
<221> NAME/KEY: CDS
<222> LOCATION: (1809)..(2501)
<220> FEATURE:
<221> NAME/KEY: CDS
<222> LOCATION: (2618)..(3307)
<220> FEATURE:
<221> NAME/KEY: CDS
<222> LOCATION: (3332)..(4015)
<220> FEATURE:
<221> NAME/KEY: CDS
<222> LOCATION: (4022)..(4468)
<220> FEATURE:
<221> NAME/KEY: CDS
<222> LOCATION: (4974)..(5678)
<220> FEATURE:
<221> NAME/KEY: CDS
<222> LOCATION: (5687)..(6778)

<400> SEQUENCE: 1
gttgaaaaac cctaccttta cttgcactaa taggttttat tttatataat cattgatata      60
```

-continued

```
atattgaaaa ttaaaaaaca ccaaaatggt ttaacttaag caagttttga tttaattttt    120
cagaaaaatt aaggttttc ttacagaagt taataaaaaa agggattata ttt atg        176
                                                        Met
                                                         1 aat aat tta ttt tac cat cgt cta aag gaa cta gtt gaa tca agt ggt      224
Asn Asn Leu Phe Tyr His Arg Leu Lys Glu Leu Val Glu Ser Ser Gly
          5                   10                  15 aaa tct gca aat caa ata gaa agg gaa ttg ggt tac cct aga aat tct      272
Lys Ser Ala Asn Gln Ile Glu Arg Glu Leu Gly Tyr Pro Arg Asn Ser
         20                  25                  30 ttg aat aat tat aag ttg gga gga gaa ccc tct ggg aca aga tta ata      320
Leu Asn Asn Tyr Lys Leu Gly Gly Glu Pro Ser Gly Thr Arg Leu Ile
         35                  40              45 gga cta tca gag tat ttt aat gtg tct cca aaa tat ctg atg ggt ata      368
Gly Leu Ser Glu Tyr Phe Asn Val Ser Pro Lys Tyr Leu Met Gly Ile
 50              55                  60                  65 att gat gag cct aat gac agt tct gca att aat ctt ttt aaa act cta      416
Ile Asp Glu Pro Asn Asp Ser Ser Ala Ile Asn Leu Phe Lys Thr Leu
                 70                  75                  80 act caa gaa gag aaa aaa gaa atg ttt ata att tgt caa aaa tgg ctt      464
Thr Gln Glu Glu Lys Lys Glu Met Phe Ile Ile Cys Gln Lys Trp Leu
             85                  90                  95 ttt tta gaa tat caa ata gag tta taacaataat aaatttaggg agttttttcg    518
Phe Leu Glu Tyr Gln Ile Glu Leu
            100             105 gtagtgtaa aat aag ttt tgg aac atc aaa aat atc acc tac aat ggc gaa   569
           Asn Lys Phe Trp Asn Ile Lys Asn Ile Thr Tyr Asn Gly Glu
                            110                 115 aca agt gaa caa tta ttg gct gaa aaa gtt caa aat caa gta ttg gcg      617
Thr Ser Glu Gln Leu Leu Ala Glu Lys Val Gln Asn Gln Val Leu Ala
120                 125                 130                 135 act aac cct gat gtt gtt tta tat gaa gct cca ctt ttt aat gat aac      665
Thr Asn Pro Asp Val Val Leu Tyr Glu Ala Pro Leu Phe Asn Asp Asn
                140                 145                 150 caa aac att gaa gca aca gcc tca tgg act agt aat gag caa ctt ata      713
Gln Asn Ile Glu Ala Thr Ala Ser Trp Thr Ser Asn Glu Gln Leu Ile
            155                 160                 165 aca aat ttg gct agt aca gga gca gag gtg ata gtt caa ccc tct cca      761
Thr Asn Leu Ala Ser Thr Gly Ala Glu Val Ile Val Gln Pro Ser Pro
        170                 175                 180 ccg att tat ggt ggt gtt gtg tac ccc gta caa gaa gaa cag ttt aaa      809
Pro Ile Tyr Gly Gly Val Val Tyr Pro Val Gln Glu Glu Gln Phe Lys
    185                 190                 195 caa tct tta tct aca aag tat ccc tat ata gac tac tgg gct agt tac      857
Gln Ser Leu Ser Thr Lys Tyr Pro Tyr Ile Asp Tyr Trp Ala Ser Tyr
200                 205                 210                 215 cca gac aaa aat tct gat gaa atg aag ggg ctg gtt tct gat gat gga      905
Pro Asp Lys Asn Ser Asp Glu Met Lys Gly Leu Val Ser Asp Asp Gly
                220                 225                 230 gta tat aga aca tta aat gct tcg ggg aat aag gtt tgg cta gat tat      953
Val Tyr Arg Thr Leu Asn Ala Ser Gly Asn Lys Val Trp Leu Asp Tyr
            235                 240                 245 att act aaa tat ttt aca gca aac taattaagtt ataaataaca attattaaat    1007
Ile Thr Lys Tyr Phe Thr Ala Asn
        250                 255 attggagaag aa atg cag gaa aca cag gaa cag acg att gat tta aga ggg   1058
              Met Gln Glu Thr Gln Glu Gln Thr Ile Asp Leu Arg Gly
                                260                 265
```

-continued

| | |
|---|---|
| att ttt aaa att att cgc aaa agg tta ggt tta ata tta ttt agt gct<br>Ile Phe Lys Ile Ile Arg Lys Arg Leu Gly Leu Ile Leu Phe Ser Ala<br>270                            275                          280 | 1106 |
| tta ata gtc aca ata tta ggg agc atc tac aca ttt ttt ata gcc tcc<br>Leu Ile Val Thr Ile Leu Gly Ser Ile Tyr Thr Phe Phe Ile Ala Ser<br>285                          290                          295                          300 | 1154 |
| cca gtt tac aca gcc tca act caa ctt gtc gtt aaa cta cca aat tcg<br>Pro Val Tyr Thr Ala Ser Thr Gln Leu Val Val Lys Leu Pro Asn Ser<br>                    305                          310                          315 | 1202 |
| gag cat tca gca gcc tac gct gga gaa gtg acc ggg aat att caa atg<br>Glu His Ser Ala Ala Tyr Ala Gly Glu Val Thr Gly Asn Ile Gln Met<br>                  320                          325                          330 | 1250 |
| gcg aac aca att aac caa gtt att gtt agt cca gtc att tta gat aaa<br>Ala Asn Thr Ile Asn Gln Val Ile Val Ser Pro Val Ile Leu Asp Lys<br>335                            340                          345 | 1298 |
| gtt caa agt aat tta aat cta tct gat ggc tct ttc caa aaa caa gtt<br>Val Gln Ser Asn Leu Asn Leu Ser Asp Gly Ser Phe Gln Lys Gln Val<br>350                            355                          360 | 1346 |
| aca gta gca aat caa aca gat tca caa gtt att acg ctt act gtt aaa<br>Thr Val Ala Asn Gln Thr Asp Ser Gln Val Ile Thr Leu Thr Val Lys<br>365                          370                          375                          380 | 1394 |
| tat tct aat cct tac att gca caa aag att gca gac gag act gct aaa<br>Tyr Ser Asn Pro Tyr Ile Ala Gln Lys Ile Ala Asp Glu Thr Ala Lys<br>                  385                          390                          395 | 1442 |
| att ttt agt tca gat gca gca aaa cta ttg aat gtt act aac gtt aat<br>Ile Phe Ser Ser Asp Ala Ala Lys Leu Leu Asn Val Thr Asn Val Asn<br>                  400                          405                          410 | 1490 |
| att cta tcc aaa gca aaa gct caa aca aca cca att agt cct aaa cct<br>Ile Leu Ser Lys Ala Lys Ala Gln Thr Thr Pro Ile Ser Pro Lys Pro<br>                  415                          420                          425 | 1538 |
| aaa ttg tat tta gcg ata tct gtt ata gcc gga cta gtt tta ggt tta<br>Lys Leu Tyr Leu Ala Ile Ser Val Ile Ala Gly Leu Val Leu Gly Leu<br>430                            435                          440 | 1586 |
| gcc att gct tta ttg aag gaa tta ttt gat aac aaa att aat aaa gaa<br>Ala Ile Ala Leu Leu Lys Glu Leu Phe Asp Asn Lys Ile Asn Lys Glu<br>445                            450                          455                          460 | 1634 |
| gaa gat att gaa gct ctg ggg ctc acg gtt ctt ggt gta aca agc tat<br>Glu Asp Ile Glu Ala Leu Gly Leu Thr Val Leu Gly Val Thr Ser Tyr<br>                  465                          470                          475 | 1682 |
| gct caa atg agt gat ttt aat aag aat aca aat aaa aat ggc acg caa<br>Ala Gln Met Ser Asp Phe Asn Lys Asn Thr Asn Lys Asn Gly Thr Gln<br>                  480                          485                          490 | 1730 |
| tcg gga act aag tca agt ccg cct agc gac cat gaa gta aat aga tca<br>Ser Gly Thr Lys Ser Ser Pro Pro Ser Asp His Glu Val Asn Arg Ser<br>                495                          500                          505 | 1778 |
| tca aaa agg aat aaa aga taggagttca gg atg gct aaa aat aaa aga agc<br>Ser Lys Arg Asn Lys Arg                  Met Ala Lys Asn Lys Arg Ser<br>510                                                515                          520 | 1829 |
| ata gac aac aat cgt tat att att acc agt gtc aat cct caa tca cct<br>Ile Asp Asn Asn Arg Tyr Ile Ile Thr Ser Val Asn Pro Gln Ser Pro<br>                  525                          530                          535 | 1877 |
| att tcc gaa caa tat cgt tcg att cgt acg acc att gat ttt aaa atg<br>Ile Ser Glu Gln Tyr Arg Ser Ile Arg Thr Thr Ile Asp Phe Lys Met<br>                  540                          545                          550 | 1925 |
| gcg gat caa gga att aaa agt ttt cta gta gca tct tca gaa gta gct<br>Ala Asp Gln Gly Ile Lys Ser Phe Leu Val Ala Ser Ser Glu Val Ala<br>555                            560                          565 | 1973 |
| gta ggt aaa tca acc gta tgt gct aat ata gct gtt gct ttt gca caa<br>Val Gly Lys Ser Thr Val Cys Ala Asn Ile Ala Val Ala Phe Ala Gln<br>570                            575                          580                          585 | 2021 |

```
caa ggt aaa aaa gta ctt tta att gat ggc gat ctt cgt aaa ccg act      2069
Gln Gly Lys Lys Val Leu Leu Ile Asp Gly Asp Leu Arg Lys Pro Thr
            590                 595                 600 gtt aac att act ttt aaa gta caa aat aga gta gga tta acc aat att      2117
Val Asn Ile Thr Phe Lys Val Gln Asn Arg Val Gly Leu Thr Asn Ile
        605                 610                 615 tta atg cat caa tct tcg att gaa gat gcc ata caa ggg aca aga ctt      2165
Leu Met His Gln Ser Ser Ile Glu Asp Ala Ile Gln Gly Thr Arg Leu
    620                 625                 630 tct gaa aat ctt aca ata att acc tct ggt cca att cca cct aat cca      2213
Ser Glu Asn Leu Thr Ile Ile Thr Ser Gly Pro Ile Pro Pro Asn Pro
635                 640                 645 tcg gaa tta tta gca tct agt gca atg aag aat ttg att gac tct gtg      2261
Ser Glu Leu Leu Ala Ser Ser Ala Met Lys Asn Leu Ile Asp Ser Val
650                 655                 660                 665 tcc gat tta ttt gat gtt gtt ttg att gat act cca act ctc tct gca      2309
Ser Asp Leu Phe Asp Val Val Leu Ile Asp Thr Pro Thr Leu Ser Ala
            670                 675                 680 gtt act gat gct caa att ttg agt agt tat gta gga gga gca gtt att      2357
Val Thr Asp Ala Gln Ile Leu Ser Ser Tyr Val Gly Gly Ala Val Ile
        685                 690                 695 gtt gta cgt gcc tat gaa aca aaa aaa gag agt tta gca aaa aca aaa      2405
Val Val Arg Ala Tyr Glu Thr Lys Lys Glu Ser Leu Ala Lys Thr Lys
    700                 705                 710 aaa atg ctt gaa caa gtt aat aca aat att tta ggg gtt gtt ttg cat      2453
Lys Met Leu Glu Gln Val Asn Thr Asn Ile Leu Gly Val Val Leu His
715                 720                 725 ggg gta aac tct tct gag tca cca tcg tat tac tac cac gga gta gag      2501
Gly Val Asn Ser Ser Glu Ser Pro Ser Tyr Tyr Tyr His Gly Val Glu
730                 735                 740                 745 taattggaat aaacttgaat caaataaaag acagaaattt gtagaagagg agagcaaatg   2561
attgatattc attgccatat tttactggag ctaaaacttc tggagatact ttgaca atg   2620
                                                                Met ctg aaa tca gca att gat gaa ggg ata aca acc atc act gcc act cct      2668
Leu Lys Ser Ala Ile Asp Glu Gly Ile Thr Thr Ile Thr Ala Thr Pro
        750                 755                 760 cat cat aat cct caa ttt aat aat gaa tca ccg ctt att ttg aag aaa      2716
His His Asn Pro Gln Phe Asn Asn Glu Ser Pro Leu Ile Leu Lys Lys
    765                 770                 775 gtt aag gaa gtt caa aat atc att gac gag cat caa tta cca att gaa      2764
Val Lys Glu Val Gln Asn Ile Ile Asp Glu His Gln Leu Pro Ile Glu
780                 785                 790 gtt tta cca gga caa gag gtg aga ata tat ggt gat tta tta aaa gaa      2812
Val Leu Pro Gly Gln Glu Val Arg Ile Tyr Gly Asp Leu Leu Lys Glu
795                 800                 805                 810 ttt tct gaa gga aag tta ctg aca gca gcg ggc act tca agt tat ata      2860
Phe Ser Glu Gly Lys Leu Leu Thr Ala Ala Gly Thr Ser Ser Tyr Ile
            815                 820                 825 ttg att gaa ttt cca tca aat cat gtg cca gct tat gct aaa gaa ctt      2908
Leu Ile Glu Phe Pro Ser Asn His Val Pro Ala Tyr Ala Lys Glu Leu
        830                 835                 840 ttt tat aat att caa ttg gag gga ctt caa cct att ttg gtc cac cct      2956
Phe Tyr Asn Ile Gln Leu Glu Gly Leu Gln Pro Ile Leu Val His Pro
    845                 850                 855 gag cgt aat agc gga atc att gag aac cct gat ata tta ttt gat ttt      3004
Glu Arg Asn Ser Gly Ile Ile Glu Asn Pro Asp Ile Leu Phe Asp Phe
860                 865                 870 att gaa caa gga gta cta agt cag ata aca gct tca agt gtc act ggt      3052
Ile Glu Gln Gly Val Leu Ser Gln Ile Thr Ala Ser Ser Val Thr Gly
```

```
Ile Glu Gln Gly Val Leu Ser Gln Ile Thr Ala Ser Ser Val Thr Gly
875                 880                 885                 890 cat ttt ggt aaa aaa ata caa aag ctg tca ttt aaa atg ata gaa aac    3100
His Phe Gly Lys Lys Ile Gln Lys Leu Ser Phe Lys Met Ile Glu Asn
            895                 900                 905 cat ctt acg cat ttt gtt gca tca gat gcg cat aat gtg acg tca cgt    3148
His Leu Thr His Phe Val Ala Ser Asp Ala His Asn Val Thr Ser Arg
        910                 915                 920 gca ttt aag atg aag gaa gcg ttt gaa att att gaa gat agt tat ggt    3196
Ala Phe Lys Met Lys Glu Ala Phe Glu Ile Ile Glu Asp Ser Tyr Gly
    925                 930                 935 tct gat gta tca cga atg ttt caa aat aat gca gag tca gtg att tta    3244
Ser Asp Val Ser Arg Met Phe Gln Asn Asn Ala Glu Ser Val Ile Leu
940                 945                 950 aac gaa agt ttt tat caa gaa aaa cca aca aag atc aaa aca aag aaa    3292
Asn Glu Ser Phe Tyr Gln Glu Lys Pro Thr Lys Ile Lys Thr Lys Lys
955                 960                 965                 970 ttt tta gga tta ttt taaaaggatt aaaaggagta aata atg gaa ttt ttt    3343
Phe Leu Gly Leu Phe                           Met Glu Phe Phe
            975 gag gat gcc tca tca cct gaa tcg gga gag cct aag tta gta gaa tta    3391
Glu Asp Ala Ser Ser Pro Glu Ser Gly Glu Pro Lys Leu Val Glu Leu
980                 985                 990                 995 aaa aat ttt tct tat aga gag cta att ata aaa aga gca att gat atc    3439
Lys Asn Phe Ser Tyr Arg Glu Leu Ile Ile Lys Arg Ala Ile Asp Ile
            1000                1005                1010 cta gga gga tta gca ggt tca gtt tta ttt ctt att gcg gct gca ttg    3487
Leu Gly Gly Leu Ala Gly Ser Val Leu Phe Leu Ile Ala Ala Ala Leu
        1015                1020                1025 ctt tat atc cct tac aaa atg agc tca aaa aaa gat caa ggg cca atg    3535
Leu Tyr Ile Pro Tyr Lys Met Ser Ser Lys Lys Asp Gln Gly Pro Met
    1030                1035                1040 ttc tat aaa caa aaa cgc tat ggt aaa aat ggt aaa att ttt tat att    3583
Phe Tyr Lys Gln Lys Arg Tyr Gly Lys Asn Gly Lys Ile Phe Tyr Ile
1045                1050                1055 ttg aaa ttt aga aca atg att ctt aat gcc gag cag tat cta gaa ctt    3631
Leu Lys Phe Arg Thr Met Ile Leu Asn Ala Glu Gln Tyr Leu Glu Leu
1060                1065                1070                1075 aat cca gat gtt aaa gct gct tac cat gcc aac ggc aat aag cta gaa    3679
Asn Pro Asp Val Lys Ala Ala Tyr His Ala Asn Gly Asn Lys Leu Glu
            1080                1085                1090 aac gat cca cgg gta acg aag att ggc tca ttt ata aga cga cac tca    3727
Asn Asp Pro Arg Val Thr Lys Ile Gly Ser Phe Ile Arg Arg His Ser
        1095                1100                1105 att gat gaa ctg cca caa ttt atc aat gtt ctt aaa ggg gat atg tca    3775
Ile Asp Glu Leu Pro Gln Phe Ile Asn Val Leu Lys Gly Asp Met Ser
    1110                1115                1120 tta gtt ggt cca aga cca att ctg ctt ttt gaa gcg aaa gaa tat ggg    3823
Leu Val Gly Pro Arg Pro Ile Leu Leu Phe Glu Ala Lys Glu Tyr Gly
1125                1130                1135 aaa cgc ctc gct tac tta ctc atg tgc aaa cca gga atc act ggt tat    3871
Lys Arg Leu Ala Tyr Leu Leu Met Cys Lys Pro Gly Ile Thr Gly Tyr
1140                1145                1150                1155 tgg acg aca cat ggt cga agt aaa gtt ctt ttt cct caa cga gca gat    3919
Trp Thr Thr His Gly Arg Ser Lys Val Leu Phe Pro Gln Arg Ala Asp
            1160                1165                1170 tta gaa ctc tat tat ctc cag tac cat agc acc aaa aat gat atc aag    3967
Leu Glu Leu Tyr Tyr Leu Gln Tyr His Ser Thr Lys Asn Asp Ile Lys
        1175                1180                1185
```

-continued

| | | |
|---|---|---|
| ctt cta gta ctc aca att gta caa agt att aac gga tcg gac gca tat<br>Leu Leu Val Leu Thr Ile Val Gln Ser Ile Asn Gly Ser Asp Ala Tyr<br>     1190                    1195                  1200 | | 4015 |
| taaaaa atg aaa ata gca tta gta ggt tcc agc ggt ggc cat ttg aca<br>      Met Lys Ile Ala Leu Val Gly Ser Ser Gly Gly His Leu Thr<br>          1205                   1210                1215 | | 4063 |
| cac ctg tat ttg tta aaa aag ttt tgg gaa aac gaa gat aga ttt tgg<br>His Leu Tyr Leu Leu Lys Lys Phe Trp Glu Asn Glu Asp Arg Phe Trp<br>     1220                    1225                1230 | | 4111 |
| gtc aca ttt gat aaa aca gat gca aaa tct ata ttg aaa gaa gaa aga<br>Val Thr Phe Asp Lys Thr Asp Ala Lys Ser Ile Leu Lys Glu Glu Arg<br>     1235                    1240                1245 | | 4159 |
| ttt tat cct tgt tat tat ccc aca aat aga aat gta aaa aac acg ata<br>Phe Tyr Pro Cys Tyr Tyr Pro Thr Asn Arg Asn Val Lys Asn Thr Ile<br>1250                 1255                1260                1265 | | 4207 |
| aaa aat acc att ctt gca ttt aaa ata ctt aga aaa gaa aaa cca gat<br>Lys Asn Thr Ile Leu Ala Phe Lys Ile Leu Arg Lys Glu Lys Pro Asp<br>             1270                1275                1280 | | 4255 |
| ttg att att tcg agt ggt gct gcg gta gcc gtt cct ttt ttt tgg tta<br>Leu Ile Ile Ser Ser Gly Ala Ala Val Ala Val Pro Phe Phe Trp Leu<br>          1285                   1290                1295 | | 4303 |
| ggt aaa cta ttc ggt gca aag aca gtc tat att gaa ata ttt gac cgg<br>Gly Lys Leu Phe Gly Ala Lys Thr Val Tyr Ile Glu Ile Phe Asp Arg<br>          1300                   1305                1310 | | 4351 |
| atc gat aaa cca acc tta aca gga aaa tta gtt tat cca gtt act gat<br>Ile Asp Lys Pro Thr Leu Thr Gly Lys Leu Val Tyr Pro Val Thr Asp<br>     1315                    1320                1325 | | 4399 |
| aag ttt ata gtt caa tgg gaa gag tta aaa aaa gtt tac cct aaa gca<br>Lys Phe Ile Val Gln Trp Glu Glu Leu Lys Lys Val Tyr Pro Lys Ala<br>1330                 1335                1340                1345 | | 4447 |
| att aat tta gga gga att ttc taatgatttt tgtaacggtt ggaactcacg<br>Ile Asn Leu Gly Gly Ile Phe<br>               1350 | | 4498 |
| aacaaccatt taatcgactc attcaaaaaa ttgatgaact tgtacgcgat ggtgaaatcg | | 4558 |
| aagacgatgt attcatgcaa attgggtact caacttatga acctaaatat actaaatggg | | 4618 |
| aaaagtttat tggatatgag actatggaaa gatgtatgaa tgaagcgagt acgattatta | | 4678 |
| ctcatggcgg accatctacc tatatgcaag tattacaact aggtaaaatt ccgatagttg | | 4738 |
| ttccacggca aatgaaattt gatgagcata taaatgatca tcaactttgg gtaagtaaac | | 4798 |
| aggttgtgaa aaagggatac tcattgattt tgtgcgaaga tgttgaagac attctcgaaa | | 4858 |
| atattattag ttccaaaatt tcagatacct tacaaaaaaa tgtaaatcac aacactgaat | | 4918 |
| tcataaaatt attcagtgct gaaatttacc agctatttat aaaaagtgag aagat atg<br>                                                                                                                                                                                                                 Met | | 4976 |
| ata cca aaa gta ata cac tat tgc tgg ttc gga ggg caa cct tta cca<br>Ile Pro Lys Val Ile His Tyr Cys Trp Phe Gly Gly Gln Pro Leu Pro<br>     1355                    1360                1365 | | 5024 |
| gaa tct gcg cta aaa tgt att gaa agt tgg aga agg ttt tgt cca gat<br>Glu Ser Ala Leu Lys Cys Ile Glu Ser Trp Arg Arg Phe Cys Pro Asp<br>1370                 1375                1380                1385 | | 5072 |
| tat gaa ata aaa caa tgg tct gag aaa aac tat gat gta aat aaa att<br>Tyr Glu Ile Lys Gln Trp Ser Glu Lys Asn Tyr Asp Val Asn Lys Ile<br>     1390                    1395                1400 | | 5120 |
| caa tat att aag gaa gca tat caa gaa aaa aaa ttt gct ttt gtc acg<br>Gln Tyr Ile Lys Glu Ala Tyr Gln Glu Lys Lys Phe Ala Phe Val Thr<br>          1405                   1410                1415 | | 5168 |
| gat gtt gca agg ctc gat ata att tgg aat gaa ggc ggt ata tat ctt<br>Asp Val Ala Arg Leu Asp Ile Ile Trp Asn Glu Gly Gly Ile Tyr Leu | | 5216 |

```
                1420               1425              1430
gac acg gat gta gag ctt ata aaa tct ctt gat gaa ttg ctg tat aat    5264
Asp Thr Asp Val Glu Leu Ile Lys Ser Leu Asp Glu Leu Leu Tyr Asn
        1435               1440               1445 agt tta tat tta gga atg gaa aga gct ggt aga gta aat acg ggt tta    5312
Ser Leu Tyr Leu Gly Met Glu Arg Ala Gly Arg Val Asn Thr Gly Leu
1450               1455               1460               1465 ggg ttt gga gct gaa gta aat cat cca att gtg aga gct aat tta gaa    5360
Gly Phe Gly Ala Glu Val Asn His Pro Ile Val Arg Ala Asn Leu Glu
                1470               1475               1480 ttg tat act aat att cct ttt tca ggc aat gat aat ata act tgt gtg    5408
Leu Tyr Thr Asn Ile Pro Phe Ser Gly Asn Asp Asn Ile Thr Cys Val
        1485               1490               1495 acc tat acg acg aat ctt ttg aaa aaa tat ggt cta aaa aac aac aat    5456
Thr Tyr Thr Thr Asn Leu Leu Lys Lys Tyr Gly Leu Lys Asn Asn Asn
            1500               1505               1510 gaa att caa cat ata gat aac gca ata att tta cct act gaa tat tta    5504
Glu Ile Gln His Ile Asp Asn Ala Ile Ile Leu Pro Thr Glu Tyr Leu
    1515               1520               1525 tgt cct cta agt ttt gaa aca aat cga tta aaa ata acg gaa aat act    5552
Cys Pro Leu Ser Phe Glu Thr Asn Arg Leu Lys Ile Thr Glu Asn Thr
1530               1535               1540               1545 tac tcc atc cat cac tat gat atg agt tgg aaa gat aag aga gat aaa    5600
Tyr Ser Ile His His Tyr Asp Met Ser Trp Lys Asp Lys Arg Asp Lys
                1550               1555               1560 ttt tta aga ctt aaa ata caa ctt aga aaa tgg gta ggt gat gat ttt    5648
Phe Leu Arg Leu Lys Ile Gln Leu Arg Lys Trp Val Gly Asp Asp Phe
        1565               1570               1575 tat gaa aaa gtt att aaa aga att gga aaa taattatc atg aat aaa ata    5698
Tyr Glu Lys Val Ile Lys Arg Ile Gly Lys              Met Asn Lys Ile
    1580               1585                              1590 acc atg aca aga gag atg aga gtt att gcc tta tgt gtc gta att tta    5746
Thr Met Thr Arg Glu Met Arg Val Ile Ala Leu Cys Val Val Ile Leu
            1595               1600               1605 gaa tat tta aat aat aca gga tta att gcg tct tca gca tac tct ttt    5794
Glu Tyr Leu Asn Asn Thr Gly Leu Ile Ala Ser Ser Ala Tyr Ser Phe
    1610               1615               1620 agc atg gcg agt aca atc ctc tta tcc tat atc tta ttc tgt aaa aaa    5842
Ser Met Ala Ser Thr Ile Leu Leu Ser Tyr Ile Leu Phe Cys Lys Lys
1625               1630               1635 aga aaa gga ttt tct tta aag gag att att gta cta cta att cca ttt    5890
Arg Lys Gly Phe Ser Leu Lys Glu Ile Ile Val Leu Leu Ile Pro Phe
1640               1645               1650               1655 att ttt gta gtt tta aat cgt gat cct agt aat ttc agt tta ggg tta    5938
Ile Phe Val Val Leu Asn Arg Asp Pro Ser Asn Phe Ser Leu Gly Leu
                1660               1665               1670 atg tgg ata ctc tat ttt atg tta agt aag tcg gaa ata gat tta aaa    5986
Met Trp Ile Leu Tyr Phe Met Leu Ser Lys Ser Glu Ile Asp Leu Lys
        1675               1680               1685 aaa gtg atg aaa aca ttt ttt gtt acc tct agt gtt tgt ttt att ttg    6034
Lys Val Met Lys Thr Phe Phe Val Thr Ser Ser Val Cys Phe Ile Leu
    1690               1695               1700 aca ata gta ctt tat tta ata atg tct ctt aat aaa agc tct gat atg    6082
Thr Ile Val Leu Tyr Leu Ile Met Ser Leu Asn Lys Ser Ser Asp Met
1705               1710               1715 ata atg tgg cgt gga gat gct ttt ata aat cgt atg agt tta gga ttt    6130
Ile Met Trp Arg Gly Asp Ala Phe Ile Asn Arg Met Ser Leu Gly Phe
1720               1725               1730               1735 atc caa ccg aat ttt gca atg atg agc ttt tta ggt ata gcg ata gcc    6178
```

-continued

```
Ile Gln Pro Asn Phe Ala Met Met Ser Phe Leu Gly Ile Ala Ile Ala
              1740                1745                1750 tta tta tat ttg agt act gaa aga caa aga ata act ata att ttt att      6226
Leu Leu Tyr Leu Ser Thr Glu Arg Gln Arg Ile Thr Ile Ile Phe Ile
              1755                1760                1765 gcc att gta act ttt att ata ttt tac ttt act caa tca aga act tca      6274
Ala Ile Val Thr Phe Ile Ile Phe Tyr Phe Thr Gln Ser Arg Thr Ser
              1770                1775                1780 gga tat atc tta ttt ttt att ttg agt att tta ttt gtt agt agt aaa      6322
Gly Tyr Ile Leu Phe Phe Ile Leu Ser Ile Leu Phe Val Ser Ser Lys
              1785                1790                1795 aaa act aaa aag caa gtt tca aat ttt gaa aaa agg agc att aca gtt      6370
Lys Thr Lys Lys Gln Val Ser Asn Phe Glu Lys Arg Ser Ile Thr Val
1800                1805                1810                1815 tta cca cta ctt ctt tta atc atc tct tat tcg ttg tta aag tta cct      6418
Leu Pro Leu Leu Leu Leu Ile Ile Ser Tyr Ser Leu Leu Lys Leu Pro
              1820                1825                1830 att aat caa tac atc aat agc ttg ctt tct ggt cgt ctg gcg ctt tat      6466
Ile Asn Gln Tyr Ile Asn Ser Leu Leu Ser Gly Arg Leu Ala Leu Tyr
              1835                1840                1845 caa gag att tat tct aca ttt ggt ata cat ttg ata ggg aat aat gat      6514
Gln Glu Ile Tyr Ser Thr Phe Gly Ile His Leu Ile Gly Asn Asn Asp
              1850                1855                1860 gtt aaa aat aca atg tta gat aca gca tat ctt caa agt ttg cta gca      6562
Val Lys Asn Thr Met Leu Asp Thr Ala Tyr Leu Gln Ser Leu Leu Ala
              1865                1870                1875 aaa gga att ttg ttt aca ttg ttt tta ttt gta act ttc ttt ttc ata      6610
Lys Gly Ile Leu Phe Thr Leu Phe Leu Phe Val Thr Phe Phe Phe Ile
1880                1885                1890                1895 ttt ttt ctt aag aga aaa aca caa act agg ttg caa agt tta gta att      6658
Phe Phe Leu Lys Arg Lys Thr Gln Thr Arg Leu Gln Ser Leu Val Ile
              1900                1905                1910 atg atg tat ttt tta att gca ttt aca gaa aca tca ttt ttt agg ttt      6706
Met Met Tyr Phe Leu Ile Ala Phe Thr Glu Thr Ser Phe Phe Arg Phe
              1915                1920                1925 gta att tta ttt cca gta ttg atg gta ata atg gat cag aaa gag gct      6754
Val Ile Leu Phe Pro Val Leu Met Val Ile Met Asp Gln Lys Glu Ala
              1930                1935                1940 aat aaa gta ata gaa aag gtg gca tagtgagtat taataaaaca gagattgagg     6808
Asn Lys Val Ile Glu Lys Val Ala
              1945                1950 aatacaaagt atccgttata gttcctgttt acaatgtaga gg                       6850
```

<210> SEQ ID NO 2
<211> LENGTH: 105
<212> TYPE: PRT
<213> ORGANISM: Lactococcus lactis

<400> SEQUENCE: 2

```
Met Asn Asn Leu Phe Tyr His Arg Leu Lys Glu Leu Val Glu Ser Ser
1               5                   10                  15

Gly Lys Ser Ala Asn Gln Ile Glu Arg Glu Leu Gly Tyr Pro Arg Asn
            20                  25                  30

Ser Leu Asn Asn Tyr Lys Leu Gly Gly Glu Pro Ser Gly Thr Arg Leu
        35                  40                  45

Ile Gly Leu Ser Glu Tyr Phe Asn Val Ser Pro Lys Tyr Leu Met Gly
    50                  55                  60

Ile Ile Asp Glu Pro Asn Asp Ser Ser Ala Ile Asn Leu Phe Lys Thr
65                  70                  75                  80
```

Leu Thr Gln Glu Glu Lys Lys Glu Met Phe Ile Ile Cys Gln Lys Trp
            85                  90                  95

Leu Phe Leu Glu Tyr Gln Ile Glu Leu
            100                 105

<210> SEQ ID NO 3
<211> LENGTH: 150
<212> TYPE: PRT
<213> ORGANISM: Lactococcus lactis

<400> SEQUENCE: 3

Asn Lys Phe Trp Asn Ile Lys Asn Ile Thr Tyr Asn Gly Glu Thr Ser
 1               5                  10                  15

Glu Gln Leu Leu Ala Glu Lys Val Gln Asn Gln Val Leu Ala Thr Asn
            20                  25                  30

Pro Asp Val Val Leu Tyr Glu Ala Pro Leu Phe Asn Asp Asn Gln Asn
            35                  40                  45

Ile Glu Ala Thr Ala Ser Trp Thr Ser Asn Glu Gln Leu Ile Thr Asn
     50                  55                  60

Leu Ala Ser Thr Gly Ala Glu Val Ile Val Gln Pro Ser Pro Pro Ile
 65                  70                  75                  80

Tyr Gly Gly Val Val Tyr Pro Val Gln Glu Glu Gln Phe Lys Gln Ser
                 85                  90                  95

Leu Ser Thr Lys Tyr Pro Tyr Ile Asp Tyr Trp Ala Ser Tyr Pro Asp
            100                 105                 110

Lys Asn Ser Asp Glu Met Lys Gly Leu Val Ser Asp Asp Gly Val Tyr
            115                 120                 125

Arg Thr Leu Asn Ala Ser Gly Asn Lys Val Trp Leu Asp Tyr Ile Thr
            130                 135                 140

Lys Tyr Phe Thr Ala Asn
145                 150

<210> SEQ ID NO 4
<211> LENGTH: 259
<212> TYPE: PRT
<213> ORGANISM: Lactococcus lactis

<400> SEQUENCE: 4

Met Gln Glu Thr Gln Glu Gln Thr Ile Asp Leu Arg Gly Ile Phe Lys
 1               5                  10                  15

Ile Ile Arg Lys Arg Leu Gly Leu Ile Leu Phe Ser Ala Leu Ile Val
            20                  25                  30

Thr Ile Leu Gly Ser Ile Tyr Thr Phe Phe Ile Ala Ser Pro Val Tyr
            35                  40                  45

Thr Ala Ser Thr Gln Leu Val Val Lys Leu Pro Asn Ser Glu His Ser
     50                  55                  60

Ala Ala Tyr Ala Gly Glu Val Thr Gly Asn Ile Gln Met Ala Asn Thr
 65                  70                  75                  80

Ile Asn Gln Val Ile Val Ser Pro Val Ile Leu Asp Lys Val Gln Ser
                 85                  90                  95

Asn Leu Asn Leu Ser Asp Gly Ser Phe Gln Lys Gln Val Thr Val Ala
            100                 105                 110

Asn Gln Thr Asp Ser Gln Val Ile Thr Leu Thr Val Lys Tyr Ser Asn
            115                 120                 125

Pro Tyr Ile Ala Gln Lys Ile Ala Asp Glu Thr Ala Lys Ile Phe Ser
            130                 135                 140

```
Ser Asp Ala Ala Lys Leu Leu Asn Val Thr Asn Val Asn Ile Leu Ser
145                 150                 155                 160

Lys Ala Lys Ala Gln Thr Thr Pro Ile Ser Pro Lys Pro Lys Leu Tyr
                165                 170                 175

Leu Ala Ile Ser Val Ile Ala Gly Leu Val Leu Gly Leu Ala Ile Ala
            180                 185                 190

Leu Leu Lys Glu Leu Phe Asp Asn Lys Ile Asn Lys Glu Glu Asp Ile
        195                 200                 205

Glu Ala Leu Gly Leu Thr Val Leu Gly Val Thr Ser Tyr Ala Gln Met
    210                 215                 220

Ser Asp Phe Asn Lys Asn Thr Asn Lys Asn Gly Thr Gln Ser Gly Thr
225                 230                 235                 240

Lys Ser Ser Pro Pro Ser Asp His Glu Val Asn Arg Ser Ser Lys Arg
                245                 250                 255

Asn Lys Arg

<210> SEQ ID NO 5
<211> LENGTH: 231
<212> TYPE: PRT
<213> ORGANISM: Lactococcus lactis

<400> SEQUENCE: 5

Met Ala Lys Asn Lys Arg Ser Ile Asp Asn Asn Arg Tyr Ile Ile Thr
1               5                   10                  15

Ser Val Asn Pro Gln Ser Pro Ile Ser Glu Gln Tyr Arg Ser Ile Arg
            20                  25                  30

Thr Thr Ile Asp Phe Lys Met Ala Asp Gln Gly Ile Lys Ser Phe Leu
        35                  40                  45

Val Ala Ser Ser Glu Val Ala Val Gly Lys Ser Thr Val Cys Ala Asn
    50                  55                  60

Ile Ala Val Ala Phe Ala Gln Gln Gly Lys Lys Val Leu Leu Ile Asp
65                  70                  75                  80

Gly Asp Leu Arg Lys Pro Thr Val Asn Ile Thr Phe Lys Val Gln Asn
                85                  90                  95

Arg Val Gly Leu Thr Asn Ile Leu Met His Gln Ser Ser Ile Glu Asp
            100                 105                 110

Ala Ile Gln Gly Thr Arg Leu Ser Glu Asn Leu Thr Ile Ile Thr Ser
        115                 120                 125

Gly Pro Ile Pro Pro Asn Pro Ser Glu Leu Leu Ala Ser Ser Ala Met
    130                 135                 140

Lys Asn Leu Ile Asp Ser Val Ser Asp Leu Phe Asp Val Val Leu Ile
145                 150                 155                 160

Asp Thr Pro Thr Leu Ser Ala Val Thr Asp Ala Gln Ile Leu Ser Ser
                165                 170                 175

Tyr Val Gly Gly Ala Val Ile Val Val Arg Ala Tyr Glu Thr Lys Lys
            180                 185                 190

Glu Ser Leu Ala Lys Thr Lys Lys Met Leu Glu Gln Val Asn Thr Asn
        195                 200                 205

Ile Leu Gly Val Val Leu His Gly Val Asn Ser Ser Glu Ser Pro Ser
    210                 215                 220

Tyr Tyr Tyr His Gly Val Glu
225                 230

<210> SEQ ID NO 6
```

```
<211> LENGTH: 230
<212> TYPE: PRT
<213> ORGANISM: Lactococcus lactis

<400> SEQUENCE: 6

Met Leu Lys Ser Ala Ile Asp Glu Gly Ile Thr Thr Ile Thr Ala Thr
 1               5                  10                  15

Pro His His Asn Pro Gln Phe Asn Asn Glu Ser Pro Leu Ile Leu Lys
             20                  25                  30

Lys Val Lys Glu Val Gln Asn Ile Ile Asp Glu His Gln Leu Pro Ile
         35                  40                  45

Glu Val Leu Pro Gly Gln Glu Val Arg Ile Tyr Gly Asp Leu Leu Lys
     50                  55                  60

Glu Phe Ser Glu Gly Lys Leu Leu Thr Ala Ala Gly Thr Ser Ser Tyr
 65                  70                  75                  80

Ile Leu Ile Glu Phe Pro Ser Asn His Val Pro Ala Tyr Ala Lys Glu
                 85                  90                  95

Leu Phe Tyr Asn Ile Gln Leu Glu Gly Leu Gln Pro Ile Leu Val His
            100                 105                 110

Pro Glu Arg Asn Ser Gly Ile Ile Glu Asn Pro Asp Ile Leu Phe Asp
        115                 120                 125

Phe Ile Glu Gln Gly Val Leu Ser Gln Ile Thr Ala Ser Ser Val Thr
130                 135                 140

Gly His Phe Gly Lys Lys Ile Gln Lys Leu Ser Phe Lys Met Ile Glu
145                 150                 155                 160

Asn His Leu Thr His Phe Val Ala Ser Asp Ala His Asn Val Thr Ser
                165                 170                 175

Arg Ala Phe Lys Met Lys Glu Ala Phe Glu Ile Ile Glu Asp Ser Tyr
            180                 185                 190

Gly Ser Asp Val Ser Arg Met Phe Gln Asn Asn Ala Glu Ser Val Ile
        195                 200                 205

Leu Asn Glu Ser Phe Tyr Gln Glu Lys Pro Thr Lys Ile Lys Thr Lys
    210                 215                 220

Lys Phe Leu Gly Leu Phe
225                 230

<210> SEQ ID NO 7
<211> LENGTH: 228
<212> TYPE: PRT
<213> ORGANISM: Lactococcus lactis

<400> SEQUENCE: 7

Met Glu Phe Phe Glu Asp Ala Ser Ser Pro Glu Ser Gly Glu Pro Lys
 1               5                  10                  15

Leu Val Glu Leu Lys Asn Phe Ser Tyr Arg Glu Leu Ile Ile Lys Arg
             20                  25                  30

Ala Ile Asp Ile Leu Gly Gly Leu Ala Gly Ser Val Leu Phe Leu Ile
         35                  40                  45

Ala Ala Ala Leu Leu Tyr Ile Pro Tyr Lys Met Ser Ser Lys Lys Asp
     50                  55                  60

Gln Gly Pro Met Phe Tyr Lys Gln Lys Arg Tyr Gly Lys Asn Gly Lys
 65                  70                  75                  80

Ile Phe Tyr Ile Leu Lys Phe Arg Thr Met Ile Leu Asn Ala Glu Gln
                 85                  90                  95

Tyr Leu Glu Leu Asn Pro Asp Val Lys Ala Ala Tyr His Ala Asn Gly
            100                 105                 110
```

Asn Lys Leu Glu Asn Asp Pro Arg Val Thr Lys Ile Gly Ser Phe Ile
            115                 120                 125

Arg Arg His Ser Ile Asp Glu Leu Pro Gln Phe Ile Asn Val Leu Lys
        130                 135                 140

Gly Asp Met Ser Leu Val Gly Pro Arg Pro Ile Leu Leu Phe Glu Ala
145                 150                 155                 160

Lys Glu Tyr Gly Lys Arg Leu Ala Tyr Leu Leu Met Cys Lys Pro Gly
                165                 170                 175

Ile Thr Gly Tyr Trp Thr Thr His Gly Arg Ser Lys Val Leu Phe Pro
            180                 185                 190

Gln Arg Ala Asp Leu Glu Leu Tyr Tyr Leu Gln Tyr His Ser Thr Lys
        195                 200                 205

Asn Asp Ile Lys Leu Leu Val Leu Thr Ile Val Gln Ser Ile Asn Gly
            210                 215                 220

Ser Asp Ala Tyr
225

<210> SEQ ID NO 8
<211> LENGTH: 149
<212> TYPE: PRT
<213> ORGANISM: Lactococcus lactis

<400> SEQUENCE: 8

Met Lys Ile Ala Leu Val Gly Ser Ser Gly Gly His Leu Thr His Leu
1               5                   10                  15

Tyr Leu Leu Lys Lys Phe Trp Glu Asn Glu Asp Arg Phe Trp Val Thr
            20                  25                  30

Phe Asp Lys Thr Asp Ala Lys Ser Ile Leu Lys Glu Glu Arg Phe Tyr
        35                  40                  45

Pro Cys Tyr Tyr Pro Thr Asn Arg Asn Val Lys Asn Thr Ile Lys Asn
    50                  55                  60

Thr Ile Leu Ala Phe Lys Ile Leu Arg Lys Glu Lys Pro Asp Leu Ile
65                  70                  75                  80

Ile Ser Ser Gly Ala Ala Val Ala Val Pro Phe Phe Trp Leu Gly Lys
                85                  90                  95

Leu Phe Gly Ala Lys Thr Val Tyr Ile Glu Ile Phe Asp Arg Ile Asp
            100                 105                 110

Lys Pro Thr Leu Thr Gly Lys Leu Val Tyr Pro Val Thr Asp Lys Phe
        115                 120                 125

Ile Val Gln Trp Glu Glu Leu Lys Lys Val Tyr Pro Lys Ala Ile Asn
    130                 135                 140

Leu Gly Gly Ile Phe
145

<210> SEQ ID NO 9
<211> LENGTH: 235
<212> TYPE: PRT
<213> ORGANISM: Lactococcus lactis

<400> SEQUENCE: 9

Met Ile Pro Lys Val Ile His Tyr Cys Trp Phe Gly Gly Gln Pro Leu
1               5                   10                  15

Pro Glu Ser Ala Leu Lys Cys Ile Glu Ser Trp Arg Arg Phe Cys Pro
            20                  25                  30

Asp Tyr Glu Ile Lys Gln Trp Ser Glu Lys Asn Tyr Asp Val Asn Lys
        35                  40                  45

-continued

```
Ile Gln Tyr Ile Lys Glu Ala Tyr Gln Glu Lys Lys Phe Ala Phe Val
         50                  55                  60

Thr Asp Val Ala Arg Leu Asp Ile Ile Trp Asn Glu Gly Gly Ile Tyr
 65                  70                  75                  80

Leu Asp Thr Asp Val Glu Leu Ile Lys Ser Leu Asp Glu Leu Leu Tyr
                     85                  90                  95

Asn Ser Leu Tyr Leu Gly Met Glu Arg Ala Gly Arg Val Asn Thr Gly
                100                 105                 110

Leu Gly Phe Gly Ala Glu Val Asn His Pro Ile Val Arg Ala Asn Leu
            115                 120                 125

Glu Leu Tyr Thr Asn Ile Pro Phe Ser Gly Asn Asp Asn Ile Thr Cys
        130                 135                 140

Val Thr Tyr Thr Thr Asn Leu Leu Lys Lys Tyr Gly Leu Lys Asn Asn
145                 150                 155                 160

Asn Glu Ile Gln His Ile Asp Asn Ala Ile Ile Leu Pro Thr Glu Tyr
                165                 170                 175

Leu Cys Pro Leu Ser Phe Glu Thr Asn Arg Leu Lys Ile Thr Glu Asn
                180                 185                 190

Thr Tyr Ser Ile His His Tyr Asp Met Ser Trp Lys Asp Lys Arg Asp
            195                 200                 205

Lys Phe Leu Arg Leu Lys Ile Gln Leu Arg Lys Trp Val Gly Asp Asp
        210                 215                 220

Phe Tyr Glu Lys Val Ile Lys Arg Ile Gly Lys
225                 230                 235

<210> SEQ ID NO 10
<211> LENGTH: 364
<212> TYPE: PRT
<213> ORGANISM: Lactococcus lactis

<400> SEQUENCE: 10

Met Asn Lys Ile Thr Met Thr Arg Glu Met Arg Val Ile Ala Leu Cys
  1               5                  10                  15

Val Val Ile Leu Glu Tyr Leu Asn Asn Thr Gly Leu Ile Ala Ser Ser
                 20                  25                  30

Ala Tyr Ser Phe Ser Met Ala Ser Thr Ile Leu Leu Ser Tyr Ile Leu
             35                  40                  45

Phe Cys Lys Lys Arg Lys Gly Phe Ser Leu Lys Glu Ile Ile Val Leu
         50                  55                  60

Leu Ile Pro Phe Ile Phe Val Val Leu Asn Arg Asp Pro Ser Asn Phe
 65                  70                  75                  80

Ser Leu Gly Leu Met Trp Ile Leu Tyr Phe Met Leu Ser Lys Ser Glu
                     85                  90                  95

Ile Asp Leu Lys Lys Val Met Lys Thr Phe Val Thr Ser Ser Val
                100                 105                 110

Cys Phe Ile Leu Thr Ile Val Leu Tyr Leu Ile Met Ser Leu Asn Lys
            115                 120                 125

Ser Ser Asp Met Ile Met Trp Arg Gly Asp Ala Phe Ile Asn Arg Met
        130                 135                 140

Ser Leu Gly Phe Ile Gln Pro Asn Phe Ala Met Met Ser Phe Leu Gly
145                 150                 155                 160

Ile Ala Ile Ala Leu Leu Tyr Leu Ser Thr Glu Arg Gln Arg Ile Thr
                165                 170                 175

Ile Ile Phe Ile Ala Ile Val Thr Phe Ile Ile Phe Tyr Phe Thr Gln
```

```
                180                 185                 190
Ser Arg Thr Ser Gly Tyr Ile Leu Phe Phe Ile Leu Ser Ile Leu Phe
            195                 200                 205

Val Ser Ser Lys Lys Thr Lys Lys Gln Val Ser Asn Phe Glu Lys Arg
210                 215                 220

Ser Ile Thr Val Leu Pro Leu Leu Leu Ile Ile Ser Tyr Ser Leu
225                 230                 235                 240

Leu Lys Leu Pro Ile Asn Gln Tyr Ile Asn Ser Leu Leu Ser Gly Arg
                245                 250                 255

Leu Ala Leu Tyr Gln Glu Ile Tyr Ser Thr Phe Gly Ile His Leu Ile
            260                 265                 270

Gly Asn Asn Asp Val Lys Asn Thr Met Leu Asp Thr Ala Tyr Leu Gln
            275                 280                 285

Ser Leu Leu Ala Lys Gly Ile Leu Phe Thr Leu Phe Leu Phe Val Thr
290                 295                 300

Phe Phe Phe Ile Phe Phe Leu Lys Arg Lys Thr Gln Thr Arg Leu Gln
305                 310                 315                 320

Ser Leu Val Ile Met Met Tyr Phe Leu Ile Ala Phe Thr Glu Thr Ser
            325                 330                 335

Phe Phe Arg Phe Val Ile Leu Phe Pro Val Leu Met Val Ile Met Asp
            340                 345                 350

Gln Lys Glu Ala Asn Lys Val Ile Glu Lys Val Ala
            355                 360
```

<210> SEQ ID NO 11
<211> LENGTH: 168
<212> TYPE: PRT
<213> ORGANISM: Lactococcus lactis

<400> SEQUENCE: 11

```
Met Ile Phe Val Thr Val Gly Thr His Glu Gln Pro Phe Asn Arg Leu
1               5                   10                  15

Ile Gln Lys Ile Asp Glu Leu Val Arg Asp Gly Glu Ile Glu Asp Asp
            20                  25                  30

Val Phe Met Gln Ile Gly Tyr Ser Thr Tyr Glu Pro Lys Tyr Thr Lys
        35                  40                  45

Trp Glu Lys Phe Ile Gly Tyr Glu Thr Met Glu Arg Cys Met Asn Glu
    50                  55                  60

Ala Ser Thr Ile Ile Thr His Gly Gly Pro Ser Thr Tyr Met Gln Val
65                  70                  75                  80

Leu Gln Leu Gly Lys Ile Pro Ile Val Val Pro Arg Gln Met Lys Phe
                85                  90                  95

Asp Glu His Ile Asn Asp His Gln Leu Trp Val Ser Lys Gln Val Val
            100                 105                 110

Lys Lys Gly Tyr Ser Leu Ile Leu Cys Glu Asp Val Glu Asp Ile Leu
        115                 120                 125

Glu Asn Ile Ile Ser Ser Lys Ile Ser Asp Thr Leu Gln Lys Asn Val
    130                 135                 140

Asn His Asn Thr Glu Phe Ile Lys Leu Phe Ser Ala Glu Ile Tyr Gln
145                 150                 155                 160

Leu Phe Ile Lys Ser Glu Lys Ile
                165
```

<210> SEQ ID NO 12
<211> LENGTH: 2349

-continued

```
<212> TYPE: DNA
<213> ORGANISM: Lactococcus lactis
<220> FEATURE:
<221> NAME/KEY: CDS
<222> LOCATION: (61)..(1056)
<220> FEATURE:
<221> NAME/KEY: CDS
<222> LOCATION: (1336)..(2322)

<400> SEQUENCE: 12
```

| | | | | | | | | | | | | |
|---|---|---|---|---|---|---|---|---|---|---|---|---|
| cagagagaaa attatttaaa aagggaactt aattaagctt aaaattgggg gagtataaaa | | | | | | | | | | | | 60 |
| ttg agc gaa aat tta atc agt att ata gta cca gtt tat aat tca gaa | | | | | | | | | | | | 108 |
| Leu Ser Glu Asn Leu Ile Ser Ile Ile Val Pro Val Tyr Asn Ser Glu | | | | | | | | | | | | |
| 1 | | | 5 | | | | 10 | | | | 15 | |
| aag tat tta aga gcg gct att cat agt cta tta aat caa act tat caa | | | | | | | | | | | | 156 |
| Lys Tyr Leu Arg Ala Ala Ile His Ser Leu Leu Asn Gln Thr Tyr Gln | | | | | | | | | | | | |
| | | 20 | | | | 25 | | | | 30 | | |
| aat att gaa gtt att ttg att aat gat ggg tcc act gat ggc tca caa | | | | | | | | | | | | 204 |
| Asn Ile Glu Val Ile Leu Ile Asn Asp Gly Ser Thr Asp Gly Ser Gln | | | | | | | | | | | | |
| 35 | | | | 40 | | | | 45 | | | | |
| gag cta att agc tca ttt caa aaa aag gat aaa aga att aaa tta tat | | | | | | | | | | | | 252 |
| Glu Leu Ile Ser Ser Phe Gln Lys Lys Asp Lys Arg Ile Lys Leu Tyr | | | | | | | | | | | | |
| 50 | | | | 55 | | | | 60 | | | | |
| aat act aaa aat ctg ggg gta tcg cat gcg aga aat tat ggt att gat | | | | | | | | | | | | 300 |
| Asn Thr Lys Asn Leu Gly Val Ser His Ala Arg Asn Tyr Gly Ile Asp | | | | | | | | | | | | |
| 65 | | | 70 | | | | 75 | | | | 80 | |
| aga gct agt ggt tcg tat att atg ttt tta gac cca gac gac act tat | | | | | | | | | | | | 348 |
| Arg Ala Ser Gly Ser Tyr Ile Met Phe Leu Asp Pro Asp Asp Thr Tyr | | | | | | | | | | | | |
| | | | 85 | | | | 90 | | | | 95 | |
| gat aaa agt tac tgt tta gaa atg att ggg ttg att aat aag ttt aat | | | | | | | | | | | | 396 |
| Asp Lys Ser Tyr Cys Leu Glu Met Ile Gly Leu Ile Asn Lys Phe Asn | | | | | | | | | | | | |
| | | 100 | | | | 105 | | | | 110 | | |
| gct gat gtt gtt atg agt aat tac tat ata tgc aaa ggc aaa aat ata | | | | | | | | | | | | 444 |
| Ala Asp Val Val Met Ser Asn Tyr Tyr Ile Cys Lys Gly Lys Asn Ile | | | | | | | | | | | | |
| | 115 | | | | 120 | | | | 125 | | | |
| tat cct aat gtt aat aat gat ctt ctt gaa tgt gaa ggc ctc cta tca | | | | | | | | | | | | 492 |
| Tyr Pro Asn Val Asn Asn Asp Leu Leu Glu Cys Glu Gly Leu Leu Ser | | | | | | | | | | | | |
| 130 | | | | 135 | | | | 140 | | | | |
| agg gat aaa aca atg cgt tca ata cta tct gat aca ggt ttt aaa ggg | | | | | | | | | | | | 540 |
| Arg Asp Lys Thr Met Arg Ser Ile Leu Ser Asp Thr Gly Phe Lys Gly | | | | | | | | | | | | |
| 145 | | | | 150 | | | | 155 | | | | 160 |
| ttt gta tgg aca aga att ttt aga aaa aat gta att aat aat gtt aaa | | | | | | | | | | | | 588 |
| Phe Val Trp Thr Arg Ile Phe Arg Lys Asn Val Ile Asn Asn Val Lys | | | | | | | | | | | | |
| | | | 165 | | | | 170 | | | | 175 | |
| ttc aat gag agc ata aat tac tta gaa gac atg tta ttt aat att agt | | | | | | | | | | | | 636 |
| Phe Asn Glu Ser Ile Asn Tyr Leu Glu Asp Met Leu Phe Asn Ile Ser | | | | | | | | | | | | |
| | | 180 | | | | 185 | | | | 190 | | |
| att gta cat aat gca aga att ata gcc tat aca aat aaa aga cat tat | | | | | | | | | | | | 684 |
| Ile Val His Asn Ala Arg Ile Ile Ala Tyr Thr Asn Lys Arg His Tyr | | | | | | | | | | | | |
| | 195 | | | | 200 | | | | 205 | | | |
| ttt tat tta caa aga gaa gat tct gca tca aaa aaa ttt agc aaa tct | | | | | | | | | | | | 732 |
| Phe Tyr Leu Gln Arg Glu Asp Ser Ala Ser Lys Lys Phe Ser Lys Ser | | | | | | | | | | | | |
| 210 | | | | 215 | | | | 220 | | | | |
| ttt ttt aaa tcc ctt aat ctt att aga ggg aaa gtt gat cct gaa ttt | | | | | | | | | | | | 780 |
| Phe Phe Lys Ser Leu Asn Leu Ile Arg Gly Lys Val Asp Pro Glu Phe | | | | | | | | | | | | |
| 225 | | | | 230 | | | | 235 | | | | 240 |
| tat tcg caa att gat tct gtt att ttt tat aat tta gtt gga tgg tta | | | | | | | | | | | | 828 |
| Tyr Ser Gln Ile Asp Ser Val Ile Phe Tyr Asn Leu Val Gly Trp Leu | | | | | | | | | | | | |
| | | | 245 | | | | 250 | | | | 255 | |
| ata act gag aga aag agt agg gaa aat agt caa ttt ata agg aga aat | | | | | | | | | | | | 876 |
| Ile Thr Glu Arg Lys Ser Arg Glu Asn Ser Gln Phe Ile Arg Arg Asn | | | | | | | | | | | | |

-continued

```
            260                 265                 270
att aaa aat atg aaa tcc caa gtt aag ttt aaa acg ctt aaa atg gaa     924
Ile Lys Asn Met Lys Ser Gln Val Lys Phe Lys Thr Leu Lys Met Glu
            275                 280                 285 aac cca ata aaa aat tta ata tta aaa tta agc tat gct ttt ccc tta     972
Asn Pro Ile Lys Asn Leu Ile Leu Lys Leu Ser Tyr Ala Phe Pro Leu
            290                 295                 300 gta gga tcg tgt atg ata cat atg tta tcc gtt ttt atg aaa acc aaa    1020
Val Gly Ser Cys Met Ile His Met Leu Ser Val Phe Met Lys Thr Lys
305                 310                 315                 320 ctt tat tcc aaa tta atg agt atg tta agg aaa ggg tgaatcaaaa         1066
Leu Tyr Ser Lys Leu Met Ser Met Leu Arg Lys Gly
                325                 330 acaatattta agataaattt tggggttaaa accaattctg tgggttggac atacattaaa   1126
tctaaagcat ttttaatgcg agtcttgacc gtggtcatag gggatttgac ttctaagaat   1186
gttgttaagc attactaacg gagttagaat tttagagagc gtaaaatatc ttgtgataat   1246
tattaactta tcaagtacag accaaaatac tggagtttaa caggaactgt tagaatataa   1306
ttttatataa ttaggagtag aataaagag atg aat cca tta ata tca att att     1359
                                 Met Asn Pro Leu Ile Ser Ile Ile
                                             335                 340 gtt cca ata tac aat gtt gag aag tat att ggt agt tta gta aat tct    1407
Val Pro Ile Tyr Asn Val Glu Lys Tyr Ile Gly Ser Leu Val Asn Ser
            345                 350                 355 cta ttg aaa caa acg aac aag aat ttt gag gtt att ttt att gat gac    1455
Leu Leu Lys Gln Thr Asn Lys Asn Phe Glu Val Ile Phe Ile Asp Asp
            360                 365                 370 gga tca act gat gaa agc atg caa att ttg aaa gaa ata atg gca ggc    1503
Gly Ser Thr Asp Glu Ser Met Gln Ile Leu Lys Glu Ile Met Ala Gly
            375                 380                 385 agt gaa caa gaa ttt tcg ttc aag ttg ttg caa caa gtt aat cag ggt    1551
Ser Glu Gln Glu Phe Ser Phe Lys Leu Leu Gln Gln Val Asn Gln Gly
390                 395                 400 tta tct tca gcc agg aat atc ggt ata ctt aat gca act gga gaa tat    1599
Leu Ser Ser Ala Arg Asn Ile Gly Ile Leu Asn Ala Thr Gly Glu Tyr
405                 410                 415                 420 atc ttt ttt ttg gat tca gat gat gaa ata gaa agc aat ttt gtg gag    1647
Ile Phe Phe Leu Asp Ser Asp Asp Glu Ile Glu Ser Asn Phe Val Glu
                425                 430                 435 aca att ttg act agt tgc tat aaa tac agt caa ccg gat aca ctt atc    1695
Thr Ile Leu Thr Ser Cys Tyr Lys Tyr Ser Gln Pro Asp Thr Leu Ile
            440                 445                 450 ttt gat tat agt agc att gat gaa ttt gga aat gct ttg gac agt aat    1743
Phe Asp Tyr Ser Ser Ile Asp Glu Phe Gly Asn Ala Leu Asp Ser Asn
            455                 460                 465 tat ggg cat gga agt att tat cgt caa aaa gat ttg tgt aca agt gag    1791
Tyr Gly His Gly Ser Ile Tyr Arg Gln Lys Asp Leu Cys Thr Ser Glu
470                 475                 480 caa ata tta act gca ttg tct aaa gat gag ata cca aca act gca tgg    1839
Gln Ile Leu Thr Ala Leu Ser Lys Asp Glu Ile Pro Thr Thr Ala Trp
485                 490                 495                 500 tca ttt gta aca aaa cgc tct gtg att gaa aaa cac gat tta cta ttt    1887
Ser Phe Val Thr Lys Arg Ser Val Ile Glu Lys His Asp Leu Leu Phe
                505                 510                 515 tct gtt gga aaa aaa ttt gaa gat aac aat ttt acg ccg aaa gtt ttt    1935
Ser Val Gly Lys Lys Phe Glu Asp Asn Asn Phe Thr Pro Lys Val Phe
            520                 525                 530 tac ttt agt aaa aac att gtt gtt att tcc cta aga ttg tat aga tat    1983
```

```
                Tyr Phe Ser Lys Asn Ile Val Val Ile Ser Leu Arg Leu Tyr Arg Tyr
                        535                 540                 545 agg aaa cgc tct ggg tct att atg agt aat cgc ccg gaa aaa ttc ttt       2031
Arg Lys Arg Ser Gly Ser Ile Met Ser Asn Arg Pro Glu Lys Phe Phe
    550                 555                 560 tcg gac gac gcc att ttt gta aca tat gac tta tta gat ttt tat gat       2079
Ser Asp Asp Ala Ile Phe Val Thr Tyr Asp Leu Leu Asp Phe Tyr Asp
565                 570                 575                 580 cag tat aaa att cgg gaa ttg gga gca gta gtt ggt aaa ata gtt atg       2127
Gln Tyr Lys Ile Arg Glu Leu Gly Ala Val Val Gly Lys Ile Val Met
                585                 590                 595 aca aca tta gct tct ttt cca gat tcg aaa aaa ttg tat aat gaa tta       2175
Thr Thr Leu Ala Ser Phe Pro Asp Ser Lys Lys Leu Tyr Asn Glu Leu
            600                 605                 610 aat cca atc aga aaa aaa gta ttt aaa gat tat att tca ata gaa aaa       2223
Asn Pro Ile Arg Lys Lys Val Phe Lys Asp Tyr Ile Ser Ile Glu Lys
        615                 620                 625 aga cat act aaa cgg ata aaa atg tat gta aaa atg tat gtt ttt tct       2271
Arg His Thr Lys Arg Ile Lys Met Tyr Val Lys Met Tyr Val Phe Ser
    630                 635                 640 tct tat gtt gga tat aaa ctt tac aga ctg gta aaa ggt aaa cac tgg       2319
Ser Tyr Val Gly Tyr Lys Leu Tyr Arg Leu Val Lys Gly Lys His Trp
645                 650                 655                 660 aag tgaatataat ttttaatctt atttatg                                     2349
Lys
```

<210> SEQ ID NO 13
<211> LENGTH: 332
<212> TYPE: PRT
<213> ORGANISM: Lactococcus lactis

<400> SEQUENCE: 13

```
Leu Ser Glu Asn Leu Ile Ser Ile Ile Val Pro Val Tyr Asn Ser Glu
 1               5                  10                  15

Lys Tyr Leu Arg Ala Ala Ile His Ser Leu Leu Asn Gln Thr Tyr Gln
            20                  25                  30

Asn Ile Glu Val Ile Leu Ile Asn Asp Gly Ser Thr Asp Gly Ser Gln
        35                  40                  45

Glu Leu Ile Ser Ser Phe Gln Lys Lys Asp Lys Arg Ile Lys Leu Tyr
    50                  55                  60

Asn Thr Lys Asn Leu Gly Val Ser His Ala Arg Asn Tyr Gly Ile Asp
65                  70                  75                  80

Arg Ala Ser Gly Ser Tyr Ile Met Phe Leu Asp Pro Asp Asp Thr Tyr
                85                  90                  95

Asp Lys Ser Tyr Cys Leu Glu Met Ile Gly Leu Ile Asn Lys Phe Asn
            100                 105                 110

Ala Asp Val Val Met Ser Asn Tyr Tyr Ile Cys Lys Gly Lys Asn Ile
        115                 120                 125

Tyr Pro Asn Val Asn Asn Asp Leu Leu Glu Cys Glu Gly Leu Leu Ser
    130                 135                 140

Arg Asp Lys Thr Met Arg Ser Ile Leu Ser Asp Thr Gly Phe Lys Gly
145                 150                 155                 160

Phe Val Trp Thr Arg Ile Phe Arg Lys Asn Val Ile Asn Val Lys
                165                 170                 175

Phe Asn Glu Ser Ile Asn Tyr Leu Glu Asp Met Leu Phe Asn Ile Ser
            180                 185                 190

Ile Val His Asn Ala Arg Ile Ile Ala Tyr Thr Asn Lys Arg His Tyr
```

```
                195                 200                 205
Phe Tyr Leu Gln Arg Glu Asp Ser Ala Ser Lys Lys Phe Ser Lys Ser
    210                 215                 220

Phe Phe Lys Ser Leu Asn Leu Ile Arg Gly Lys Val Asp Pro Glu Phe
225                 230                 235                 240

Tyr Ser Gln Ile Asp Ser Val Ile Phe Tyr Asn Leu Val Gly Trp Leu
                245                 250                 255

Ile Thr Glu Arg Lys Ser Arg Glu Asn Ser Gln Phe Ile Arg Arg Asn
            260                 265                 270

Ile Lys Asn Met Lys Ser Gln Val Lys Phe Lys Thr Leu Lys Met Glu
        275                 280                 285

Asn Pro Ile Lys Asn Leu Ile Leu Lys Leu Ser Tyr Ala Phe Pro Leu
    290                 295                 300

Val Gly Ser Cys Met Ile His Met Leu Ser Val Phe Met Lys Thr Lys
305                 310                 315                 320

Leu Tyr Ser Lys Leu Met Ser Met Leu Arg Lys Gly
                325                 330

<210> SEQ ID NO 14
<211> LENGTH: 329
<212> TYPE: PRT
<213> ORGANISM: Lactococcus lactis

<400> SEQUENCE: 14

Met Asn Pro Leu Ile Ser Ile Ile Val Pro Ile Tyr Asn Val Glu Lys
1               5                   10                  15

Tyr Ile Gly Ser Leu Val Asn Ser Leu Leu Lys Gln Thr Asn Lys Asn
                20                  25                  30

Phe Glu Val Ile Phe Ile Asp Asp Gly Ser Thr Asp Glu Ser Met Gln
            35                  40                  45

Ile Leu Lys Glu Ile Met Ala Gly Ser Glu Gln Glu Phe Ser Phe Lys
        50                  55                  60

Leu Leu Gln Gln Val Asn Gln Gly Leu Ser Ser Ala Arg Asn Ile Gly
65                  70                  75                  80

Ile Leu Asn Ala Thr Gly Glu Tyr Ile Phe Phe Leu Asp Ser Asp Asp
                85                  90                  95

Glu Ile Glu Ser Asn Phe Val Glu Thr Ile Leu Thr Ser Cys Tyr Lys
            100                 105                 110

Tyr Ser Gln Pro Asp Thr Leu Ile Phe Asp Tyr Ser Ser Ile Asp Glu
        115                 120                 125

Phe Gly Asn Ala Leu Asp Ser Asn Tyr Gly His Gly Ser Ile Tyr Arg
    130                 135                 140

Gln Lys Asp Leu Cys Thr Ser Glu Gln Ile Leu Thr Ala Leu Ser Lys
145                 150                 155                 160

Asp Glu Ile Pro Thr Thr Ala Trp Ser Phe Val Thr Lys Arg Ser Val
                165                 170                 175

Ile Glu Lys His Asp Leu Leu Phe Ser Val Gly Lys Lys Phe Glu Asp
            180                 185                 190

Asn Asn Phe Thr Pro Lys Val Phe Tyr Phe Ser Lys Asn Ile Val Val
        195                 200                 205

Ile Ser Leu Arg Leu Tyr Arg Tyr Arg Lys Arg Ser Gly Ser Ile Met
    210                 215                 220

Ser Asn Arg Pro Glu Lys Phe Ser Asp Asp Ala Ile Phe Val Thr
225                 230                 235                 240
```

```
Tyr Asp Leu Leu Asp Phe Tyr Asp Gln Tyr Lys Ile Arg Glu Leu Gly
                245                 250                 255

Ala Val Val Gly Lys Ile Val Met Thr Thr Leu Ala Ser Phe Pro Asp
            260                 265                 270

Ser Lys Lys Leu Tyr Asn Glu Leu Asn Pro Ile Arg Lys Lys Val Phe
        275                 280                 285

Lys Asp Tyr Ile Ser Ile Glu Lys Arg His Thr Lys Arg Ile Lys Met
    290                 295                 300

Tyr Val Lys Met Tyr Val Phe Ser Ser Tyr Val Gly Tyr Lys Leu Tyr
305                 310                 315                 320

Arg Leu Val Lys Gly Lys His Trp Lys
                325

<210> SEQ ID NO 15
<211> LENGTH: 1612
<212> TYPE: DNA
<213> ORGANISM: Lactococcus lactis
<220> FEATURE:
<221> NAME/KEY: CDS
<222> LOCATION: (76)..(1488)

<400> SEQUENCE: 15
ggtggacagg aggacacaat ttttaatcct tcctgttata tagttttttgt ttaatatttt       60 tcgggagggt tatta atg caa atc gca aaa aat tat ctt tat aat gca ata        111
               Met Gln Ile Ala Lys Asn Tyr Leu Tyr Asn Ala Ile
                 1               5                  10 tat cag gtc ttt ata ata att gtg cca tta ctt acc att cct tat ttg        159
Tyr Gln Val Phe Ile Ile Ile Val Pro Leu Leu Thr Ile Pro Tyr Leu
        15                  20                  25 tca aga att ttg ggc cct tca ggt att gga att aac tca tat acc aat        207
Ser Arg Ile Leu Gly Pro Ser Gly Ile Gly Ile Asn Ser Tyr Thr Asn
 30                  35                  40 tct att gtt cag tat ttt gtt tta ttt ggt agt ata gga gtc ggt ttg        255
Ser Ile Val Gln Tyr Phe Val Leu Phe Gly Ser Ile Gly Val Gly Leu
 45                  50                  55                  60 tat ggg aat cgt cag att gcc ttt gtt agg gat aat cag gtc aaa atg        303
Tyr Gly Asn Arg Gln Ile Ala Phe Val Arg Asp Asn Gln Val Lys Met
                 65                  70                  75 tct aaa gtc ttt tat gaa ata ttt att tta aga cta ttt aca ata tgt        351
Ser Lys Val Phe Tyr Glu Ile Phe Ile Leu Arg Leu Phe Thr Ile Cys
             80                  85                  90 tta gca tat ttt ttg ttc gtt gct ttt tta atc att aat ggt cag tat        399
Leu Ala Tyr Phe Leu Phe Val Ala Phe Leu Ile Ile Asn Gly Gln Tyr
         95                 100                 105 cat gca tac tat ttg tct caa tcc att gct ata gtt gca gct gca ttt        447
His Ala Tyr Tyr Leu Ser Gln Ser Ile Ala Ile Val Ala Ala Ala Phe
    110                 115                 120 gat atc tct tgg ttt ttt atg gga att gaa aat ttt aaa gta act gta        495
Asp Ile Ser Trp Phe Phe Met Gly Ile Glu Asn Phe Lys Val Thr Val
125                 130                 135                 140 tta aga aat ttt ata gtt aag tta ctt gct cta ttc agt att ttc cta        543
Leu Arg Asn Phe Ile Val Lys Leu Leu Ala Leu Phe Ser Ile Phe Leu
                145                 150                 155 ttt gtc aaa tct tac aat gat ttg aat ata tat ata ttg ata aca gtt        591
Phe Val Lys Ser Tyr Asn Asp Leu Asn Ile Tyr Ile Leu Ile Thr Val
            160                 165                 170 tta tct aca tta att ggt aat tta act ttt ttc cca agt tta cac aga        639
Leu Ser Thr Leu Ile Gly Asn Leu Thr Phe Phe Pro Ser Leu His Arg
        175                 180                 185
```

```
tat ctc gta aag gtt aac tat cgt gaa tta agg cca ata aag cat tta    687
Tyr Leu Val Lys Val Asn Tyr Arg Glu Leu Arg Pro Ile Lys His Leu
    190                 195                 200 aag caa tct tta gtc atg ttt atc cca caa att gct gtc caa att tat    735
Lys Gln Ser Leu Val Met Phe Ile Pro Gln Ile Ala Val Gln Ile Tyr
205                 210                 215                 220 tgg gtt ttg aat aaa acg atg tta ggt tca ttg gat tct gtc acg agc    783
Trp Val Leu Asn Lys Thr Met Leu Gly Ser Leu Asp Ser Val Thr Ser
                225                 230                 235 tcc ggc ttt ttt gat cag tct gat aaa ata gtt aaa ctg gtt ttg gct    831
Ser Gly Phe Phe Asp Gln Ser Asp Lys Ile Val Lys Leu Val Leu Ala
            240                 245                 250 att gct act gca aca ggt act gtc atg ttg cca cgt gtt gca aat gcc    879
Ile Ala Thr Ala Thr Gly Thr Val Met Leu Pro Arg Val Ala Asn Ala
        255                 260                 265 ttt gca cat aga gag tat agt aaa att aag gaa tac atg tac gca ggt    927
Phe Ala His Arg Glu Tyr Ser Lys Ile Lys Glu Tyr Met Tyr Ala Gly
    270                 275                 280 ttt tct ttt gtg tcg gca att tcg att cct atg atg ttt ggt ctg ata    975
Phe Ser Phe Val Ser Ala Ile Ser Ile Pro Met Met Phe Gly Leu Ile
285                 290                 295                 300 gct att act cct aaa ttc gtg cca ctt ttt ttt aca tct caa ttt agt   1023
Ala Ile Thr Pro Lys Phe Val Pro Leu Phe Phe Thr Ser Gln Phe Ser
                305                 310                 315 gat gtt att cct gtg tta atg atc gag tca atc gca att att ttt ata   1071
Asp Val Ile Pro Val Leu Met Ile Glu Ser Ile Ala Ile Ile Phe Ile
            320                 325                 330 gct tgg agc aac gca ata ggt act caa tat ctt tta cca act aat caa   1119
Ala Trp Ser Asn Ala Ile Gly Thr Gln Tyr Leu Leu Pro Thr Asn Gln
        335                 340                 345 aat aag tca tat aca gtg tcg gtg atc att gga gcg ata gtc aat tta   1167
Asn Lys Ser Tyr Thr Val Ser Val Ile Ile Gly Ala Ile Val Asn Leu
    350                 355                 360 atg tta aat att cca ctg att ata tat cta ggt act gtt ggt gca tca   1215
Met Leu Asn Ile Pro Leu Ile Ile Tyr Leu Gly Thr Val Gly Ala Ser
365                 370                 375                 380 att gca act gta att tct gaa atg tct gta act gtg tat caa ctt ttt   1263
Ile Ala Thr Val Ile Ser Glu Met Ser Val Thr Val Tyr Gln Leu Phe
                385                 390                 395 ata att cat aaa cag ctt aat ttg cat aca ctg ttt gcg gat tta tct   1311
Ile Ile His Lys Gln Leu Asn Leu His Thr Leu Phe Ala Asp Leu Ser
            400                 405                 410 aag tat tta att gca gga tta gtg atg ttt cta att gtc ttt aaa att   1359
Lys Tyr Leu Ile Ala Gly Leu Val Met Phe Leu Ile Val Phe Lys Ile
        415                 420                 425 agt ttg tta aca ccg aca tct tgg ata ttc att ctg ttg gaa att act   1407
Ser Leu Leu Thr Pro Thr Ser Trp Ile Phe Ile Leu Leu Glu Ile Thr
    430                 435                 440 gtg ggc ata att att tat gtt gtt tta tta ata ttt tta aag gca gaa   1455
Val Gly Ile Ile Ile Tyr Val Val Leu Leu Ile Phe Leu Lys Ala Glu
445                 450                 455                 460 ata att aat aag cta aag ttt att atg cat aaa tagaggtatg gatttaggta  1508
Ile Ile Asn Lys Leu Lys Phe Ile Met His Lys
                465                 470 cctgccttat tgaaataac ggtgagtcaa tggtattggg catatttgac gctcaccttc   1568
aatttgtttt ggtcgacttg attgtagcac aggacaatat gtct                   1612

<210> SEQ ID NO 16
<211> LENGTH: 471
```

```
<212> TYPE: PRT
<213> ORGANISM: Lactococcus lactis

<400> SEQUENCE: 16

Met Gln Ile Ala Lys Asn Tyr Leu Tyr Asn Ala Ile Tyr Gln Val Phe
 1               5                  10                  15

Ile Ile Ile Val Pro Leu Leu Thr Ile Pro Tyr Leu Ser Arg Ile Leu
             20                  25                  30

Gly Pro Ser Gly Ile Gly Ile Asn Ser Tyr Thr Asn Ser Ile Val Gln
         35                  40                  45

Tyr Phe Val Leu Phe Gly Ser Ile Gly Val Gly Leu Tyr Gly Asn Arg
     50                  55                  60

Gln Ile Ala Phe Val Arg Asp Asn Gln Val Lys Met Ser Lys Val Phe
 65                  70                  75                  80

Tyr Glu Ile Phe Ile Leu Arg Leu Phe Thr Ile Cys Leu Ala Tyr Phe
                 85                  90                  95

Leu Phe Val Ala Phe Leu Ile Ile Asn Gly Gln Tyr His Ala Tyr Tyr
            100                 105                 110

Leu Ser Gln Ser Ile Ala Ile Val Ala Ala Ala Phe Asp Ile Ser Trp
        115                 120                 125

Phe Phe Met Gly Ile Glu Asn Phe Lys Val Thr Val Leu Arg Asn Phe
    130                 135                 140

Ile Val Lys Leu Leu Ala Leu Phe Ser Ile Phe Leu Phe Val Lys Ser
145                 150                 155                 160

Tyr Asn Asp Leu Asn Ile Tyr Ile Leu Ile Thr Val Leu Ser Thr Leu
                165                 170                 175

Ile Gly Asn Leu Thr Phe Phe Pro Ser Leu His Arg Tyr Leu Val Lys
            180                 185                 190

Val Asn Tyr Arg Glu Leu Arg Pro Ile Lys His Leu Lys Gln Ser Leu
        195                 200                 205

Val Met Phe Ile Pro Gln Ile Ala Val Gln Ile Tyr Trp Val Leu Asn
    210                 215                 220

Lys Thr Met Leu Gly Ser Leu Asp Ser Val Thr Ser Ser Gly Phe Phe
225                 230                 235                 240

Asp Gln Ser Asp Lys Ile Val Lys Leu Val Leu Ala Ile Ala Thr Ala
                245                 250                 255

Thr Gly Thr Val Met Leu Pro Arg Val Ala Asn Ala Phe Ala His Arg
            260                 265                 270

Glu Tyr Ser Lys Ile Lys Glu Tyr Met Tyr Ala Gly Phe Ser Phe Val
        275                 280                 285

Ser Ala Ile Ser Ile Pro Met Met Phe Gly Leu Ile Ala Ile Thr Pro
    290                 295                 300

Lys Phe Val Pro Leu Phe Phe Thr Ser Gln Phe Ser Asp Val Ile Pro
305                 310                 315                 320

Val Leu Met Ile Glu Ser Ile Ala Ile Phe Ile Ala Trp Ser Asn
                325                 330                 335

Ala Ile Gly Thr Gln Tyr Leu Leu Pro Thr Asn Gln Asn Lys Ser Tyr
            340                 345                 350

Thr Val Ser Val Ile Ile Gly Ala Ile Val Asn Leu Met Leu Asn Ile
        355                 360                 365

Pro Leu Ile Ile Tyr Leu Gly Thr Val Gly Ala Ser Ile Ala Thr Val
    370                 375                 380

Ile Ser Glu Met Ser Val Thr Val Tyr Gln Leu Phe Ile Ile His Lys
385                 390                 395                 400
```

-continued

```
Gln Leu Asn Leu His Thr Leu Phe Ala Asp Leu Ser Lys Tyr Leu Ile
                405                 410                 415

Ala Gly Leu Val Met Phe Leu Ile Val Phe Lys Ile Ser Leu Leu Thr
            420             425                 430

Pro Thr Ser Trp Ile Phe Ile Leu Leu Glu Ile Thr Val Gly Ile Ile
        435             440                 445

Ile Tyr Val Val Leu Leu Ile Phe Leu Lys Ala Glu Ile Ile Asn Lys
    450                 455             460

Leu Lys Phe Ile Met His Lys
465                 470
```